United States Patent [19]

Miesel

[11] 4,405,552

[45] Sep. 20, 1983

[54] 1-BENZOYL-3-(ARYLPHYRIDYL)UREA COMPOUNDS

[75] Inventor: John L. Miesel, Indianapolis, Ind.

[73] Assignee: Eli Lilly and Company, Indianapolis, Ind.

[21] Appl. No.: 264,494

[22] Filed: May 18, 1981

Related U.S. Application Data

[63] Continuation-in-part of Ser. No. 240,331, Mar. 3, 1981, abandoned.

[51] Int. Cl.³ .................... A01N 43/40; C07D 213/74
[52] U.S. Cl. ...................................... 424/263; 546/309
[58] Field of Search ................. 546/306, 309; 424/263

[56] References Cited

U.S. PATENT DOCUMENTS

| | | | |
|---|---|---|---|
| 3,748,356 | 7/1973 | Wellinga et al. | 260/553 |
| 4,083,977 | 4/1978 | Miesel | 424/250 |
| 4,133,956 | 1/1979 | Abdulla | 544/336 |
| 4,173,639 | 11/1979 | Suhr | 424/263 |
| 4,219,557 | 8/1980 | Miesel | 424/263 |

FOREIGN PATENT DOCUMENTS

| | | |
|---|---|---|
| 8881 | 3/1980 | European Pat. Off. . |
| 2926480 | of 0000 | Fed. Rep. of Germany . |
| 7105350 | of 0000 | Netherlands . |

OTHER PUBLICATIONS

Chem. Abstracts 98:(9):71937v, (1983).
Chem. Abstracts 67(9):43658w, (1967).
C & E News, Jul. 25, 1977, pp. 24 & 57, and an unnumbered page comprising an application form.
"Abstracts of Papers" of 174th meeting of the American Chemical Society J. Agr. & Food Chem. 26 #1, 164, (Jan., Feb. 1978).

*Primary Examiner*—Ethel G. Love
*Attorney, Agent, or Firm*—Gerald V. Dahling; Kathleen R. S. Page; Arthur R. Whale

[57] ABSTRACT

The present invention is directed to 1-benzoyl-3-(arylpyridyl)urea compounds useful as insecticides.

237 Claims, No Drawings

1-BENZOYL-3-(ARYLPHYRIDYL)UREA COMPOUNDS

CROSS-REFERENCE

This application is a continuation-in-part of co-pending application Ser. No. 240,331, filed Mar. 3, 1981, now abandoned.

SUMMARY OF THE INVENTION

The invention is directed to compounds of the formula:

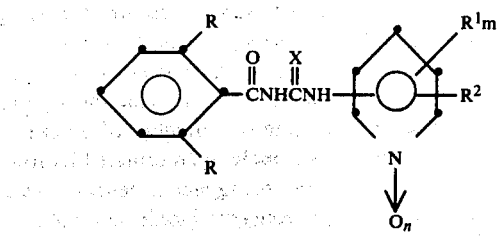

wherein each R is independently
 H,
 Br,
 Cl,
 F,
 CH$_3$, or
 OCH$_3$
with the proviso that both R groups are not simultaneously H, and with the further proviso that when one R group is fluoro or methoxy the other R group is not simultaneously H;
 X=O or S;
 n=0-1;
 R$^1$ is independently
  Cl,
  Br,
  CH$_3$, or
  CH$_3$CH$_2$;
 m=0-2; and
 R$^2$ is a phenyl radical of the formula:

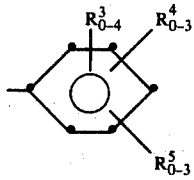

R$^3$ represents
  Br,
  Cl, or
  F;
 R$^4$ represents
  CF$_3$,
  OCF$_3$,
  OC$_2$F$_5$,
  OCF$_2$CF$_2$H, or
  SCF$_3$;
 R$^5$ represents
  Methyl,
  Ethyl,
  Methoxy,
  Ethoxy;
  SCH$_3$, or
  SCH$_2$CH$_3$;
with the limitation that the entire substituted phenyl radical bears
 (1) not more than 4 substituents, when all substituents are halo substituents;
 (2) not more than 3 substituents, when any one substituent is other than halo;
 (3) not more than 2 different substituents;
and wherein positions on the pyridine ring are as follows:
 (1) the NH to pyridine bond is at the 2-position of the pyridine ring, the R$^2$ group is at the 5-position of the pyridine ring, and when m=1-2, any R$^1$ is at the 4-, 6-, or 4 and 6-positions of the pyridine ring, subject to the limitation that
  (a) when simultaneously R$^1$ represents bromo and n=0, m=1 and R$^1$ is at the 6-position;
  (b) when simultaneously R$^1$ represents Cl and m=1, R$^1$ is at the 6-position;
  (c) when simultaneously m and n=0 and each R represents OCH$_3$, R$^2$ is not unsubstituted phenyl, 3-chlorophenyl, 3,4-dichlorophenyl, or 4-methoxyphenyl;
  (d) when simultaneously m and n=0 and each R represents CH$_3$, R$^2$ is not 4-chlorophenyl;
  (e) when simultaneously m and n=0 and one R represents Cl and the other R represents H, R$^2$ is not 3-chlorophenyl, 3,4-dichlorophenyl, 4-tolyl, 4-methoxyphenyl, or 3,4,5-trimethoxyphenyl;
  (f) when simultaneously m=2 and n=0 and one R$^1$ moiety represents CH$_3$ or CH$_3$CH$_2$, the other R$^1$ moiety is not chloro or bromo;
  (g) when n=1, neither R group represents CH$_3$ or OCH$_3$, any R$^1$ represents CH$_3$ or Cl, and R$^2$ represents a para-substituted phenyl in which the substituent is Br, Cl, F, CH$_3$, or CF$_3$;
  (h) when n=1 and one R group simultaneously represents H, m=1-2; or
 (2) the NH to pyridine bond is at the 3-position of the pyridine ring, the R$^2$ group is at the 6-position of the pyridine ring, and when m=1, any R$^1$ is at the 5-position of the pyridine ring, subject to the limitation that m=0-1 and
  (a) when n=0, R$^1$ represents CH$_3$ or CH$_3$CH$_2$;
  (b) when simultaneously n=0 and one R represents Cl and the other R represents H, R$^2$ is not 3-chlorophenyl;
  (c) when simultaneously n=0 and one R represents CH$_3$ and the other R represents H, R$^2$ is not unsubstituted phenyl;
  (d) when n=1, each R independently represents Cl or F, any R$^1$ represents CH$_3$, and R$^2$ represents a para-substituted phenyl in which the substituent is Br, Cl, F, CH$_3$, or CF$_3$;
or an agriculturally acceptable acid addition salt thereof.

The present invention is also directed to methods employing and compositions comprising the above compounds as insecticides.

DETAILED DESCRIPTION OF THE INVENTION

For purposes of the present application, the compounds of this invention are named as substituted ureas, with numbering as follows:

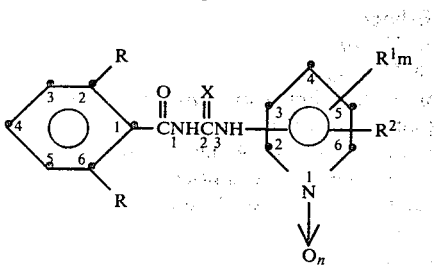

Therefore, the compounds are named as 1-(2-substituted or 2,6-disubstituted benzoyl)-3-(5-phenyl or substituted phenyl-2-pyridyl)ureas, thioureas, or acid addition salts, as 1-(2-substituted or 2,6-disubstituted benzoyl)-3-(5-substituted phenyl-2-pyridyl-1-oxide)ureas or thioureas, as 1-(2-substituted or 2,6-disubstituted benzoyl)-3-(6-phenyl or substituted phenyl-3-pyridyl)ureas, thioureas, or acid addition salts, or as 1-(2-substituted or 2,6-disubstituted benzoyl)-3-(6-substituted phenyl-3-pyridyl-1-oxide)ureas or thioureas.

The compounds of the present invention are readily prepared by the reaction of a 2-substituted or a 2,6-disubstituted benzoyl isocyanate or isothiocyanate of the formula

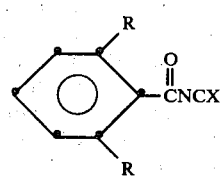

with a 2- or 3-pyridylamine of the formula

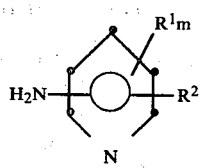

or a 1-oxide thereof. The reaction of an isocyanate or isothiocyanate with an amine is a known type of reaction, cf. U.S. Pat. Nos. 3,748,356 and 4,083,977. In general, the reaction is carried out in an organic solvent such as a hydrocarbon, chlorinated hydrocarbon, ethyl acetate, acetonitrile, and so forth, and at temperatures of about 0° C. to the boiling temperature of the solvent. Preferably the reaction is conducted at room temperature.

The acid addition salts are prepared by reacting a benzoyl urea or benzoyl thiourea product with the desired acid, in conventional procedures. Acids having a pKa of 3.0 or lower are preferred, and generally the mineral acids are preferred.

The benzoyl isocyanates which serve as starting materials are prepared by the reaction of the corresponding benzamide with oxalyl chloride by the method of Speziale et al., *J. Org. Chem.* 271 3742 (1962). The benzoyl isothiocyanates are prepared in known procedures by reacting the corresponding benzoyl chlorides with an inorganic thiocyanate such as ammonium thiocyanate, lead thiocyanate, and so forth.

The pyridylamine compounds are not well known in the art but may be synthesized in several different ways, some being adaptations or extensions of literature procedures. Some of these literature procedures are reviewed in *Pyridine and Its Derivatives*, ed. Klingsberg, especially Parts 2 and 3 (Interscience Publishers Inc., N.Y. 1961 and 1962). Many of the compounds serving as starting material for synthesis of the pyridylamines are commercially available and all can be prepared according to known procedures.

A preferred method for synthesizing certain 2-pyridylamine compounds is presented in synthesis route XI herein below. In this procedure, the cyclization of substituted or non-substituted -γ-[1-(hydroxy-, benzyloxy-, or $C_1$-$C_3$ alkoxyimino)$C_1$-$C_3$ alkane]-β-$C_1$-$C_3$ alkylbenzenebutanenitrile or substituted or non-substituted -γ-[1-(hydroxy, benzyloxy-, or $C_1$-$C_3$ alkoxyimino) $C_1$-$C_3$ alkane]benzenebutanenitrile to form a corresponding 2-pyridylamine is a novel reaction which can be carried out in any one of a number of different solvents. Preferred solvents include chlorinated hydrocarbons, alkylated benzene, halogenated benzene, and nitrobenzene provided that the oximinonitrile is soluble in the solvent and that the boiling point of the solvent is at least 110° C. and preferably higher than 140° C. Preferred catalysts, exemplified herein with methane sulfonic acid, are anhydrous acids which are partially miscible with the solvent and which have a high dissociation constant.

A particularly critical stage in this novel synthesis procedure is the addition of the oximinonitrile to the mixture of solvent and catalyst. This must be done while the latter mixture is being slowly distilled and stirred in order to insure that the desired cyclization will occur. The reaction mixture is then refluxed and the 2-pyridylamine is subsequently recovered according to conventional procedures.

Various synthetic routes which are useful for the preparation of pyridylamine compounds are presented and illustrated as follows.

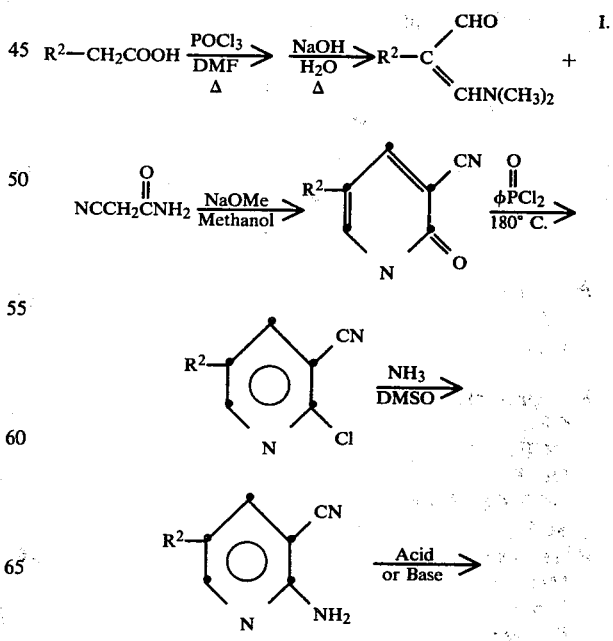

-continued
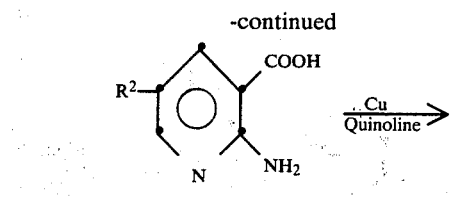
This synthetic route is illustrated by Examples 1–6.
II. 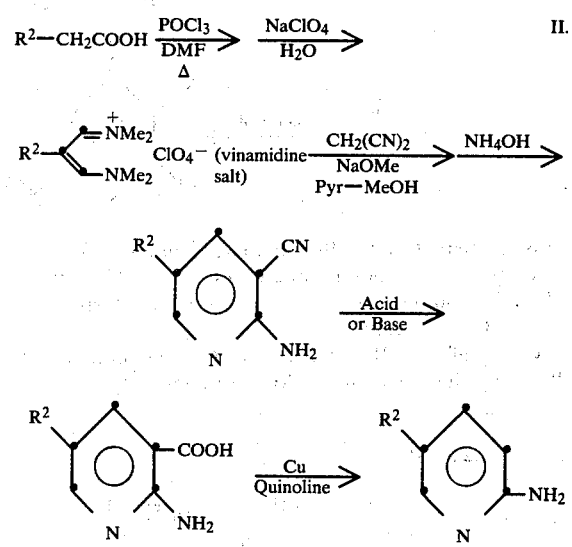
This synthetic route is illustrated by Examples 10–12.
III. 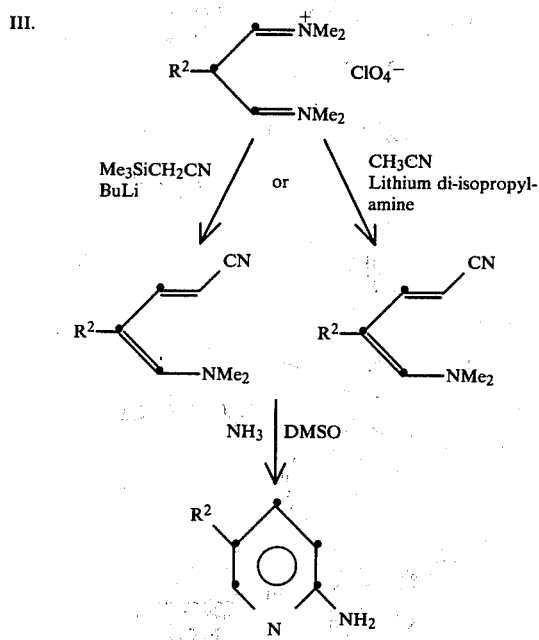
This synthetic route is illustrated by Examples 14–15.
IV. (Useful for $R^1=CH_3$ or $CH_3CH_2$ and $m=1$ compounds).
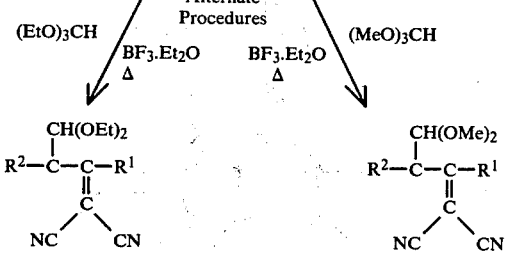
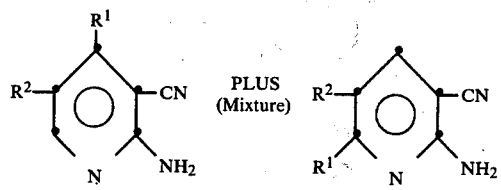
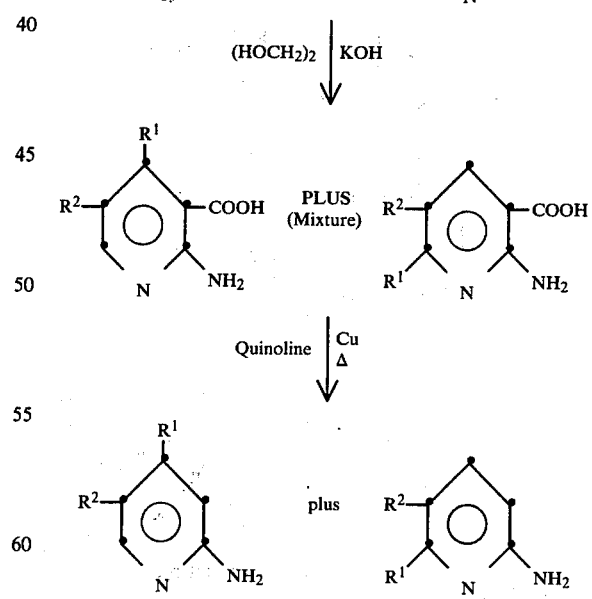
This synthesis route is illustrated by Examples 17 to 23 wherein $R^1=CH_3$ for simplicity.
V. (Useful for $R^1=CH_3$ or $CH_3CH_2$ and $m=2$ compounds).

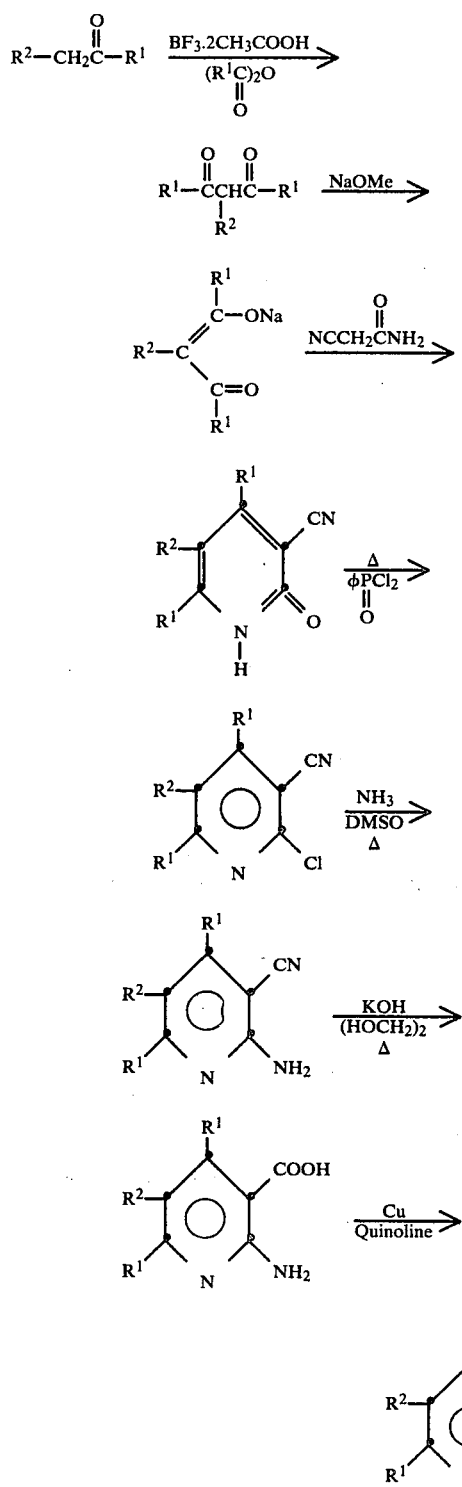

This synthesis route is illustrated by Examples 26 to 31 wherein each $R^1 = CH_3$ for simplicity.

VI. In the following synthetic route $R^1$ represents $CH_3$ or $CH_3CH_2$ and Z independently represents $R^1$ or H. The synthetic route is useful for compounds wherein $m=1$ and $R^1$ represents $CH_3$ or $CH_3CH_2$, or for compounds wherein $m=2$ and each $R^1$ independently represents $CH_3$ or $CH_3CH_2$.

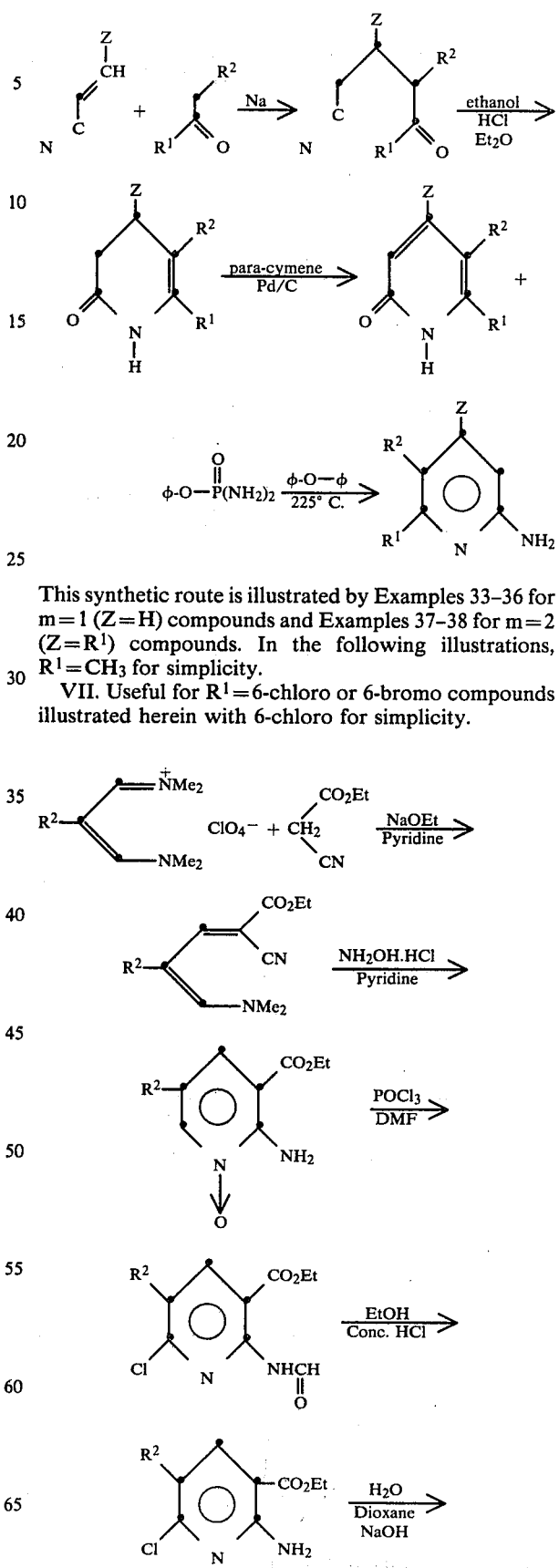

This synthetic route is illustrated by Examples 33–36 for $m=1$ (Z=H) compounds and Examples 37–38 for $m=2$ (Z=$R^1$) compounds. In the following illustrations, $R^1 = CH_3$ for simplicity.

VII. Useful for $R^1 = $ 6-chloro or 6-bromo compounds illustrated herein with 6-chloro for simplicity.

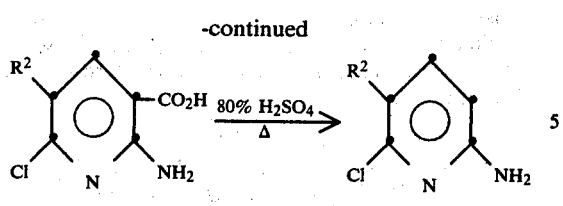

This synthetic route is illustrated by Examples 41–46. The above reactions can also be used for synthesis of $R^1$=4,6-dichloro compounds by reacting, according to the teaching of Example 60, the 6-chloro product of Example 43 with MCPB in acetone to yield an oxide. The 6-chloro oxide thus obtained is then reacted, according to the teaching of Example 43, to form a 4,6-dichloro intermediate which is converted to the desired pyridylamine by the procedure taught in Examples 44, 45, and 46.

VIII. Useful for 3-pyridylamine compounds wherein m=0–1.

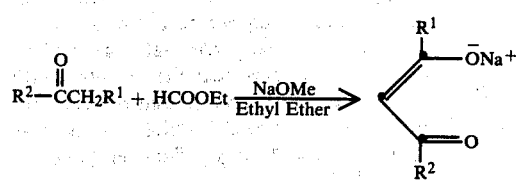

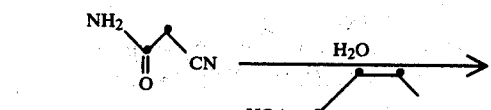

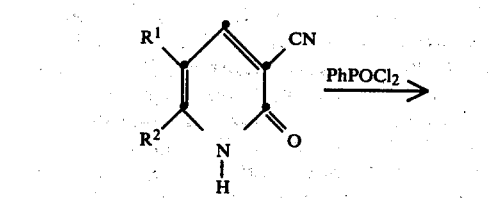

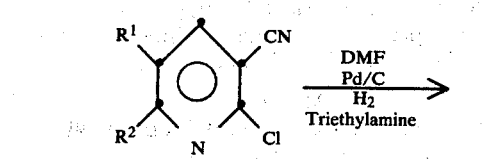

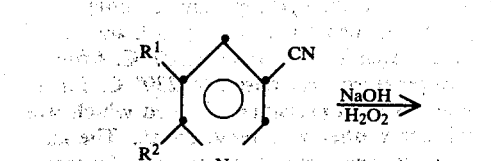

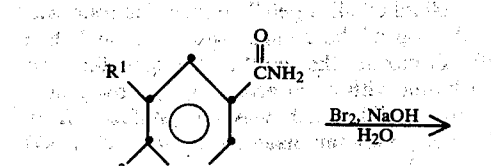

This synthetic route is illustrated by Examples 48–52 for m=0 and 54–58 for m=1 compounds.

IX. (Useful for 2- or 3-pyridylamine-1-oxide compounds illustrated herein for 2-pyridylamine-1-oxide wherein m=0 for simplicity).

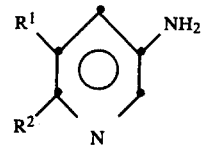

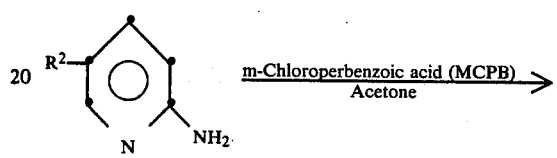

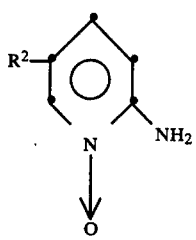

This synthetic route is illustrated by Example 60.

X. A procedure for the synthesis of 2-pyridylamine compounds wherein $R^1$ is 6—$CH_3$ or 6—$CH_3CH_2$ and $R^2$ is non-substituted phenyl or substituted phenyl in which the substituent has an electron withdrawing power which is greater than hydrogen, is as follows.

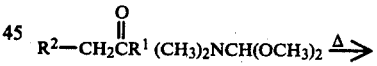

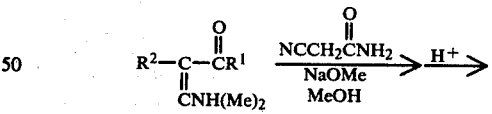

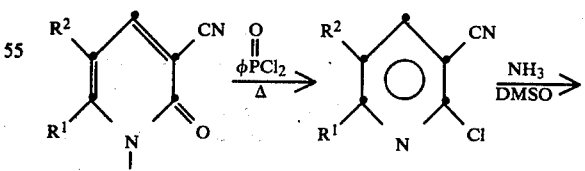

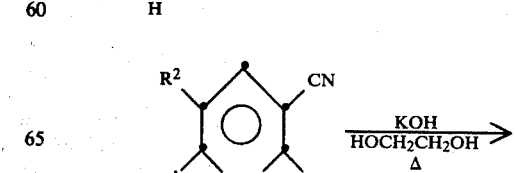

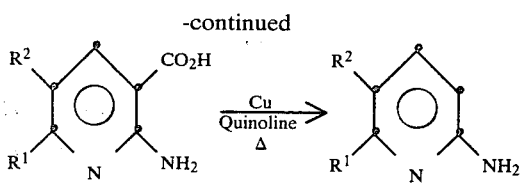

This synthetic route is illustrated by Examples 62-66 wherein $R^1 = CH_3$ and $R^2 =$ non-substituted phenyl for simplicity.

XI. An alternate and more preferred procedure for the synthesis of 2-pyridylamine compounds wherein m is 0-2 and $R^1$ independently is $CH_3$ or $CH_3CH_2$ is shown below. In the following reactions Y independently represents H or $R^1$ as limited above.

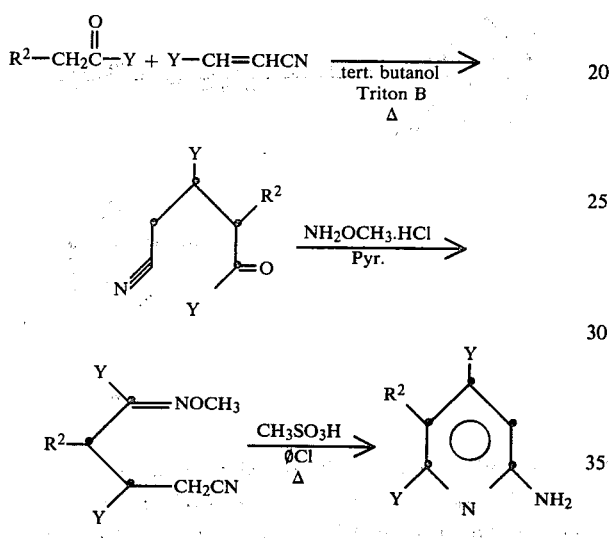

This synthetic route is illustrated by Examples 68-70 wherein $m=2$ and $Y=CH_3$ for simplicity.

The following examples illustrate the compounds of the present invention.

EXAMPLE 1:
2-(4-CHLOROPHENYL)-3-(DIMETHYLAMINO)ACROLEIN

Dimethylformamide (81 grams) was added dropwise to phosphorus oxychloride (138 grams) keeping the temperature at 20°-30° C. by external cooling. The mixture was stirred for 15 minutes at room temperature and then 4-chlorophenylacetic acid (50 grams in 30 ml DMF) was added. After heating to 65°-75° C. for 20 hours, the reaction mixture was cooled, poured onto 1 kilogram of ice and made basic to pH 12 with 50% sodium hydroxide, and then heated on a steam bath for 1 hour. The precipitate which formed was filtered, washed with water, dried in vacuo, and then recrystallized from ethyl acetate yielding the desired product, m.p. 117°-120° C.

EXAMPLE 2:
5-(4-CHLOROPHENYL)-3-CYANO-2-(1H)-PYRIDONE

Sodium (7 grams in 300 ml methanol) was stirred while a methanolic solution of 2-cyanoacetamide (16 grams) and 2-(4-chlorophenyl)-3-(dimethylamino)acrolein (37 grams) was added. The mixture was refluxed for 1 hour and the resulting precipitate was filtered, washed with ethanol, dissolved in hot water, and then acidified. The resulting precipitate was filtered, washed with water, and identified as the desired product, m.p. 278°-280° C.

EXAMPLE 3:
2-CHLORO-5-(4-CHLOROPHENYL)-3-PYRIDINECARBONITRILE

A mixture of 3-cyano-5-(4-chlorophenyl)-2-(1H)-pyridone (2.0 grams) and phenylphosphonic dichloride (3.8 grams) was heated for 4 hours at 175° C. in an oil bath. The mixture was poured into ice water and was made alkaline by stirring with $NH_4OH$. The resulting brownish solid product was used without further purification, yield 2.0 g., m.p. 185°-187° C.

EXAMPLE 4:
2-AMINO-5-(4-CHLOROPHENYL)-3-PYRIDINECARBONITRILE

A solution of 2-chloro-5-(4-chlorophenyl)-3-pyridinecarbonitrile (2.0 grams) in 30 ml DMSO was heated in an oil bath at 80°-90° C. and then treated with gaseous $NH_3$ for 2½ hours. The reaction mixture was allowed to stand at room temperature for about 60 hours and then additional starting material (4 g) in 35 ml DMSO was added. The mixture was then treated with $NH_3$ at 80°-90° C. for about 28 hours and poured into ice water. The tan solid precipitate which formed was filtered and used without further purification, yield 5.5 grams, m.p. 202°-204° C.

EXAMPLE 5:
2-AMINO-5-(4-CHLOROPHENYL)-3-PYRIDINECARBOXYLIC ACID

2-Amino-5-(4-chlorophenyl)-3-pyridinecarbonitrile (2.0 grams) in 25 ml 50% $H_2SO_4$ was refluxed for 24 hours. The acidic solution was poured into ice water to give a yellow solid which was filtered and identified by NMR as the desired compound, yield 2.7 grams.

An alkaline hydrolysis procedure may also be used to synthesize the desired compound. Accordingly, 2-amino-5-(4-chlorophenyl)-3-pyridinecarbonitrile (2.0 grams) and KOH (2.0 grams) in 30 ml ethylene glycol were heated at 150° C. in an oil bath. After 3 hours the reaction was complete and the alkaline solution was poured into ice water and acidified to give the desired solid. The final product was again confirmed by NMR, yield 2.3 grams, m.p. 300°-315° C. dec.

EXAMPLE 6:
5-(4-CHLOROPHENYL)-2-PYRIDYLAMINE

2-Amino-5-(4-chlorophenyl)-3-pyridinecarboxylic acid (1.0 gram), copper powder (0.2 gram), and 10 ml quinoline were heated in an oil bath at 205° C. After 2½ hours, the temperature was raised to 230° C. for an additional hour. A solid precipitate formed which was collected and then washed with ethyl acetate. The solution was then stripped and the residue chromatographed on 300 ml of silica gel. The gum-like solid was applied to the top of the column with ether and then eluted with additional ether until all the quinoline was removed. Elution with ethyl acetate very slowly produced a brown solid which was recrystallized from methanol-water giving tan plate-like crystals, yield 400 mg, m.p. 122°-124° C.

Calculated: C, 24.56; H, 4.43; N, 13.69. Found: C, 24.48; H, 4.33; N, 13.99.

EXAMPLE 7:
1-(2,6-DICHLOROBENZOYL)-3-(5-(4-CHLORO-PHENYL)-2-PYRIDYL)UREA 5-(4-Chlorophenyl)-2-pyridylamine (0.6 gram), 2,6-dichlorobenzoyl isocyanate (0.8 gram), in a small amount of dichloromethane were reacted at room temperature. A slight exothermic reaction was followed by an almost immediate precipitate. After 3 hours at room temperature, the reaction mixture was cooled in an ice bath and then filtered to give 770 mg of colorless crystals. The identity of the product was confirmed by NMR analysis, m.p. 230°-233° C.

Calculated: C, 54.25; H, 2.88; N, 9.99. Found: C, 54.28; H, 3.00; N, 10.23.

EXAMPLE 8:
1-(2,6-DIMETHOXYBENZOYL)-3-(5-(4-CHLORO-PHENYL)-2-PYRIDYL)UREA 5-(4-Chlorophenyl)-2-pyridylamine (0.6 gram), 2,6-dimethoxybenzoyl isocyanate (0.8 gram), in a small amount of dichloromethane were reacted for 2 hours at room temperature and produced a slight exothermic reaction but no precipitate. The mixture was then refluxed for 30 minutes, cooled to room temperature, and stripped. The crude solid which formed was recrystallized from about 50 ml ethanol to give 780 mg of needle-like crystals. The identity of the final product was confirmed by NMR, m.p. 205°-215° C.

Calculated: C, 21.24; H, 4.41; N, 10.20. Found: C, 20.99; H, 4.24; N, 10.01.

EXAMPLE 9:
1-(2-CHLOROBENZOYL)-3-(5-(4-CHLORO-PHENYL)-2-PYRIDYL)UREA 5-(4-Chlorophenyl)-2-pyridylamine (0.6 gram) and 2-chlorobenzoyl isocyanate (0.7 gram) were reacted according to the teaching of Example 7. The identity of the product was confirmed by NMR, yield 920 mg, m.p. 228°-231° C.

Calculated: C, 59.09; H, 3.39; N, 10.88. Found: C, 58.83; H, 3.12; N, 10.64.

EXAMPLE 10:
N-[2-(4-CHLOROPHENYL)-3-(DIME-THYLAMINO)-2-PROPENYLIDENE]-N-METHYLMETHANAMINIUM PERCHLORATE

DMF (219 grams) was added dropwise to 162 ml POCl₃ with constant stirring using an ice bath to maintain the temperature between 27°-30° C. The mixture was stirred at room temperature for 45 minutes, 4-chlorophenylacetic acid (102.3 grams) was added, and then the mixture was heated in an oil bath at 80°-90° C. for 3 hours. After standing for about 18 hours, the reaction mixture was poured on ice using an ice bath to maintain a near ambient temperature. Solid NaClO₄.-H₂O was added with vigorous stirring and a solid product formed which was filtered, washed with a 15% NaClO₄ solution, air dried, and recrystallized from boiling ethanol, yield 170.3 grams, m.p. 142°-146° C.

EXAMPLE 11:
2-AMINO-5-(4-CHLOROPHENYL)-3-PYRIDINECARBONITRILE

Sodium methoxide (16.2 grams) in 300 ml methanol and malononitrile (19.8 grams) in 50-100 ml methanol were added to N-[2-(4-chlorophenyl)-3-(dimethylamino)-2-propenylidene]-N-methylmethanaminium perchlorate (101.1 grams) in 300 ml pyridine at 0° C. in an ice-alcohol bath. The reaction mixture was stirred at room temperature for about 20 hours and then recooled to 0° C. Ammonium hydroxide (120 ml) was added and after three hours, a copious precipitate formed. The solid was filtered, washed with water, and shown by NMR to be the desired product, yield 44 grams, m.p. 202°-204° C. Addition of 600-800 ml of water to the filtrate gave additional product although impurities were present.

EXAMPLE 12:
5-(4-CHLOROPHENYL)-2-PYRIDYLAMINE 5-(4-Chlorophenyl)-2-amino-3-pyridinecarbononitrile was converted to the desired product according to the teaching of Examples 5-6. The identity of the desired compound was confirmed by NMR analysis.

EXAMPLE 13:
1-(2,6-DIFLUOROBENZOYL)-3-(5-(4-CHLORO-PHENYL)-2-PYRIDYL)UREA 5-(4-Chlorophenyl)-2-pyridylamine (2 grams) was dissolved in 90 ml acetonitrile and then reacted with 2,6-difluorobenzoyl isocyanate (2.6 grams) under nitrogen at room temperature. A solid formed immediately which, after stirring for about 15 hours, was collected and identified as the desired product by NMR analysis, yield 3.4 grams, m.p. 229°-234° C.

Calculated: C, 58.85; H, 3.12; N, 10.84. Found: C, 58.70; H, 3.08; N, 10.92.

EXAMPLE 14:
5-(DIMETHYLAMINO)-4-PHENYL-2,4-PENTADIENENITRILE

Trimethylsilylacetonitrile (5.65 grams prepared according to J. Chem. Soc., Perkin 1, 1979; 26-30) in 10 ml THF was added to 20.6 ml n-butyl lithium in 20 ml THF at a temperature of −68°−−70° C. A dry ice-acetone bath was used to maintained the temperature for about 45 minutes after the addition. The mixture was then warmed to about −40° C. and a solution of 15 grams of vinamidine salt (analogous to Example 10) in 40 ml pyridine was added fairly quickly dropwise keeping the temperature at approximately −45°−−40° C. After about 1 hour the reaction mixture was warmed to room temperature and the solid which formed during the addition went into solution. The mixture was stirred for 20 hours and after the solvent was removed in vacuo, a thick oil formed which was dissolved in ethyl acetate. The organic layer was washed several times with water, then a saturated NaCl solution, and finally was dried in vacuo leaving an oil which crystallized. The crystalline product was recrystallized from ethanol and confirmed as the desired product by NMR, yield 5.4 grams, m.p. 75°-81° C.

Calculated: C, 78.75; H, 7.12; N, 14.13. Found: C, 77.27; H, 7.41; N, 13.72.

A small amount of material was recrystallized from ethanol a second time, m.p. 81°-83° C.

Found: C, 78.52; H, 6.92; N, 13.96.

An alternative procedure for obtaining the desired product was also followed as outlined below. Di-isopropylamine (2.58 grams) was added to a solution of 11.3 ml n-butyl lithium in 75 ml THF in a dry ice-acetone bath. After stirring about 10 minutes, acetonitrile (1.02 grams) in 25 ml THF was added keeping the temperature at about −70° C. The reaction mixture was stirred for about 40-50 minutes at −78° C. and then the vinamidine salt (7.5 grams) in 20 ml pyridine was added. The temperature was raised to −45° C. before the addition and was kept within the −45°−−40° C. range until after the addition was completed. Next, the reaction mixture was stirred at about −45° C. for 1 hour, allowed to warm to room temperature, and stirred for an additional 18 hours. The solvent was then removed leaving an oil which was dissolved in ethyl acetate. The organic layer was washed several times with water, then a saturated NaCl solution, and finally dried in vacuo leaving an oil which solidified. The solid product was recrystallized from ethanol, yield 1.5 grams, m.p. 77°–83° C.

EXAMPLE 15: 5-PHENYL-2-PYRIDYLAMINE

Ammonia was bubbled through 50 ml DMSO for about ½ hour and then 5-(dimethylamino)-4-phenyl-2,4-pentadienenitrile (3.0 grams) was added. The reaction mixture was gradually heated to 110° C., maintained at that temperature for about 42 hours, and then poured into ice water and extracted with ethyl acetate. Ether was used to break up the emulsion and then 2–3 chloroform extractions were carried out. Both fractions were dried in vacuo leaving 1.1 grams of crude semi-solid from the ether fraction and 2.3 grams of crude semi-solid from the chloroform fraction. Chromatographing the ether-extractible fraction over silica gel with ethyl acetate as the eluent yielded approximately 300 mg of final product, m.p. 129°–132° C.

Calculated: C, 77.62; H, 5.92; N, 16.46. Found: C, 77.38; H, 6.10; N, 16.25.

EXAMPLE 16: 1-(2,6-DICHLOROBENZOYL)-3-(5-PHENYL-2-PYRIDYL)UREA 2,6-Dichlorobenzoyl isocyanate (1.5 grams) in a small amount of dichloromethane was added to a solution of 5-phenyl-2-pyridylamine (1.0 gram) in 15 ml dichloromethane. After refluxing for about 5 minutes a precipitate formed. Following this, the reaction mixture was stirred at room temperature, cooled, and then the precipitate was filtered and recrystallized from ethanol, yield 1.8 grams. The identity of the final product was confirmed by NMR, m.p. 221°–231° C.

Calculated: C, 59.09; H, 3.39; N, 10.88. Found: C, 58.95; H, 3.47; N, 10.83.

EXAMPLE 17: 1-METHYL-2-PHENYLETHYLIDENE-PROPANEDINITRILE

Malononitrile (66 grams), phenylacetone (134 grams), ammonium acetate (8 grams), and 24 cc glacial acidic acid were refluxed in 400 ml benzene for about 2 hours. Water was added and then the benzene layer was washed several times, dried, and stripped in vacuo leaving an oil. TLC (ether) of the oily product showed one main spot with a few minor impurities. The identity of the oily product as the desired compound was confirmed by NMR analysis.

EXAMPLE 18: 3,3-DIETHOXY-1-METHYL-2-PHENYL-PROPYLIDENEPROPANEDINITRILE

1-Methyl-2-phenylethylidenepropanedinitrile (9 grams) was treated with 45 ml triethylorthoformate and 5 drops of boron trifluoride etherate in an oil bath at 140°–150° C. for about 18 hours. The reaction mixture was refluxed without a condenser for about 4 hours and then 10 ml. triethylorthoformate and several drops of boron trifluoride etherate were added. The mixture was heated again and then stripped and, after the addition of dichloromethane, restripped leaving a crude residue as the final product.

EXAMPLE 19: 3,3-DIMETHOXY-1-METHYL-2-PHENYL-PROPYLIDENEPROPANEDINITRILE

The desired product was prepared according to the teaching of Example 18 with the exception that trimethylorthoformate rather than triethylorthoformate was used as starting material.

EXAMPLE 20: MIXTURE OF 2-AMINO-4-METHYL-5-PHENYL-3-PYRIDINECARBONITRILE AND 2-AMINO-6-METHYL-5-PHENYL-3-PYRIDINECARBONITRILE

Ammonium hydroxide (40 ml) was added dropwise to 3,3-dimethoxy-1-methyl-2-phenylpropylidenepropanedinitrile (7 grams) in 350 ml THF at room temperature. After the reaction mixture was stirred for about 18 hours, 10 ml additional ammonium hydroxide was added. About 24 hours later, the mixture was stripped leaving a crude dark solid which was chromatographed on 300 ml silica gel using dichloromethane and dichloromethane/50% ethyl acetate as eluents. The crude product was then recrystallized from methanol to give grey needle-like crystals which were shown by NMR to be about 60% 4-methyl and about 40% 6-methyl isomer, yield 4.95 grams, m.p. 156°–159° C.

Calculated: C, 74.64; H, 5.26; N, 20.10. Found: C, 74.41; H, 5.23; N, 20.35.

EXAMPLE 21: MIXTURE OF 2-AMINO-4-METHYL-5-PHENYL-3-PYRIDINECARBONITRILE AND 2-AMINO-6-METHYL-5-PHENYL-3-PYRIDINECARBONITRILE (Alternate Procedure)

Ammonium hydroxide (20 ml) was added dropwise to a mixture of chromatographed 3,3-diethoxy-1-methyl-2-phenylpropylidenepropanedinitrile (4.1 grams) and 3,3-dimethoxy-1-methyl-2-phenylpropylidenepropanedinitrile (1.9 grams), prepared according to the teaching of Examples 18 and 19, in 100 ml THF at room temperature. The work-up procedure is taught in Example 20 and recrystallization from ethanol gave 2.4 grams, of the desired mixture, m.p. 157°–163° C.

EXAMPLE 22: MIXTURE OF 2-AMINO-4-METHYL-5-PHENYL-3-PYRIDINECARBOXYLIC ACID AND 2-AMINO-6-METHYL-5-PHENYL-3-PYRIDINECARBOXYLIC ACID

The mixture of Example 21 (2 grams) and KOH (2 grams) were heated in 90 ml ethylene glycol at 150°–160° C. for 2 hours. Additional KOH (3 grams) was added and the mixture was refluxed for another 2 hours. The reaction was then poured into water and neutralized to pH 4–5 to give 5.5 grams of grey solid in various fractions, m.p. 258°–272° C. dec. The crude product was resaponified with KOH (9 grams) in 90 ml ethylene glycol at 170° C. for 12 hours. The reaction mixture was then poured into water and neutralized to pH 7. A brownish solid formed which was filtered and confirmed as the desired product by NMR, yield 4.45 grams, m.p. 264°–270° C. dec.

EXAMPLE 23: MIXTURE OF 4-METHYL-5-PHENYL-2-PYRIDYL AMINE AND 6-METHYL-5-PHENYL-2-PYRIDYLAMINE AND THE SEPARATION THEREOF

The mixture of Example 22 (9.8 grams) and copper powder (2 grams) in 100 ml quinoline were heated in an oil bath at 255°–290° (mostly 260°–270° ) C. for about 3-4 hours until the reaction was complete. TLC (alumina-EtOAc/10% MeOH) showed two possible amine spots A and B. The reaction mixture was chromatographed on 600 ml of Woelm Grade 1 neutral alumina. Elution with ethyl acetate brought off the quinoline first, then spot A plus some impurity, and then spot B. Elution of spot B was completed with ethyl acetate-5–10% methanol. The spot B material was recrystallized from toluene-petroleum ether yielding tan crystals which were shown by NMR to be the desired 4-methyl product, yield 2.35 grams, m.p. 109°–113° C.

The spot A material was also recrystallized from toluene-petroleum ether and yielded tan needle-like crystals which were shown by NMR to be the desired 6-methyl product, yield 1.1 grams, m.p. 112°–116° C.

Calculated: C, 78.23; H, 6.57; N, 15.21. Found: C, 78.03; H, 6.37; N, 15.01.

EXAMPLE 24: 1-(2,6-DICHLOROBENZOYL)-3-(6-METHYL-5-PHENYL-2-PYRIDYL)UREA 2,6-Dichlorobenzoyl isocyanate (650 mg) was reacted with 6-methyl-5-phenyl-2-pyridylamine (500 mg) in 25 ml of ethyl acetate. A precipitate formed which was filtered and confirmed by NMR as the desired product, 219°–220° C.

Calculated: C, 60.02; H, 3.78; N, 10.50. Found: C, 59.77; H, 3.66; N, 10.42.

EXAMPLE 25: 1-(2,6-DICHLOROBENZOYL)-3-(4-METHYL-5-PHENYL-2-PYRIDYL)UREA 2,6-Dichlorobenzoyl isocyanate (1.4 grams) was reacted with 4-methyl-5-phenyl-2-pyridylamine (0.9 gram) in dichloromethane. There was an immediate exotherm and spontaneous reflux. The reaction mixture was then stirred at ambient temperature but no precipitate formed. After the mixture was stripped, the residue was recrystallized from ethanol yielding 1.0 gram of tan crystals, m.p. 210°–214° C. The identity of the desired product was confirmed by NMR.

Calculated: C, 60.02; H, 3.78; N, 10.50. Found: C, 60.22; H, 3.69; N, 10.21.

EXAMPLE 26: 3-PHENYLPENTANE-2,4-DIONE

Boron trifluoride-acetic acid (36%, 34.8 grams) was added with stirring dropwise to a solution of phenylacetone (4.46 grams), acetic anhydride, and para-toluenesulfonic acid (0.6 grams) in a water bath at room temperature. After stirring over night, a solid precipitate formed which was collected and washed with water and then refluxed in 100 ml water and sodium acetate (9.0 grams) for 2-3 hours. The original reaction mixture was also heated with 200 ml water and sodium acetate (13.5 grams) for the same period. Both mixtures were separately extracted with ether and then washed with saturated sodium bicarbonate solution to remove any acid. The ether portions were dried and then evaporated in vacuo leaving an oil which solidified, yield 1.4 grams, m.p. 40°–52° C.

EXAMPLE 27: 3-CYANO-4,6-DIMETHYL-5-PHENYL-2-PYRIDONE

3-Phenylpentane-2,4-dione (24.6 grams) was dissolved in about 50 ml ether and then added to a solution of sodium methoxide (7.8 grams) in 200 ml ether. A precipitate formed immediately which dissolved upon stirring after the addition of 100 ml water. The aqueous solution of 3-phenylpentane-2,4-dione sodium salt thus produced was treated with 2-cyanoacetamide, 2 ml acetic acid, 4.9 ml water, and sufficient piperidine to make the solution basic. After the reaction mixture was refluxed over night, an oily residue formed. Acetic acid was added to adjust the solution to pH 5, and after cooling, the water was decanted and ethanol added to give a collectible solid, yield 7.05 grams, m.p. 355°–368° C. dec.

Calculated: C, 74.98; H, 5.39; N, 12.49. Found: C, 72.18; H, 4.97; N, 11.82.

EXAMPLE 28: 2-CHLORO-4,6-DIMETHYL-5-PHENYL-3-PYRIDINECARBONITRILE

3-Cyano-4,6-dimethyl-5-phenyl-2-pyridone (7.0 grams) and phenylphosphonic dichloride (12.1 grams) were heated at 175°–180° C. for 2–3 hours. The solution was cooled, poured into ice water and made basic with ammonium hydroxide. A precipitate formed which was collected, air dried, and determined by NMR to be the desired product, yield 7.6 grams, m.p. 118°–123° C.

EXAMPLE 29: 2-AMINO-4,6-DIMETHYL-5-PHENYL-3-PYRIDINECARBONITRILE

2-Chloro-4,6-dimethyl-5-phenyl-3-pyridinecarbonitrile (8.3 grams) was dissolved in 110 ml DMSO and treated with gaseous $NH_3$ at a temperature of 100°–110° C. After about 66 hours of heating and treatment with $NH_3$, the reaction mixture was cooled and poured into ice water. A solid precipitate formed which was collected, washed with water, and then dried in an oven desicator. The identity of the desired product was confirmed by NMR.

EXAMPLE 30: 2-AMINO-4,6-DIMETHYL-5-PHENYL-3-PYRIDINECARBOXYLIC ACID

2-Amino-4,6-dimethyl-5-phenyl-3-pyridinecarbonitrile (0.5 gram) and potassium hydroxide (1.0 gram) were heated in 15 ml ethylene glycol at approximately 165° C. for about 6 hours. The reaction mixture was poured into ice water and then made acidic to a pH of 4–5. A solid formed which was collected, washed with water and identified as the desired product by TLC and NMR.

EXAMPLE 31: 4,6-DIMETHYL-5-PHENYL-2-PYRIDYLAMINE

2-Amino-4,6-dimethyl-5-phenyl-3-pyridinecarboxylic acid (6.1 grams) and copper powder (1.0 gram) were heated in 50 ml quinoline at 270°–290° C. for approximately 3 hours. The entire reaction mixture was then chromatographed over 600 ml of Grace 923 silica gel with ether followed by ethyl acetate, yield 3.0 grams of dried product, m.p. 105°–112° C.

Calculated: C, 78.75; H, 7.12; N, 14.13. Found: C, 78.59; H, 6.97; N, 13.93.

EXAMPLE 32:
1-(2-CHLOROBENZOYL)-3-(4,6-DIMETHYL-5-PHENYL-2-PYRIDYL)UREA 4,6-Dimethyl-5-phenyl-2-pyridylamine (0.5 gram) was dissolved in 25 ml acetonitrile and reacted with 2-chlorobenzoyl isocyanate (0.6 gram) under nitrogen at room temperature. A precipitate formed immediately and the reaction was stirred for approximately 2 hours. The solid product was collected, washed with a small amount of acetonitrile, and identified by NMR as the desired product, m.p. 176°-189° C.

Calculated: C, 66.40; H, 4.78; N, 11.06. Found: C, 66.68; H, 4.63; N, 11.20.

EXAMPLE 33:
γ-ACETYL-BENZENEBUTANENITRILE

Sodium (0.6 gram) was added to phenylacetone (120 grams) and the mixture was stirred at 95° C. until the sodium melted. The heat was then removed and the reaction allowed to proceed for an additional 5 minutes until all the sodium had dissolved. Next acrylonitrile (31.8 grams) was added dropwise at 80° C. over a 20-25 minute period with cooling to maintain the temperature. The reaction mixture was stirred for an additional 30 minutes, cooled with ice water, neutralized with 4 ml glacial acetic acid. After the addition of ether, the mixture was washed 5 times with water, dried with sodium sulfate and evaporated in vacuo. A yellow oil resulted which was distilled. At 115° C. and 0.50 mm the liquid began distilling consistently and several fractions were taken. The desired compound, confirmed by NMR, with a trace impurity was collected at b.p. 120°-122° C.

Calculated: C, 76.98; H, 7.00; N, 7.48. Found: C, 75.76; H, 6.89; N, 6.83.

EXAMPLE 34:
3,4-DIHYDRO-6-METHYL-5-PHENYL-2(1H)-PYRIDONE

At a temperature of about 0°-5° C. and with HCl gas slowly bubbling throughout, ethanol (1.5 grams) was added to a solution of γ-acetyl-benzenebutanenitrile (4.92 grams) and 150 ml ether. The reaction was kept dry and after approximately 3 hours of bubbling with HCl, the reaction mixture was allowed to stand for approximately 18 hours. The solvent was then removed in vacuo leaving an oil which partially solidified. After the addition of about 5 ml ethanol, a collectible water insoluble precipitate formed which was collected and triturated in acetone, yield 0.32 gram, m.p. 310°-330° C.

Calculated: C, 76.98; H, 7.00; N, 7.48. Found: C, 76.75; H, 6.78; N, 7.40.

EXAMPLE 35:
6-METHYL-5-PHENYL-2(1H)-PYRIDONE 3,4-Dihydro-6-methyl-5-phenyl-2(1H)-pyridone (25.6 grams) and 5% palladium/on carbon (4.9 grams) were refluxed for about 18 hours in 750 ml p-cymene. Since little product formed upon cooling, the reaction mixture was boiled and distilled until a constant temperature of 173° C. was reached. Refluxing continued for 36 hours and then the reaction mixture was filtered hot. Upon cooling, a solid precipitate formed which was collected and washed with ether, yield 13.0 grams, m.p. 201°-208° C.

EXAMPLE 36:
6-METHYL-5-PHENYL-2-PYRIDYLAMINE

A mixture of 6-methyl-5-phenyl-2-pyridone (12.0 grams) and phenylphosphorodiamidate (14.4 grams) in 300 ml diphenyl ether was heated for 19-20 hours at approximately 220°-225° [250]° C. After cooling, the reaction mixture was chromatographed over silica gel with ethyl acetate. A total of 0.8 gram, of desired product was collected and recrystallized from dichloromethane/petroleum ether, m.p. 110°-113° C.

Calculated: C, 78.23; H, 6.57; N, 15.21. Found: C, 78.46; H, 6.29; N, 15.07.

EXAMPLE 37:
γ-ACETYL-β-METHYLBENZENEBUTANENITRILE

Sodium (0.2 gram) was added to phenylacetone (40 grams) and the mixture was stirred at 95° C. until the sodium melted. The heat was then removed and the reaction allowed to proceed for an additional 5 minutes until all the sodium had dissolved. Next crotononitrile (13.4 grams) was added dropwise at 80° C. over a 20-25 minute period with cooling to maintain the temperature. The reaction mixture was then heated at 80°-85° C. for about 3-4 hours and then cooled and neutralized with a small amount of glacial acetic acid. After ether was added, the mixture was washed five times with water, dried with sodium sulfate, and evaporated in vacuo. A yellow oil formed which was distilled under vacuum. The desired product was distilled at 140°-142° C. and 0.5-0.6 mm, yield, 20.5 grams.

Calculated: C, 77.58; H, 7.51; N, 6.96. Found: C, 77.72; H, 7.28; N, 6.77.

EXAMPLE 38:
4,6-DIMETHYL-5-PHENYL-2-PYRIDYLAMINE

The conversion of γ-acetyl-β-methylbenzenebutanenitrile to the desired product is taught in Examples 34, 35, and 36.

EXAMPLE 39:
1-(2,6-DIFLUOROBENZOYL)-3-(6-METHYL-5-PHENYL-2-PYRIDYL)UREA

6-Methyl-5-phenyl-2-pyridylamine (500 mg) and 2,6-difluorobenzoyl isocyanate (650 mg) were reacted in 25 ml ethyl acetate. A precipitate formed which was filtered, dried, and identified as the desired product by NMR, m.p. 206°-208° C.

Calculated: C, 65.39; H, 4.12; N, 11.44. Found: C, 65.35; H, 3.87; N, 11.29.

EXAMPLE 40:
1-(2,6-DICHLOROBENZOYL)-3-(4,6-DIMETHYL-5-PHENYL-2-PYRIDYL)UREA 4,6-Dimethyl-5-phenyl-2-pyridylamine (500 mg) and 2,6-dichlorobenzoyl isocyanate (650 mg) were reacted in 25 ml ethyl acetate. A precipitate formed which was filtered, dried, and identified by NMR analysis as the desired product, m.p. 230°-235° C.

Calculated: C, 60.88; H, 4.14; N, 10.14. Found: C, 60.63; H, 4.03; N, 10.13.

EXAMPLE 41:
4-(4-CHLOROPHENYL)-2-CYANO-5-(DIMETHYLAMINO)-2,4-PENTADIENCARBOXYLIC ACID, ETHYL ESTER

Vinamidine salt (50.5 grams from Example 10) in 160 ml pyridine at below 0° C. in an ice-acetone bath, was treated with sodium ethoxide prepared by dissolving sodium (3.5 grams) in 160 ml ethanol at a temperature below 0° C. Ethylcyanoacetate (16.9 grams) was added dropwise with cooling so that the reaction temperature was kept below 5° C. After addition, the mixture was allowed to warm to room temperature and was stirred for about 18 hours. Next the solvent was removed in vacuo, chloroform was added, and the solution was washed several times with water. Upon drying, the solvent was removed and the solid material remaining was recrystallized from ethanol, yield 27.5 grams, m.p. 168°–170° C. TLC (ether) showed one yellow spot with traces of material at the origin. A small sample of final product (380 mg) was recrystallized a second time, m.p. 168°–170° C.

Calculated: C, 63.05; H, 5.62; N, 9.19. Found: C, 62.83; H, 5.38; N, 9.27.

EXAMPLE 42:
2-AMINO-5-(4-CHLOROPHENYL)-3-PYRIDINECARBOXYLIC ACID, ETHYL ESTER-1-OXIDE 4-(4-Chlorophenyl)-2-cyano-5-(dimethylamino)-2,4-pentadiencarboxylic acid, ethyl ester (3.04 grams) and hydroxylamine HCl (1.04 grams) in 20 ml pyridine was stirred 18 hours at 20°–25° C. The reaction mixture was then poured into water and quickly precipitated. After collection and washing with water, the solid product was recrystallized from ethanol, yield 2.6 grams, m.p. 141°–153° C.

Calculated: C, 57.44; H, 4.48; N, 9.57. Found: C, 57.68; H, 4.51; N, 9.72.

EXAMPLE 43:
6-CHLORO-5-(4-CHLOROPHENYL)-2-FORMAMIDO-3-PYRIDINECARBOXYLIC ACID, ETHYL ESTER 23.8 ml DMF (dry) was added dropwise to 114 ml $POCl_3$ with cooling so that the temperature was 40° C. or below. 2-Amino-5-(4-chlorophenyl)-3-pyridinecarboxylic acid, ethyl ester-1-oxide (23.8 grams) was added mainly in one addition. The temperature quickly rose to reflux and after 15–25 minutes, the reaction was cooled and then the $POCl_3$ was removed. The remaining oil was poured into ice water and dichloromethane was added. Next the organic layer was washed numerous times with a saturated solution of sodium bicarbonate and then dried and stripped in vacuo leaving an oil which solidified. TLC ($CH_2Cl_2$) showed mostly the desired product although some impurities were also present. The solid product was fairly soluble in $CH_2Cl_2$ and was chromatographed on Wolem silica gel with dichloromethane (about 6–7 gallons $CH_2Cl_2$ was necessary), yield 13.4 grams, m.p. 184°–187° C.

EXAMPLE 44:
2-AMINO-6-CHLORO-5-(4-CHLOROPHENYL)-3-PYRIDINECARBOXYLIC ACID, ETHYL ESTER

6-Chloro-5-(4-chlorophenyl)-2-formamido-3-pyridinecarboxylic acid, ethyl ester (0.5 gram) was partially dissolved in 50 ml ethanol and treated with about 5–6 drops concentrated HCl. The reaction mixture was refluxed for approximately 3 hours, and upon cooling, a solid precipitate was collected, yield 350 mg, m.p. 195°–198° C.

Calculated: C, 54.04; H, 3.89; N, 9.00. Found: C, 54.26; H, 3.80; N, 9.29.

EXAMPLE 45:
2-AMINO-6-CHLORO-5-(4-CHLOROPHENYL)-3-PYRIDINECARBOXYLIC ACID

2-Amino-6-chloro-5-(4-chlorophenyl)-3-pyridinecarboxylic acid, ethyl ester (0.3 gram) was partially dissolved in 3 ml water and 3 ml dioxane and then 0.2 gram of sodium hydroxide was added. The reaction mixture was refluxed for 1½–2 hours and, after the mixture was neutralized with glacial acetic acid, a precipitate formed which was collected and washed with water, yield approximately 250 mg, m.p. 280°–284° C. dec.

Calculated: C, 50.91; H, 2.85; N, 9.89. Found: C, 48.86; H, 2.60; N, 9.38.

EXAMPLE 46:
6-CHLORO-5-(4-CHLOROPHENYL)-2-PYRIDYLAMINE

2-Amino-6-chloro-5-(4-chlorophenyl)-3-pyridinecarboxylic acid (9 grams), 300 ml $H_2SO_4$, and 90 ml water were heated in an oil bath at 220°–230° C. for 1 hour. The reaction mixture was diluted to 2 liters, cooled, and neutralized with 50% NaOH. A gum-like solid formed which was only partially removed by filtration. The filtrate was then extracted four times with 800–1000 ml portions of $CH_2Cl_2$ taking care not to remove any of gum-like solid. The combined $CH_2Cl_2$ layers were dried over $MgSO_4$. The filtered solid was dissolved in ethyl acetate and then the aqueous-solid mixture was extracted with the same solvent. TLC of this extract showed the desired product and an impurity. Next the $CH_2Cl_2$ extracts were filtered and stripped to give about 0.6 gram of the desired product, m.p. 178°–182° C. The ethyl acetate extract was similarly treated to give a solid residue. Trituration of this solid with hot $CH_2Cl_2$ followed by filtration and stripping gave about 0.8 gram of the desired product, m.p. 179°–183° C.

EXAMPLE 47:
1-(2,6-DIFLUOROBENZOYL)-3-(6-CHLORO-5-(4-CHLOROPHENYL)-2-PYRIDYL)UREA

6-Chloro-5-(4-chlorophenyl)-2-pyridylamine (0.3 gram) was dissolved in 25 ml acetonitrile and treated with 2,6-difluorobenzoyl isocyanate (0.5 gram) under nitrogen at room temperature. A precipitate formed almost immediately and after about three hours stirring, the solid was collected and washed with acetonitrile, yield 0.36 gram, m.p. 237°–241° C.

Calculated: C, 54.05; H, 2.63; N, 9.95. Found: C, 54.26; H, 2.67; N, 10.15.

EXAMPLE 48:
6-(4-CHLOROPHENYL)-3-CYANO-2-PYRIDONE

A mixture of 4-chloroacetophenone (100 grams) and ethyl formate (48 grams) was added dropwise over a 3 hour period to a well stirred cold suspension of sodium methylate in 540 ml anhydrous ether. The addition was carried out in an ice bath to prevent the temperature from exceeding 3° C. After the addition was complete, the ice bath was removed and the reaction mixture was stirred for about 18 hours at room temperature. Next the suspension of benzoylacetaldehyde sodium salt was extracted with 400 ml water and separated. Cyanoacetamide (54.5 grams) and a solution of 9 ml acetic acid, 22 ml water, and sufficient piperidine were added to give an alkaline reaction to pH paper. The reaction mixture was refluxed for 2 hours, acidified to approximately pH 5 with acetic acid, and thoroughly chilled. The solid which formed was then heated twice in refluxing ethanol and the insoluble material was collected each time. This solid insoluble material was shown by NMR to be the desired product and was used without further purification, m.p. 330°–339° C.

Calculation: C, 62.49; H, 3.06; N, 12.15. Found: C, 63.63; H, 3.57; N, 12.68.

EXAMPLE 49:
2-CHLORO-6-(4-CHLOROPHENYL)-3-PYRIDINECARBONITRILE 6-(4-Chlorophenyl)-3-cyano-2-pyridone (42 grams) and phenylphosphonic dichloride were heated for 2.5 hours at 175°–180° C. taking precautions to keep the reaction dry. Upon cooling, the reaction mixture was poured into 500 ml of ice water and was made slightly alkaline by the addition of concentrated NH$_4$OH. A solid product formed which was thoroughly washed with water and recrystallized from ethanol/DMF, yield 42 grams, m.p. 179°–181° C.

Calculated: C, 57.86; H, 2.43; N, 11.25. Found: C, 57.91; H, 2.59; N, 11.32.

EXAMPLE 50:
6-(4-CHLOROPHENYL)-3-PYRIDINE CARBONITRILE

2-Chloro-6-(4-chlorophenyl)-3-pyridinecarbonitrile (2.49 grams) and 5% Pd/C (0.3 gram) were reacted on a Parr shaker in 100 ml DMF. Next the reaction mixture was filtered and the filtrate poured into ice water. A solid formed which was collected and recrystallized from ethanol, yield 0.85 gram.

EXAMPLE 51:
6-(4-CHLOROPHENYL)-3-PYRIDINECARBOXAMIDE 6-(4-Chlorophenyl)-3-pyridinecarbonitrile (1.61 grams), 30% hydrogen peroxide (3.0 cc.), 6 N sodium hydroxide (0.3 cc.), and about 6 ml ethanol were placed in a reaction vessel and cooled slightly. The reaction temperature rose to about 50° C. and the mixture was stirred for about 1 hour. After the reaction had cooled, a solid precipitate formed and was collected by filtration. As indicated by TLC, pure product was obtained by heating the solid in refluxing acetone, yield 0.4 gram, m.p. 245°–258° C.

EXAMPLE 52:
6-(4-CHLOROPHENYL)-3-PYRIDYLAMINE

Bromine (2.14 grams) was added dropwise to a solution (ice cold) of NaOH (2.68 grams) in 32 ml of water. A paste, comprised of 6-(4-chlorophenyl)-3-pyridinecarboxamide and water, was added in portions while maintaining a temperature of about 0° C. After stirring for 30 minutes, the reaction mixture was warmed to ambient temperature and then slowly heated to 75°–80° C. and maintained at that temperature for 1 hour. A dark precipitate formed which was filtered. The solid thus formed was dissolved in ether and the insoluble materials were removed by filtration. The ether portion was dried and then evaporated in vacuo leaving an oily residue. The material showed several spots when chromatographed over silica gel with ethyl acetate. Both IR and NMR analysis confirmed that the middle and most significant spot was the desired product, yield 180–190 mg.

EXAMPLE 53:
1-(2,6-DICHLORBENZOYL)-3-(6-(4-CHLOROPHENYL)-3-PYRIDYL)UREA 6-(4-Chlorophenyl)-3-pyridylamine (70 mg) was dissolved in 45 ml acetonitrile and treated with 2,6-dichlorobenzoyl isocyanate (0.25 gram) under nitrogen at room temperature. A precipitate formed almost immediately and after about 2 hours stirring, the solid was collected and recrystallized from ethanol, yield, 200 mg, m.p. 225°–229° C. The identity of the product was confirmed by NMR.

Calculated: C, 54.25; H, 2.88; N, 9.99. Found: C, 54.97; H, 3.19; N, 10.63.

EXAMPLE 54:
3-CYANO-5-METHYL-6-PHENYLPYRIDONE

The compound is prepared according to the teaching of Example 48 with the exception that propiophenone rather than 4-chloroacetophenone is used as starting material. The final product was recrystallized from acetone, m.p. 250°–257° C.

Calculated: C, 74.27; H, 4.79; N, 13.33. Found: C, 74.16; H, 4.58; N, 13.59.

EXAMPLE 55:
2-CHLORO-5-METHYL-6-PHENYL-3-PYRIDINECARBONITRILE

The desired product was prepared according to the teaching of Example 49. The identity of the desired product was confirmed by NMR analysis.

EXAMPLE 56:
5-METHYL-6-PHENYL-3-PYRIDINECARBONITRILE

The desired product was prepared according to the teaching of Example 50. The identity of the final product was confirmed by NMR analysis.

EXAMPLE 57:
5-METHYL-6-PHENYL-3-PYRIDINECARBOXAMIDE

The desired product was prepared according to the teaching of Example 51. The identity of the final product was confirmed by NMR analysis.

EXAMPLE 58:
5-METHYL-6-PHENYL-3-PYRIDYLAMINE

The desired product was prepared according to the teaching of Example 52. The final product was recrystallized from dichloromethane, petroleum ether, m.p. 93°–98° C.

EXAMPLE 59:
1-(2,6-DICHLOROBENZOYL)-3-(5-METHYL-6-PHENYL-3-PYRIDYL)UREA

5-Methyl-6-phenyl-3-pyridylamine (0.4 gram) in 20 ml of acetonitrile was added to 2,6-dichlorobenzoyl isocyanate (0.5 gram) under nitrogen and at room temperature. After about 10–20 minutes a precipitate formed. The reaction mixture was then stirred for about 4–5 hours and the product was filtered and washed with acetonitrile, yield, 580 mg; m.p. 202°–205° C. A small portion of the product was recrystallized from ethanol, m.p. 204°–209° C.

Calculated: C, 60.02; H, 3.78; N, 10.50. Found: C, 59.77; H, 3.82; N, 10.61.

EXAMPLE 60:
5-(4-CHLOROPHENYL)-2-PYRIDYLAMINE-1-OXIDE 5-(4-Chlorophenyl)-2-pyridylamine (1.5 grams—prepared according to the teaching of Examples 1–6) in 30 ml acetone was added to a solution of 85% MCPB (1.7 grams) in 30 ml acetone. After about 5 minutes a precipitate formed and after an additional 2 hours, the reaction mixture was chilled in a refrigerator for about 18 hours. The mixture was then filtered to give 2.1 grams of solid material which was suspended in 200 ml chloroform and stirred with solid $K_2CO_3$. Water (40 ml) was added to dissolve the solid and then the aqueous layer was extracted. Four additional extractions with 1–200 ml chloroform were carried out to remove all the product. After drying and stripping, a yellowish solid was obtained which was shown by NMR to be the desired product, yield 1.2 grams, m.p. 224°–226° C.

EXAMPLE 61:
1-(2,6-DICHLOROBENZOYL)-3-(5-(4-CHLOROPHENYL)-2-PYRIDYL-1-OXIDE)UREA 2,6-Dichlorobenzoyl isocyanate (0.7 gram) in dichloromethane was added to a solution-suspension of 5-(4-chlorophenyl)-2-pyridylamine-1-oxide (0.5 gram) in 25 ml dichloromethane. A precipitate formed almost immediately. The reaction mixture was stirred for about 3 days at room temperature and, after cooling, the precipitate was filtered to give 510 mg of the desired compound, m.p. 235°–237° dec.

Calculated: C, 52.26; H, 2.77; N, 9.62. Found: C, 52.50; H, 2.69; N, 9.67.

EXAMPLE 62:
4-DIMETHYLAMINO-3-PHENYL-3-BUTENE-2-ONE

A mixture of phenylacetone (13.4 grams) and dimethylformamide dimethylacetal (13.0 grams) was heated at 90°–95° C. on a steam bath for about 2½ hours. A crude oil was produced which was then chromatographed on 600 ml of silica gel using ethyl acetate as an eluent. The final product, whose structure was confirmed by NMR, was a yellow oil which crystallized upon standing, yield 15.5 grams.

EXAMPLE 63:
3-CYANO-6-METHYL-5-PHENYL-2-PYRIDONE

A mixture of 4-dimethylamino-3-phenyl-3-butene-2-one (14.1 grams) and cyanoacetamide (5.9 grams) in 100 ml methanol was added to sodium methoxide (7.9 grams) in 100 ml methanol. The mixture was refluxed for 18 hours and then the crude reaction was stripped and the residue dissolved in a small amount of hot water. Acidification to pH 6–7 gave a gum-like solid which was collected by filtration. Further acidification to a lower pH gave only an oil. Trituration of the gum with ethyl acetate and chilling resulted in an off-white solid which was identified by NMR as the desired product, yield 2.8 grams, m.p. 280°–290° C.

EXAMPLE 64:
2-AMINO-6-METHYL-5-PHENYL-3-PYRIDINECARBONITRILE

The 3-cyano-6-methyl-5-phenyl-2-pyridone obtained in Example 63 was converted to the desired product according to the teaching of Examples 3 and 4. The structure of the final product was confirmed by NMR, m.p. 182°–189° C.

EXAMPLE 65:
2-AMINO-6-METHYL-5-PHENYL-3-PYRIDINECARBOXYLIC ACID

This product was prepared according to the teaching of Example 5. The structure of the final product was confirmed by NMR, m.p. 300°–308° C. dec.

EXAMPLE 66:
6-METHYL-5-PHENYL-2-PYRIDYLAMINE

This product was prepared according to the teaching of Example 6 (Example 23 represents an alternative teaching). The structure of the final product was confirmed by NMR.

EXAMPLE 67:
1-(2-BROMOBENZOYL)-3-(6-METHYL-5-PHENYL-2-PYRIDYL)UREA

2-Bromobenzoyl isocyanate (650 mg) is reacted with 6-methyl-5-phenyl-2-pyridylamine (500 mg) in 25 ml of ethyl acetate. A precipitate forms which upon filtering constitutes the desired product.

EXAMPLE 68:
4-CHLORO-γ-(1-OXOETHYL)-β-METHYLBENZENEBUTANENITRILE

Triton B (5.85 ml) was added dropwise to 4-chlorophenylacetone (21.8 grams) in 78 ml of tert. butanol. Next crotononitrile (9.17 grams) was likewise added with initial cooling to lower the temperature to about 20° C. Since the reaction was not exothermic, no additional cooling was necessary after the desired temperature was reached. The reaction was then heated to 65° C. for 2½ hours and, after chilling in an ice bath, 262 ml of 1 N HCl was added in portions. Next the reaction mixture was extracted with ether, washed with water, dried, and evaporated in vacuo. An oil resulted which was distilled under vacuum, yield 18.6 grams, b.p. 130°–131° C.

EXAMPLE 69:
4-CHLORO-γ-[1-(METHOXYIMINO)ETHYL]-β-METHYLBENZENEBUTANENITRILE

4-Chloro-γ-(1-oxoethyl)-β-methylbenzenebutanenitrile (4.4 grams) and methoxyamine.HCl (3.7 grams) in 80 ml of pyridine were stirred at ambient temperature. The mixture was then poured into ice containing sufficient concentrated HCl to neutralize the pyridine, stirred, and extracted with dichloromethane. The resulting dichloromethane solution was washed with water and a saturated solution of sodium chloride and was then dried over magnesium sulfate. Filtering and stripping resulted in a clear colorless gum which was shown by NMR and IR to be the desired product.

Calculated: C, 63.51; H, 6.47; N, 10.58; Found: C, 63.80; H, 6.19; N, 10.63.

EXAMPLE 70:
5-(4-CHLOROPHENYL)-4,6-DIMETHYL-2-PYRIDYLAMINE

Methane sulfonic acid (19.5 grams) in 500 ml of chlorobenzene was distilled slowly through a short distillation head with a drying tube until the distillate was clear of any heterogeneity and until the boiling point reached 130°–131° C. Over the next 30 minutes 4-chloro-γ-[1-(methoxyimino)ethyl]-β-methylbenzenebutanenitrile (25 grams) in 150 ml of chlorobenzene was added dropwise while the mixture was being slowly distilled and magnetically stirred. The reaction mixture was then refluxed for about 18 hours and then cooled, diluted with dichloromethane, and washed with 100 ml of sodium hydroxide, water, and then a saturated solution of sodium chloride. After drying over magnesium sulfate, the crude material was chromatographed on silica gel using 1 liter each of dichloromethane, 1% and 2% methanol, and 2.5 liters of 5% methanol, to yield 8.1 grams of the pure desired product. The identity of the final product was confirmed by NMR, m.p. 148°–152° C.

EXAMPLE 71:
1-(2,6-DIFLUOROBENZOYL)-3-(5-(4-CHLOROPHENYL)-4,6-DIMETHYL-2-PYRIDYL)UREA 4,6-Dimethyl-5-(4-chlorophenyl)-2-pyridylamine (500 mg) and 2,6-fluorobenzoyl isocyanate (650 mg) were reacted in 25 ml dichloromethane. A precipitate formed which was filtered, dried, and identified by NMR analysis as the desired product, m,p, 204°–206° C.

Calculated: C, 60.66; H, 3.88; N, 10.11. Found: C, 60.54; H, 3.85; N, 9.86.

Other representative examples synthesized in accordance with the foregoing teaching include the following.

| EXAMPLE NO. | COMPOUND NAME | MELTING POINT |
|---|---|---|
| 72 | 1-(2-chlorobenzoyl)-3-(5-phenyl-2-pyridyl)urea | 205–207° C. |
| 73 | 1-(2-chloro-6-fluorobenzoyl)-3-(5-(4-chlorophenyl)-2-pyridyl)urea | 211–221° C. |
| 74 | 1-(2-methylbenzoyl)-3-(5-(4-chlorophenyl)-2-pyridyl)urea | 233–235° C. |
| 75 | 1-(2-chloro-6-methoxybenzoyl)-3-(5-(4-chlorophenyl)-2-pyridyl)urea | 212–221° C. |
| 76 | 1-(2,6-dichlorobenzoyl)-3-(5-(3-chlorophenyl)-2-pyridyl)urea | 211–216° C. |
| 77 | 1-(2,6-difluorobenzoyl)-3-(5-(3,4-dichlorophenyl)-2-pyridyl)urea | |
| 78 | 1-(2,6-dichlorobenzoyl)-3-(5-(4-bromophenyl)-2-pyridyl)urea | 231–234° C. |
| 79 | 1-(2-chlorobenzoyl)-3-(5-(4-bromophenyl)-2-pyridyl)urea | 228–230° C. |
| 80 | 1-(2,6-dimethoxybenzoyl)-3-(5-(4-bromophenyl)-2-pyridyl)urea | 221–228° C. |
| 81 | 1-(2,6-dichlorobenzoyl)-3-(5-(4-tolyl)-2-pyridyl)urea | 230–234° C. |
| 82 | 1-(2,6-dimethoxybenzoyl)-3-(5-(4-tolyl)-2-pyridyl)urea | 197–199° C. |
| 83 | 1-(2,6-dichlorobenzoyl)-3-(5-(3-(trifluoromethyl)phenyl)-2-pyridyl)urea | 192–194° C. |
| 84 | 1-(2-chlorobenzoyl)-3-(5-(3-(trifluoromethyl)phenyl)-2-pyridyl)urea | 207–209° C. |
| 85 | 1-(2,6-dimethoxybenzoyl)-3-(5-(3-(trifluoromethyl)phenyl)-2-pyridyl)urea | 198–206° C. |
| 86 | 1-(2,6-difluorobenzoyl)-3-(5-(3-(trifluoromethyl)phenyl)-2-pyridyl)urea | 225–227° C. |
| 87 | 1-(2,6-dichlorobenzoyl)-3-(5-(4-methoxyphenyl)-2-pyridyl)urea | 233–237° C. |
| 88 | 1-(2,6-dichlorobenzoyl)-3-(5-(2,4-dichlorophenyl)-2-pyridyl)urea | 214–224° C. |
| 89 | 1-(2-chlorobenzoyl)-3-(5-(2,4-dichlorophenyl)-2-pyridyl)urea | 232–235° C. |
| 90 | 1-(2,6-dichlorobenzoyl)-3-(5-(3,4-dichlorophenyl)-2-pyridyl)urea | 226–228° C. |
| 91 | 1-(2,6-dichlorobenzoyl)-3-(5-(3,4-dimethoxyphenyl)-2-pyridyl)urea | 201–205° C. |
| 92 | 1-(2-chlorobenzoyl)-3-(5-(3,4-dimethoxyphenyl)-2-pyridyl)urea | 198–201° C. |
| 93 | 1-(2,6-difluorobenzoyl)-3-(4-methyl-5-phenyl-2-pyridyl)urea | 219–224° C. |
| 94 | 1-(2,6-dichlorobenzoyl)-3-(5-(4-chlorophenyl)-4-methyl-2-pyridyl)urea | 226–233° C. |
| 95 | 1-(2-chlorobenzoyl)-3-(5-(4-chlorophenyl)-4-methyl-2-pyridyl)urea | 212–217° C. |
| 96 | 1-(2,6-difluorobenzoyl)-3-(5-(4-chlorophenyl)-4-methyl-2-pyridyl)urea | 205–211° C. |
| 97 | 1-(2-chloro-6-fluorobenzoyl)-3-(5-(4-chlorophenyl)-4-methyl-2-pyridyl)urea | 209–215° C. |
| 98 | 1-(2-chlorobenzoyl)-3-(5-(4-bromophenyl)-4-methyl-2-pyridyl)urea | 210–216° C. |
| 99 | 1-(2,6-difluorobenzoyl)-3-(5-(4-bromophenyl)-4-methyl-2-pyridyl)urea | 245–248° C. |
| 100 | 1-(2,6-dichlorobenzoyl)-3-(4-methyl-5-(4-tolyl)-2-pyridyl)urea | 208–211° C. |
| 101 | 1-(2-chlorobenzoyl)-3-(4-methyl-5-(4-tolyl)-2-pyridyl)urea | 180–185° C. |
| 102 | 1-(2,6-difluorobenzoyl)-3-(4-methyl-5-(4-tolyl)-2-pyridyl)urea | 208–211° C. |
| 103 | 1-(2-chlorobenzoyl)-3-(5-(3-chlorophenyl)-4-methyl-2-pyridyl)urea | 206–211° C. |
| 104 | 1-(2,6-difluorobenzoyl)-3-(5-(3-chlorophenyl)-4-methyl-2-pyridyl)urea | 191–204° C. |
| 105 | 1-(2-chlorobenzoyl)-3-(6-methyl-5-phenyl-2-pyridyl)urea | 213–216° C. |
| 106 | 1-(2,6-dimethoxybenzoyl)-3-(6-methyl-5-phenyl-2-pyridyl)urea | 188–197° C. |
| 107 | 1-(2-methylbenzoyl)-3-(6-methyl-5-phenyl-2-pyridyl)urea | 221–222° C. |
| 108 | 1-(2,6-dichlorobenzoyl)-3-(5-(4-chlorophenyl)-6-methyl-2-pyridyl)urea | 225–228° C. |
| 109 | 1-(2-chlorobenzoyl)-3-(5-(4-chlorophenyl)-6-methyl-2-pyridyl)urea | 223–225° C. |
| 110 | 1-(2,6-dimethoxybenzoyl)-3-(5-(4-chlorophenyl)-6-methyl-2-pyridyl)urea | 219–222° C. |
| 111 | 1-(2,6-difluorobenzoyl)-3-(5-(4-chlorophenyl)-6-methyl-2-pyridyl)urea | 218–221° C. |
| 112 | 1-(2-fluoro-6-chlorobenzoyl)-3-(5-(4-chlorophenyl)-6-methyl-2-pyridyl)urea | 226–231° C. |
| 113 | 1-(2-chloro-6-methoxybenzoyl)-3-(5-(4-chlorophenyl)-6-methyl-2-pyridyl)urea | 225–230° C. |
| 114 | 1-(2-methylbenzoyl)-3-(5-(4-chlorophenyl)-6-methyl-2-pyridyl)urea | 231–236° C. |
| 115 | 1-(2,6-dichlorobenzoyl)-3-(5-(4-methoxyphenyl)-6-methyl-2-pyridyl)urea | 216–220° C. |

-continued

| EXAMPLE NO. | COMPOUND NAME | MELTING POINT |
|---|---|---|
| 116 | 1-(2-chlorobenzoyl)-3-(5-(4-methoxyphenyl)-6-methyl-2-pyridyl)urea | 239–241° C. |
| 117 | 1-(2,6-dimethoxybenzoyl)-3-(5-(4-methoxyphenyl)-6-methyl-2-pyridyl)urea | 203–206° C. |
| 118 | 1-(2,6-difluorobenzoyl)-3-(5-(4-methoxyphenyl)-6-methyl-2-pyridyl)urea | 236–240° C. |
| 119 | 1-(2-methylbenzoyl)-3-(5-(4-methoxyphenyl)-6-methyl-2-pyridyl)urea | 225–229° C. |
| 120 | 1-(2,6-dimethylbenzoyl)-3-(5-(4-methoxyphenyl)-6-methyl-2-pyridyl)urea | 218–221° C. |
| 121 | 1-(2,6-dichlorobenzoyl)-3-(6-methyl-5-(4-tolyl)-2-pyridyl)urea | 203–204° C. |
| 122 | 1-(2-chlorobenzoyl)-3-(6-methyl-5-(4-tolyl)-2-pyridyl)urea | 221–223° C. |
| 123 | 1-(2,6-dimethoxybenzoyl)-3-(6-methyl-5-(4-tolyl)-2-pyridyl)urea | 203–207° C. |
| 124 | 1-(2,6-difluorobenzoyl)-3-(6-methyl-5-(4-tolyl)-2-pyridyl)urea | 223–226° C. |
| 125 | 1-(2,6-dimethylbenzoyl)-3-(6-methyl-5-(4-tolyl)-2-pyridyl)urea | 213–216° C. |
| 126 | 1-(2-chlorobenzoyl)-3-(5-(4-bromophenyl)-6-methyl-2-pyridyl)urea | 238–233° C. |
| 127 | 1-(2,6-difluorobenzoyl)-3-(5-(4-bromophenyl)-6-methyl-2-pyridyl)urea | |
| 128 | 1-(2,6-difluorobenzoyl)-3-(6-methyl-5-(3-chlorophenyl)-2-pyridyl)urea | 194–197° C. |
| 129 | 1-(2-chlorobenzoyl)-3-(6-chloro-5-(4-chlorophenyl)-2-pyridyl)urea | 240–243° C. |
| 130 | 1-(2,6-difluorobenzoyl)-3-(6-chloro-5-(4-chlorophenyl)-2-pyridyl)urea | 237–241° C. |
| 131 | 1-(2-chloro-6-fluorobenzoyl)-3-(6-chloro-5-(4-chlorophenyl)-2-pyridyl)urea | 215–221° C. |
| 132 | 1-(2,6-difluorobenzoyl)-3-(4,6-dimethyl-5-phenyl-2-pyridyl)urea | 215–218° C. |
| 133 | 1-(2-methylbenzoyl)-3-(4,6-dimethyl-5-phenyl-2-pyridyl)urea | 216–222° C. |
| 134 | 1-(2-chloro-6-fluorobenzoyl)-3-(5-(4-chlorophenyl)-4,6-dimethyl-2-pyridyl)urea | 222–225° C. |
| 135 | 1-(2-chlorobenzoyl)-3-(5-(4-chlorophenyl)-4,6-dimethyl-2-pyridyl)urea | 209–213° C. |
| 136 | 1-(2,6-dichlorobenzoyl)-3-(6-phenyl-3-pyridyl)urea | 209–216° C. |
| 137 | 1-(2-chlorobenzoyl)-3-(6-phenyl-3-pyridyl)urea | 184–194° C. |
| 138 | 1-(2,6-dimethoxybenzoyl)-3-(6-phenyl-3-pyridyl)urea | 210–213° C. |
| 139 | 1-(2-chlorobenzoyl)-3-(6-(4-chlorophenyl)-3-pyridyl)urea | 214–219° C. |
| 140 | 1-(2,6-dimethoxybenzoyl)-3-(6-(4-chlorophenyl)-3-pyridyl)urea | 214–219° C. |
| 141 | 1-(2,6-difluorobenzoyl)-3-(6-(4-chlorophenyl)-3-pyridyl)urea | 246–252° C. |
| 142 | 1-(2,6-dichlorobenzoyl)-3-(6-(3-chlorophenyl)-3-pyridyl)urea | 217–220° C. |
| 143 | 1-(2,6-dimethoxybenzoyl)-3-(6-(3-chlorophenyl)-3-pyridyl)urea | 191–194° C. |
| 144 | 1-(2,6-dichlorobenzoyl)-3-(6-(3-(trifluoromethyl)phenyl)-3-pyridyl)urea | 201–208° C. |
| 145 | 1-(2-chlorobenzoyl)-3-(6-(3-(trifluoromethyl)phenyl)-3-pyridyl)urea | 196–199° C. |
| 146 | 1-(2,6-dimethoxybenzoyl)-3-(6-(3-(trifluoromethyl)phenyl)-3-pyridyl)urea | 185–188° C. |
| 147 | 1-(2,6-dichlorobenzoyl)-3-(6-(4-tolyl)-3-pyridyl)urea | 220–223° C. |
| 148 | 1-(2-chlorobenzoyl)-3-(6-(4-tolyl)-3-pyridyl)urea | 206–210° C. |
| 149 | 1-(2,6-dimethoxybenzoyl)-3-(6-(4-tolyl)-3-pyridyl)urea | 224–227° C. |
| 150 | 1-(2,6-dichlorobenzoyl)-3-(6-(4-methoxyphenyl)-3-pyridyl)urea | 203–205° C. |
| 151 | 1-(2-chlorobenzoyl)-3-(6-(4-methoxyphenyl)-3-pyridyl)urea | 210–213° C. |
| 152 | 1-(2,6-dimethoxybenzoyl)-3-(6-(4-methoxyphenyl)-3-pyridyl)urea | 203–206° C. |
| 153 | 1-(2-chlorobenzoyl)-3-(5-methyl-6-phenyl-3-pyridyl)urea | 160–161° C. |
| 154 | 1-(2,6-dimethoxybenzoyl)-3-(5-methyl-6-phenyl-3-pyridyl)urea | 200–205° C. |
| 155 | 1-(2,6-difluorobenzoyl)-3-(5-methyl-6-phenyl-3-pyridyl)urea | 204–208° C. |
| 156 | 1-(2,6-dichlorobenzoyl)-3-(6-(4-chlorophenyl)-5-methyl-3-pyridyl)urea | 178–191° C. |
| 157 | 1-(2-chlorobenzoyl)-3-(6-(4-chlorophenyl)-5-methyl-3-pyridyl)urea | 165–188° C. |
| 158 | 1-(2,6-dimethoxybenzoyl)-3-(6-(4-chlorophenyl)-5-methyl-3-pyridyl)urea | 173–177° C. |
| 159 | 1-(2-difluorobenzoyl)-3-(5-(4-bromophenyl)-4,6-dimethyl-2-pyridyl)urea | 210–212° C. |
| 160 | 1-(2-chloro-6-fluorobenzoyl)-3-(5-(4-bromophenyl)-4,6-dimethyl-2-pyridyl)urea | 227–232° C. |
| 161 | 1-(2-chlorobenzoyl)-3-(5-(4-bromophenyl)-4,6-dimethyl-2-pyridyl)urea | 216–224° C. |
| 162 | 1-(2,6-dichlorobenzoyl)-3-(5-(4-bromophenyl)-4,6-dimethyl-2-pyridyl)urea | 207–220° C. |
| 163 | 1-(2-bromobenzoyl)-3-(5-(4-bromophenyl)-4,6-dimethyl-2-pyridyl)urea | |
| 164 | 1-(2-fluoro-6-methoxybenzoyl)-3-(5-(4-bromophenyl)-4,6-dimethyl-2-pyridyl)urea | |
| 165 | 1-(2-chloro-6-methoxybenzoyl)-3-(5-(4-bromophenyl)-4,6-dimethyl-2-pyridyl)urea | |
| 166 | 1-(2,6-dimethylbenzoyl)-3-(5-(4-bromophenyl)-4,6-dimethyl-2-pyridyl)urea | |
| 167 | 1-(2-methylbenzoyl)-3-(5-(4-bromophenyl)-4,6-dimethyl-2-pyridyl)urea | |
| 168 | 1-(2,6-dimethoxybenzoyl)-3-(5-(4-chlorophenyl)-4,6-dimethyl-2-pyridyl)urea | |
| 169 | 1-(2-fluoro-6-methoxybenzoyl)-3-(5-(4-chlorophenyl)-4,6-dimethyl-2-pyridyl)urea | |
| 170 | 1-(2-chloro-6-fluorobenzoyl)-3-(4,6-dimethyl-5-phenyl-2-pyridyl)urea | |
| 171 | 1-(2,6-dichlorobenzoyl)-3-(4,6-dimethyl-5-phenyl-2-pyridyl)urea | |
| 172 | 1-(2,6-difluorobenzoyl)-3-(4,6-dimethyl-5-(4-fluorophenyl)-2-pyridyl)urea | |
| 173 | 1-(2-chlorobenzoyl)-3-(4,6-dimethyl-5-(4-fluorophenyl)-2-pyridyl)urea | |
| 174 | 1-(2,6-dichlorobenzoyl)-3-(4,6-dimethyl-5-(4-fluorophenyl)-2-pyridyl)urea | |
| 175 | 1-(2-bromobenzoyl)-3-(4,6-dimethyl-5-(4-fluorophenyl)-2-pyridyl)urea | |
| 176 | 1-(2,6-difluorobenzoyl)-3- | 224–226° C. |

| EXAMPLE NO. | COMPOUND NAME | MELTING POINT |
|---|---|---|
| | (4,6-dimethyl-5-(4-methoxy-phenyl)-2-pyridyl)urea | |
| 177 | 1-(2-chloro-6-fluorobenzoyl)-3-(4,6-dimethyl-5-(4-methoxy-phenyl)-2-pyridyl)urea | 200–207° C. |
| 178 | 1-(2-chlorobenzoyl)-3-(4,6-dimethyl-5-(4-methoxyphenyl)-2-pyridyl)urea | |
| 179 | 1-(2,6-dichlorobenzoyl)-3-(4,6-dimethyl-5-(4-methoxyphenyl)-2-pyridyl)urea | |
| 180 | 1-(2-bromobenzoyl)-3-(4,6-dimethyl-5-(4-methoxyphenyl)-2-pyridyl)urea | |
| 181 | 1-(2-fluoro-6-methoxybenzoyl)-3-(4,6-dimethyl-5-(4-methoxyphenyl)-2-pyridyl)urea | |
| 182 | 1-(2,6-difluorobenzoyl)-3-(4,6-dimethyl-5-(4-(trifluoromethyl)-phenyl)-2-pyridyl)urea | |
| 183 | 1-(2-chloro-6-fluorobenzoyl)-3-(4,6-dimethyl-5-(4-trifluoromethyl)phenyl)-2-pyridyl)urea | |
| 184 | 1-(2-chlorobenzoyl)-3-(4,6-dimethyl-5-(4-(trifluoromethyl)-phenyl)-2-pyridyl)urea | |
| 185 | 1-(2,6-dichlorobenzoyl)-3-(4,6-dimethyl-5-(4-(trifluoromethyl)-phenyl)-2-pyridyl)urea | |
| 186 | 1-(2-bromobenzoyl)-3-(4,6-dimethyl-5-(4-(trifluoromethyl)-phenyl)-2-pyridyl)urea | |
| 187 | 1-(2,6-dimethoxybenzoyl)-3-(4,6-dimethyl-5-(4-(trifluoromethyl)-phenyl)-2-pyridyl)urea | |
| 188 | 1-(2,6-difluorobenzoyl)-3-(4,6-dimethyl-5-(3-(trifluoromethyl)-phenyl)-2-pyridyl)urea | |
| 189 | 1-(2-chloro-6-fluorobenzoyl)-3-(4,6-dimethyl-5-(3-(trifluoromethyl)phenyl)-2-pyridyl)urea | |
| 190 | 1-(2-chlorobenzoyl)-3-(4,6-dimethyl-5-(3-(triflouromethyl)-phenyl)-2-pyridyl)urea | |
| 191 | 1-(2,6-dichlorobenzoyl)-3-(4,6-dimethyl-5-(3-(trifluoromethyl)-phenyl)-2-pyridyl)urea | |
| 192 | 1-(2-bromobenzoyl)-3-(4,6-dimethyl-5-(3-(trifluoromethyl)phenyl)-2-pyridyl)urea | |
| 193 | 1-(2,6-difluorobenzoyl)-3-(4,6-dimethyl-5-(4-tolyl)-2-pyridyl)-urea | |
| 194 | 1-(2-chlorobenzoyl)-3-(4,6-dimethyl-5-(4-tolyl)-2-pyridyl)-urea | |
| 195 | 1-(2,6-dichlorobenzoyl)-3-(4,6-dimethyl-5-(4-tolyl)-2-pyridyl)-urea | |
| 196 | 1-(2-bromobenzoyl)-3-(4,6-dimethyl-5-(4-tolyl)-2-pyridyl)urea | |
| 197 | 1-(2-chloro-6-methoxybenzoyl)-3-(4,6-dimethyl-5-(4-tolyl)-2-pyridyl)urea | |
| 198 | 1-(2,6-dimethylbenzoyl)-3-(4,6-dimethyl-5-(4-tolyl)-2-pyridyl)urea | |
| 199 | 1-(2,6-difluorobenzoyl)-3-(4,6-dimethyl-5-(4-trifluoromethoxy)-phenyl)-2-pyridyl)urea | |
| 200 | 1-(2-chloro-6-fluorobenzoyl)-3-(4,6-dimethyl-5-(4-(trifluoromethoxy)phenyl)-2-pyridyl)urea | |
| 201 | 1-(2-chlorobenzoyl)-3-(4,6-dimethyl-5-(4-(trifluoromethoxy)phenyl)-2-pyridyl)urea | |
| 202 | 1-(2,6-dichlorobenzoyl)-3-(4,6-dimethyl-5-(4-(trifluoromethoxy)phenyl)-2-pyridyl)urea | |
| 203 | 1-(2-bromobenzoyl)-3-(4,6-dimethyl-5-(4-(trifluoromethoxy)phenyl)-2-pyridyl)urea | |
| 204 | 1-(2,6-dimethoxybenzoyl)-3-(4,6-dimethyl-5-(4-(trifluoromethoxy)phenyl)-2-pyridyl)urea | |
| 205 | 1-(2-fluoro-6-methoxybenzoyl)-3-(4,6-dimethyl-5-(4-(trifluoromethoxy)phenyl)-2-pyridyl)urea | |
| 206 | 1-(2,6-difluorobenzoyl)-3-(5-(4-chlorophenyl)-4,6-dimethyl-2-pyridyl)thiourea | |
| 207 | 1-(2,6-dichlorobenzoyl)-3-(5-(4-chlorophenyl)-4,6-dimethyl-2-pyridyl)thiourea | |
| 208 | 1-(2,6-difluorobenzoyl)-3-(5-(4-chlorophenyl)-4,6-dimethyl-2-pyridyl-1-oxide)urea | |
| 209 | 1-(2-chlorobenzoyl)-3-(5-(4-chlorophenyl)-4,6-dimethyl-2-pyridyl-1-oxide)urea | |
| 210 | 1-(2-chloro-6-fluorobenzoyl)-3-(5-(4-chlorophneyl)-4,6-dimethyl-2-pyridyl-1-oxide)urea | |
| 211 | 1-(2,6-dichlorobenzoyl)-3-(5-(4-chlorophenyl)-4,6-dimethyl-2-pyridyl-1-oxide)urea | |
| 212 | 1-(2,6-difluorobenzoyl)-3-(6-(4-bromophenyl)-3-pyridyl)urea | |
| 213 | 1-(2-chlorobenzoyl)-3-(6-(4-bromophenyl)-3-pyridyl)urea | |
| 214 | 1-(2,6-dichlorobenzoyl)-3-(6-(4-bromophenyl)-3-pyridyl)urea | |
| 215 | 1-(2-chloro-6-fluorobenzoyl)-3-(6-(4-chlorophenyl)-3-pyridyl)-urea | |
| 216 | 1-(2-bromobenzoyl)-3-(6-(4-chlorophenyl)-3-pyridyl)urea | |
| 217 | 1-(2-chloro-6-methoxybenzoyl)-3-(6-(4-chlorophenyl)-3-pyridyl)urea | |
| 218 | 1-(2,6-difluorobenzoyl)-3-(6-(3-trifluoromethyl)phenyl)-3-pyridyl)urea | |
| 219 | 1-(2-chloro-6-fluorobenzoyl)-3-(6-(3-trifluoromethyl)phenyl)-3-pyridyl)urea | |
| 220 | 1-(2,6-difluorobenzoyl)-3-(6-(4-trifluoromethyl)phenyl)-3-pyridyl)urea | |
| 221 | 1-(2,6-dichlorobenzoyl)-3-(6-(4-trifluoromethyl)phenyl)-3-pyridyl)urea | |
| 222 | 1-(2,6-difluorobenzoyl)-3-(6-(4-chlorophenyl)-5-methyl-3-pyridyl)-urea | |
| 223 | 1-(2-chloro-6-fluorobenzoyl-3-(6-(4-chlorophenyl)-5-methyl-3-pyridyl)urea | |
| 224 | 1-(2-bromobenzoyl)-3-(6-(4-chlorophenyl)-5-methyl-3-pyridyl)urea | |
| 225 | 1-(2,6-difluorobenzoyl)-3-(6-(4-bromophenyl)-5-methyl-3-pyridyl)urea | |
| 226 | 1-(2-chloro-6-fluorobenzoyl)-3-(6-(4-bromophenyl)-5-methyl-3-pyridyl)urea | |
| 227 | 1-(2-chlorobenzoyl)-3-(6-(4-bromophenyl)-5-methyl-3-pyridyl)urea | |
| 228 | 1-(2,6-dichlorobenzoyl)-3-(6-(4-bromophenyl)-5-methyl-3-pyridyl)urea | |
| 229 | 1-(2-bromobenzoyl)-3-(6-(4-bromophenyl)-5-methyl-3-pyridyl)urea | |
| 230 | 1-(2-bromobenzoyl)-3-(6-chloro-5-(4-chlorophenyl)-2-pyridyl)-urea | |

-continued

| EXAMPLE NO. | COMPOUND NAME | MELTING POINT |
|---|---|---|
| 231 | 1-(2,6-difluorobenzoyl)-3-(5-(4-bromophenyl)-6-chloro-2-pyridyl)urea | |
| 232 | 1-(2-chloro-6-fluorobenzoyl)-3-(5-(4-bromophenyl)-6-chloro-2-pyridyl)urea | |
| 233 | 1-(2-chlorobenzoyl)-3-(5-(4-bromophenyl)-6-chloro-2-pyridyl)urea | |
| 234 | 1-(2,6-dichlorobenzoyl)-3-(5-(4-bromophenyl)-6-chloro-2-pyridyl)urea | |
| 235 | 1-(2-bromobenzoyl)-3-(5-(4-bromophenyl)-6-chloro-2-pyridyl)urea | |
| 236 | 1-(2,6-difluorobenzoyl)-3-(6-chloro-5-(4-fluorophenyl)-2-pyridyl)urea | |
| 237 | 1-(2-chloro-6-fluorobenzoyl)-3-(6-chloro-5-(4-fluorophenyl)-2-pyridyl)urea | |
| 238 | 1-(2-chlorobenzoyl)-3-(6-chloro-5-(4-fluorophenyl)-2-pyridyl)urea | |
| 239 | 1-(2,6-dichlorobenzoyl)-3-(6-chloro-5-(4-fluorophenyl)-2-pyridyl)urea | |
| 240 | 1-(2,6-difluorobenzoyl)-3-(5-(4-chlorophenyl)-4,6-dichloro-2-pyridyl)urea | |
| 241 | 1-(2-chlorobenzoyl)-3-(5-(4-chlorophenyl)-4,6-dichloro-2-pyridyl)urea | |
| 242 | 1-(2,6-dichlorobenzoyl)-3-(5-(4-chlorophenyl)-4,6-dichloro-2-pyridyl)urea | |
| 243 | 1-(2,6-difluorobenzoyl)-3-(6-bromo-5-(4-chlorophenyl)-2-pyridyl)urea | |
| 244 | 1-(2-chlorobenzoyl)-3-(6-bromo-5-(4-chlorophenyl)-2-pyridyl)urea | |
| 245 | 1-(2,6-dichlorobenzoyl)-3-(6-bromo-5-(4-chlorophenyl)-2-pyridyl)urea | |
| 246 | 1-(2-chloro-6-fluorobenzoyl)-3-(6-bromo-5-(4-chlorophenyl)-2-pyridyl)urea | |
| 247 | 1-(2-bromobenzoyl)-3-(5-(4-chlorophenyl)-4-methyl-2-pyridyl)urea | |
| 248 | 1-(2-chloro-6-methoxybenzoyl)-3-(5-(4-chlorophenyl)-4-methyl-2-pyridyl)urea | |
| 249 | 1-(2-chloro-6-fluorobenzoyl)-3-(5-(4-bromophenyl)-4-methyl-2-pyridyl)urea | |
| 250 | 1-(2,6-dichlorobenzoyl)-3-(5-(4-bromophenyl)-4-methyl-2-pyridyl)urea | |
| 251 | 1-(2,6-difluorobenzoyl)-3-(4-methyl-5-(3-(trifluoromethyl)phenyl)-2-pyridyl)urea | |
| 252 | 1-(2-chloro-6-fluorobenzoyl)-3-(4-methyl-5-(3-(trifluoromethyl)phenyl)-2-pyridyl)urea | |
| 253 | 1-(2,6-dichlorobenzoyl)-3-(4-methyl-5-(3-(trifluoromethyl)phenyl)-2-pyridyl)urea | |
| 254 | 1-(2,6-difluorobenzoyl)-3-(4-methyl-5-(4-(trifluoromethyl)phenyl)-2-pyridyl)urea | |
| 255 | 1-(2-chlorobenzoyl)-3-(4-methyl-5-(4-(trifluoromethyl)phenyl)-2-pyridyl)urea | |
| 256 | 1-(2,6-dichlorobenzoyl)-3-(4-methyl-5-(4-(trifluoromethyl)phenyl)-2-pyridyl)urea | |
| 257 | 1-(2-bromobenzoyl)-3-(4-methyl-5-(4-(trifluoromethyl)phenyl)-2-pyridyl)urea | |
| 258 | 1-(2-bromobenzoyl)-3-(5-(4-chlorophenyl)-2-pyridyl)urea | 223–230° C. |
| 259 | 1-(2-fluoro-6-methoxybenzoyl)-3-(5-(4-chlorophenyl)-2-pyridyl)urea | |
| 260 | 1-(2,6-difluorobenzoyl)-3-(5-(4-bromophenyl)-2-pyridyl)urea | |
| 261 | 1-(2-chloro-6-fluorobenzoyl)-3-(5-(4-bromophenyl)-2-pyridyl)urea | |
| 262 | 1-(2-bromobenzoyl)-3-(5-(4-bromophenyl)-2-pyridyl)urea | |
| 263 | 1-(2,6-difluorobenzoyl)-3-(5-(4-fluorophenyl)-2-pyridyl)urea | |
| 264 | 1-(2-chloro-6-fluorobenzoyl)-3-(5-(4-fluorophenyl)-2-pyridyl)urea | |
| 265 | 1-(2-chlorobenzoyl)-3-(5-(4-fluorophenyl)-2-pyridyl)urea | |
| 266 | 1-(2,6-dichlorobenzoyl)-3-(5-(4-fluorophenyl)-2-pyridyl)urea | |
| 267 | 1-(2-chloro-6-fluorobenzoyl)-3-(5-(3-(trifluoromethyl)phenyl)-2-pyridyl)urea | |
| 268 | 1-(2,6-difluorobenzoyl)-3-(5-(4-(trifluoromethyl)phenyl)-2-pyridyl)urea | |
| 269 | 1-(2,6-dichlorobenzoyl)-3-(5-(4-(trifluoromethyl)phenyl)-2-pyridyl)urea | |
| 270 | 1-(2,6-difluorobenzoyl)-3-(5-(4-methoxyphenyl)-2-pyridyl)urea | |
| 271 | 1-(2-chloro-6-fluorobenzoyl)-3-(5-(4-methoxyphenyl)-2-pyridyl)urea | |
| 272 | 1-(2,6-dichlorobenzoyl)-3-(5-(4-methoxyphenyl)-2-pyridyl)urea | |
| 273 | 1-(2,6-dichlorobenzoyl)-3-(5-(4-methylthiophenyl)-2-pyridyl)urea | |
| 274 | 1-(2-chloro-6-fluorobenzoyl)-3-(6-methyl-5-phenyl-2-pyridyl)urea | 194–198° C. |
| 275 | 1-(2-bromobenzoyl)-3-(5-(bromophenyl)-6-methyl-2-pyridyl)urea | |
| 276 | 1-(2-chloro-6-fluorobenzoyl)-3-(5-(4-bromophenyl)-6-methyl-2-pyridyl)urea | |
| 277 | 1-(2,6-dichlorobenzoyl)-3-(5-(4-bromophenyl)-6-methyl-2-pyridyl)urea | |
| 278 | 1-(2-bromobenzoyl)-3-(5-(4-bromophenyl)-6-methyl-2-pyridyl)urea | |
| 279 | 1-(2-methylbenzoyl)-3-(5-(4-bromophenyl)-6-methyl-2-pyridyl)urea | |
| 280 | 1-(2-chloro-6-fluorobenzoyl)-3-(6-methyl-5-(tolyl)-2-pyridyl)urea | |
| 281 | 1-(2-bromobenzoyl)-3-(6-methyl-5-(4-tolyl)-2-pyridyl)urea | 208–214° C. |
| 282 | 1-(2-chloro-6-fluorobenzoyl)-3-(5-(3-chlorophenyl)-6-methyl-2-pyridyl)urea | |
| 283 | 1-(2-chlorobenzoyl)-3-(5-(3-chlorophenyl)-6-methyl-2-pyridyl)urea | |
| 284 | 1-(2,6-dichlorobenzoyl)-3-(5-(3-chlorophenyl)-6-methyl-2-pyridyl)urea | |
| 285 | 1-(2-chloro-6-fluorobenzoyl)-3-(5-(4-methoxyphenyl)-6-methyl-2-pyridyl)urea | |
| 286 | 1-(2-bromobenzoyl)-3-(5-(4-methoxyphenyl)-6-methyl-2-pyridyl)urea | |
| 287 | 1-(2,6-difluorobenzoyl)-3-(5-(4-fluorophenyl)-6-methyl-2-pyridyl)urea | |
| 288 | 1-(2-chloro-6-fluorobenzoyl)-3-(5-(4-fluorophenyl)-6-methyl-2-pyridyl)urea | |

-continued

| EXAMPLE NO. | COMPOUND NAME | MELTING POINT |
|---|---|---|
| 289 | 1-(2-chlorobenzoyl)-3-(5-(4-fluorophenyl)-6-methyl-2-pyridyl)urea | |
| 290 | 1-(2,6-dichlorobenzoyl)-3-(5-(4-fluorophenyl)-6-methyl-2-pyridyl)urea | |
| 291 | 1-(2-bromobenzoyl)-3-(5-(4-fluorophenyl)-6-methyl-2-pyridyl)urea | |
| 292 | 1-(2,6-difluorobenzoyl)-3-(6-methyl-5-(3-(trifluoromethyl)phenyl)-2-pyridyl)urea | |
| 293 | 1-(2-chloro-6-fluorobenzoyl)-3-(6-methyl-5-(3-(trifluoromethyl)phenyl)-2-pyridyl)urea | |
| 294 | 1-(2-chlorobenzoyl)-3-(6-methyl-5-(3-(trifluoromethyl)phenyl)-2-pyridyl)urea | |
| 295 | 1-(2,6-dichlorobenzoyl)-3-(6-methyl-5-(3-(trifluoromethyl)phenyl)-2-pyridyl)urea | |
| 296 | 1-(2,6-difluorobenzoyl)-3-(6-methyl-5-(4-(trifluoromethyl)phenyl)-2-pyridyl)urea | |
| 297 | 1-(2-chlorobenzoyl)-3-(6-methyl-5-(4-(trifluoromethyl)phenyl)-2-pyridyl)urea | |
| 298 | 1-(2,6-dichlorobenzoyl)-3-(6-methyl-5-(4-(trifluoromethyl)phenyl)-2-pyridyl)urea | |
| 299 | 1-(2,6-difluorobenzoyl)-3-(6-methyl-5-(4-trifluoromethoxy)phenyl)-2-pyridyl)urea | |
| 300 | 1-(2-chloro-6-fluorobenzoyl)-3-(6-methyl-5-(4-(trifluoromethoxy)phenyl)-2-pyridyl)urea | |
| 301 | 1-(2-chlorobenzoyl)-3-(6-methyl-5-(4-(trifluoromethoxy)phenyl)-2-pyridyl)urea | |
| 302 | 1-(2,6-dichlorobenzoyl)-3-(6-methyl-5-(4-(trifluoromethoxy)phenyl)-2-pyridyl)urea | |
| 303 | 1-(2-bromobenzoyl)-3-(6-methyl-5-(4-(trifluoromethoxy)phenyl)-2-pyridyl)urea | |
| 304 | 1-(2,6-dimethylbenzoyl)-3-(6-methyl-5-(4-(trifluoromethoxy)phenyl)-2-pyridyl)urea | |
| 305 | 1-(2-methylbenzoyl)-3-(6-methyl-5-(4-(trifluoromethoxy)phenyl)-2-pyridyl)urea | |
| 306 | 1-(2,6-difluorobenzoyl)-3-(5-(4-chlorophenyl)-6-methyl-2-pyridyl-1-oxide)urea | |
| 307 | 1-(2-chloro-6-fluorobenzoyl)-3-(5-(4-chlorophenyl)-6-methyl-2-pyridyl-1-oxide)urea | |
| 308 | 1-(2,6-dichlorobenzoyl)-3-(5-(4-chlorophenyl)-6-methyl-2-pyridyl-1-oxide)urea | |
| 309 | 1-(2-bromobenzoyl)-3-(5-(4-chlorophenyl)-4,6-dimethyl-2-pyridyl)urea | 210–213° C. |
| 310 | 1-(2-chloro-6-methoxybenzoyl)-3-(5-(4-chlorophenyl)-4,6-dimethyl-2-pyridyl)urea | 235–240° C. |
| 311 | 1-(2-methylbenzoyl)-3-(5-(4-chlorophenyl)-4,6-dimethyl-2-pyridyl)urea | 218–224° C. |
| 312 | 1-(2,6-dimethylbenzoyl)-3-(5-(4-chlorophenyl)-4,6-diethyl-2-pyridyl)urea | |
| 313 | 1-(2,6-dichlorobenzoyl)-3-(5-(4-chlorophenyl)-4,6-dimethyl-2-pyridyl)urea | 232–234° C. |
| 314 | 1-(2,6-dimethylbenzoyl)-3-(5-(4-chlorophenyl)-4,6-dimethyl-2-pyridyl)urea | 248–251° C. |
| 315 | 1-(2,6-dimethoxybenzoyl)-3- | 250–256° C. |

-continued

| EXAMPLE NO. | COMPOUND NAME | MELTING POINT |
|---|---|---|
| | (5-(4-bromophenyl)-4,6-dimethyl-2-pyridyl)urea | |
| 316 | 1-(2,6-difluorobenzoyl)-3-(5-(4-chlorophenyl)-2-pyridyl-1-oxide)urea | |
| 317 | 1-(2,6-dibromobenzoyl)-3-(5-(4-chlorophenyl)-2-pyridyl-1-oxide)urea | |
| 318 | 1-(2-chloro-6-fluorobenzoyl)-3-(5-(4-chlorophenyl)-2-pyridyl-1-oxide)urea | |
| 319 | 1-(2,6-dichlorobenzoyl)-3-(5-(4-fluorophenyl)-2-pyridyl-1-oxide)urea | |
| 320 | 1-(2,6-difluorobenzoyl)-3-(5-(4-bromophenyl)-2-pyridyl-1-oxide)urea | |
| 321 | 1-(2-chloro-6-fluorobenzoyl)-3-(5-(4-fluorophenyl)-2-pyridyl-1-oxide)urea | |
| 322 | 1-(2,6-dichlorobenzoyl)-3-(5-(4-tolyl)-2-pyridyl-1-oxide)urea | |
| 323 | 1-(2,6-difluorobenzoyl)-3-(5-(4-tolyl)-2-pyridyl-1-oxide)urea | |
| 324 | 1-(2-chloro-6-fluorobenzoyl)-3-(5-(4-tolyl)-2-pyridyl-1-oxide)urea | |
| 325 | 1-(2,6-dichlorobenzoyl)-3-(5-(4-(trifluoromethyl)phenyl)-2-pyridyl-1-oxide)urea | |
| 326 | 1-(2,6-difluorobenzoyl)-3-(5-(4-(trifluoromethyl)phenyl)-2-pyridyl-1-oxide)urea | |
| 327 | 1-(2,6-dibromobenzoyl)-3-(5-(4-(trifluoromethyl)phenyl)-2-pyridyl-1-oxide)urea | |
| 328 | 1-(2-chloro-6-fluorobenzoyl)-3-(5-(4-(trifluoromethyl)phenyl)-2-pyridyl-1-oxide)urea | |
| 329 | 1-(2,6-dichlorobenzoyl)-3-(5-(4-chlorophenyl)-4-methyl-2-pyridyl-1-oxide)urea | |
| 330 | 1-(2,6-dichlorobenzoyl)-3-(4-methyl-5-(4-tolyl)-2-pyridyl-1-oxide)urea | |
| 331 | 1-(2,6-dichlorobenzoyl)-3-(4-methyl-5-(4-(trifluoromethyl)phenyl)-2-pyridyl-1-oxide)urea | |
| 332 | 1-(2,6-difluorobenzoyl)-3-(4-methyl-5-(4-(trifluoromethyl)phenyl)-2-pyridyl-1-oxide)urea | |
| 333 | 1-(2,6-difluorobenzoyl)-3-(4-methyl-5-(4-tolyl)-2-pyridyl-1-oxide)urea | |
| 334 | 1-(2-chloro-6-fluorobenzoyl)-3-(4-methyl-5-(4-tolyl)-2-pyridyl-1-oxide)urea | |
| 335 | 1-(2-chloro-6-fluorobenzoyl)-3-(4-methyl-5-(4-(trifluoromethyl)phenyl)-2-pyridyl-1-oxide)urea | |
| 336 | 1-(2-chloro-6-fluorobenzoyl)-3-(5-(4-chlorophenyl)-4-methyl-2-pyridyl-1-oxide)urea | |
| 337 | 1-(2,6-difluorobenzoyl)-3-(5-(4-chlorophenyl)-4-methyl-2-pyridyl-1-oxide)urea | |
| 338 | 1-(2,6-dibromobenzoyl)-3-(5-(4-chlorophenyl)-4-methyl-2-pyridyl)-1-oxide)urea | |
| 339 | 1-(2,6-dichlorobenzoyl)-3-(6-methyl-5-(4-tolyl)-2-pyridyl-1-oxide)urea | |
| 340 | 1-(2,6-dichlorobenzoyl)-3-(6-methyl-5-(4-(trifluoromethyl)phenyl)-2-pyridyl-1-oxide)urea | |
| 341 | 1-(2,6-difluorobenzoyl)-3-(6-methyl-5-(4-(trifluoromethyl)phenyl)-2-pyridyl-1-oxide)urea | |
| 342 | 1-(2,6-difluorobenzoyl)-3-(6-methyl-5-(4-tolyl)-2-pyridyl-1-oxide)urea | |
| 343 | 1-(2-chloro-6-fluorobenzoyl)-3- | |

| EXAMPLE NO. | COMPOUND NAME | MELTING POINT |
|---|---|---|
| | (6-methyl-5-(4-tolyl)-2-pyridyl-1-oxide)urea | |
| 344 | 1-(2-chloro-6-fluorobenzoyl)-3-(6-methyl-5-(4-(trifluoromethyl)-phenyl)-2-pyridyl-1-oxide)urea | |
| 345 | 1-(2,6-dibromobenzoyl)-3-(4,6-dichloro-5-(4-chlorophenyl)-2-pyridyl-1-oxide)urea | |
| 346 | 1-(2,6-dibromobenzoyl)-3-(4,6-dichloro-5-(4-tolyl)-2-pyridyl-1-oxide)urea | |
| 347 | 1-(2,6-dibromobenzoyl)-3-(4,6-dichloro-5-(4-(trifluoromethyl)-phenyl)-2-pyridyl-1-oxide)urea | |
| 348 | 1-(2,6-dibromobenzoyl)-3-(4,6-dichloro-5-(4-tolyl)-2-pyridyl-1-oxide)urea | |
| 349 | 1-(2-chloro-6-bromobenzoyl)-3-(4,6-dichloro-5-(4-tolyl)-2-pyridyl-1-oxide)urea | |
| 350 | 1-(2-chloro-6-bromobenzoyl)-3-(4,6-dichloro-5-(4-(trifluoromethyl)-phenyl)-2-pyridyl-1-oxide)urea | |
| 351 | 1-(2-chloro-6-bromobenzoyl)-3-(4,6-dichloro-5-(4-chlorophenyl)-2-pyridyl-1-oxide)urea | |
| 352 | 1-(2,6-dibromobenzoyl)-3-(4,6-dichloro-5-(4-chlorophenyl)-2-pyridyl-1-oxide)urea | |
| 353 | 1-(2,6-dibromobenzoyl)-3-(4,6-dichloro-5-(4-(trifluoromethyl)phenyl)-2-pyridyl-1-oxide)urea | |
| 354 | 1-(2,6-dichlorobenzoyl)-3-(6-chloro-5-(4-chlorophenyl)-2-pyridyl-1-oxide)urea | |
| 355 | 1-(2,6-dichlorobenzoyl)-3-(6-chloro-5-(4-tolyl)-2-pyridyl-1-oxide)urea | |
| 356 | 1-(2,6-dichlorobenzoyl)-3-(6-chloro-5-(4-trifluoromethyl)-phenyl)-2-pyridyl-1-oxide)urea | |
| 357 | 1-(2,6-difluorobenzoyl)-3-(6-chloro-5-(4-tolyl)-2-pyridyl-1-oxide)urea | |
| 358 | 1-(2-chloro-6-fluorobenzoyl)-3-(6-chloro-5-(4-tolyl)-2-pyridyl-1-oxide)urea | |
| 359 | 1-(2-chloro-6-fluorobenzoyl)-3-(6-chloro-5-(4-(trifluoromethyl)-phenyl)-2-pyridyl-1-oxide)urea | |
| 360 | 1-(2-chloro-6-fluorophenyl)-3-(6-chloro-5-(4-chlorophenyl)-2-pyridyl-1-oxide)urea | |
| 361 | 1-(2,6-difluorobenzoyl)-3-(6-chloro-5-(4-chlorophenyl)-2-pyridyl-1-oxide)urea | |
| 362 | 1-(2,6-difluorobenzoyl)-3-(6-chloro-5-(4-(trifluoromethyl)-phenyl)-2-pyridyl-1-oxide)urea | |
| 363 | 1-(2,6-dichlorobenzoyl)-3-(4,6-dimethyl-5-(4-tolyl)-2-pyridyl-1-oxide)urea | |
| 364 | 1-(2,6-dichlorobenzoyl)-3-(4,6-dimethyl-5-(4-(trifluoromethyl)-phenyl)-2-pyridyl-1-oxide)urea | |
| 365 | 1-(2,6-difluorobenzoyl)-3-(4,6-dimethyl-5-(4-tolyl)-2-pyridyl-1-oxide)urea | |
| 366 | 1-(2-chloro-6-fluorobenzoyl)-3-(4,6-dimethyl-5-(4-tolyl)-2-pyridyl-1-oxide)urea | |
| 367 | 1-(2-chloro-6-fluorobenzoyl)-3-(4,6-dimethyl-5-(4-(trifluoromethyl)-phenyl)-2-pyridyl-1-oxide)urea | |
| 368 | 1-(2,6-difluorobenzoyl)-3-(4,6-dimethyl-5-(4-(trifluoromethyl)phenyl)-2-pyridyl-1-oxide)urea | |
| 369 | 1-(2,6-difluorobenzoyl)-3-(4,6-dimethyl-5-(4-fluorophenyl)-2-pyridyl-1-oxide)urea | |
| 370 | 1-(2,6-dichlorobenzoyl)-3-(4,6-dimethyl-5-(4-fluorophenyl)-2-pyridyl-1-oxide)urea | |
| 371 | 1-(2,6-dibromobenzoyl)-3-(5-(4-chlorophenyl)-4,6-dimethyl-2-pyridyl-1-oxide)urea | |
| 372 | 1-(2,6-difluorobenzoyl)-3-(5-(4-bromophenyl)-4,6-dimethyl-2-pyridyl-1-oxide)urea | |
| 373 | 1-(2,6-dichlorobenzoyl)-3-(4,6-dichloro-5-(4-tolyl)-2-pyridyl-1-oxide)urea | |
| 374 | 1-(2,6-dichlorobenzoyl)-3-(5-(4-chlorophenyl)-4,6-dichloro-2-pyridyl-1-oxide)urea | |
| 375 | 1-(2,6-difluorobenzoyl)-3-(5-(4-chlorophenyl)-4,6-dichloro-2-pyridyl-1-oxide)urea | |
| 376 | 1-(2-chloro-6-fluorobenzoyl)-3-(5-(4-chlorophenyl)-4,6-dichloro-2-pyridyl-1-oxide)urea | |
| 377 | 1-(2,6-dichlorobenzoyl)-3-(4,6-dichloro-5-(4-(trifluoromethyl)-phenyl)-2-pyridyl-1-oxide)urea | |
| 378 | 1-(2-chloro-6-fluorobenzoyl)-3-(4,6-dichloro-5-(4-tolyl)-2-pyridyl-1-oxide)urea | |
| 379 | 1-(2-chloro-6-fluorobenzoyl)-3-(4,6-dichloro-5-(4-trifluoromethyl)-phenyl-2-pyridyl-1-oxide)urea | |
| 380 | 1-(2,6-difluorobenzoyl)-3-(4,6-dichloro-5-(4-(trifluoromethyl)-phenyl)-2-pyridyl-1-oxide)urea | |
| 381 | 1-(2,6-dichlorobenzoyl)-3-(4,6-dichloro-5-(4-fluorophenyl)-2-pyridyl-1-oxide)urea | |
| 382 | 1-(2,6-difluorobenzoyl)-3-(5-(4-bromophenyl)-4,6-dichloro-2-pyridyl-1-oxide)urea | |
| 383 | 1-(2-chlorobenzoyl)-3-(5-(4-chlorophenyl)-4,6-dichloro-2-pyridyl-1-oxide)urea | |
| 384 | 1-(2-chlorobenzoyl)-3-(6-chloro-5-(4-chlorophenyl)-2-pyridyl-1-oxide)-urea | |
| 385 | 1-(2-chlorobenzoyl)-3-(4-methyl-5-(4-(trifluoromethyl)phenyl)-2-pyridyl-1-oxide)urea | |
| 386 | 1-(2-chlorobenzoyl)-3-(6-methyl-5-(4-tolyl)-2-pyridyl-1-oxide)urea | |
| 387 | 1-(2-bromobenzoyl)-3-(4,6-dimethyl-5-(4-fluorophenyl)-2-pyridyl-1-oxide)urea | |
| 388 | 1-(2-chlorobenzoyl)-3-(4,6-dimethyl-5-(4-fluorophenyl)-2-pyridyl-1-oxide)urea | |
| 389 | 1-(2-chlorobenzoyl)-3-(4,6-dimethyl-5-(4-tolyl)-2-pyridyl-1-oxide)urea | |
| 390 | 1-(2,6-dichlorobenzoyl)-3-(6-(4-chlorophenyl)-3-pyridyl-1-oxide)urea | |
| 391 | 1-(2,6-dichlorobenzoyl)-3-(6-(4-tolyl)-3-pyridyl-1-oxide)urea | |
| 392 | 1-(2,6-dichlorobenzoyl)-3-(6-(4-chlorophenyl)-5-methyl-2-pyridyl-1-oxide)urea | |
| 393 | 1-(2,6-difluorobenzoyl)-3-(6-(4-fluorophenyl)-3-pyridyl-1-oxide)urea | |
| 394 | 1-(2,6-difluorobenzoyl)-3-(6-(4-tolyl)-3-pyridyl-1-oxide)urea | |
| 395 | 1-(2,6-difluorobenzoyl)-3-(6-(4-bromophenyl)-5-methyl-3-pyridyl-1-oxide)urea | |
| 396 | 1-(2,6-difluorobenzoyl)-3-(5-methyl-6-(4-(trifluoromethyl)phenyl)-3-pyridyl-1-oxide)urea | |
| 397 | 1-(2,6-dichlorobenzoyl)-3-(5-methyl-6-(4-(trifluoromethyl)-phenyl)-3-pyridyl-1-oxide)urea | |
| 398 | 1-(2-chloro-6-fluorobenzoyl)-3-(6-(4-chlorophenyl)-3-pyridyl- | |

-continued

| EXAMPLE NO. | COMPOUND NAME | MELTING POINT |
|---|---|---|
| | 1-oxide)urea | |
| 399 | 1-(2-chloro-6-fluorobenzoyl)-3-(6-(4-tolyl)-3-pyridyl-1-oxide)urea | |
| 400 | 1-(2-chloro-6-fluorobenzoyl)-3-(6-(4-fluorophenyl)-5-methyl-3-pyridyl-1-oxide)urea | |
| 401 | 1-(2-chloro-6-fluorobenzoyl)-3-(5-methyl-6-(4-(trifluoromethyl)-phenyl)-3-pyridyl-1-oxide)urea | |

The compounds of the present invention are useful for the control of insects of various orders, including Coleoptera such as Mexican bean beetle, Colorado potato beetle, white grubs; Diptera, such as yellow-fever mosquitoes, house fly; Lepidoptera, such as European corn borer, corn earworm, tobacco budworm, Egyptian cotton leafworm, southern armyworm, fall armyworm, sod webworm, tobacco hornworm, loopers, beet armyworm, diamond back moth, imported cabbage worm; Orthoptera, such as German cockroach, American cockroach; and Thysanoptera, such as thrips.

The compounds of the present invention are additionally useful for the control of other insects such as horn fly, common cattle grub, stable fly, face fly, mosquitoes, screwworm, tabanid fly, army cutworm, midges, southwestern corn borer, lesser cornstalk borer, horse bot fly, cabbage maggot, velvet bean caterpillar, pecan nut casebearer, pink bollworm, hickory shuckworm, walnut caterpillar, green cloverworm, alfalfa caterpillar, leaf miner fly, yellow-striped armyworm, rednecked peanutworm, stalk borer, sunflower moth, tomato pin worm, Oriental fruit moth, plum curculio, peachtree borer, melon fly, lesser peachtree borer, grape root borer, black fly, nose bot fly, grape berry moth, sheep ked, leaf rollers, and spruce bud worms.

It is believed that the present compounds act by interfering with the mechanism of metamorphosis which occurs in insects, causing the death of the insects. It is also believed that ingestion by the insects is necessary to invoke this mechanism. While the death of any given insect may be delayed until that insect reaches some stage of metamorphosis, the net result of this activity is the control and suppression of insects.

Therefore, in another embodiment, the present invention is directed to a method of suppressing insects which comprises applying to a locus of the insects an effective amount of a compound of the present invention. The locus can be any environment inhabited by insects to be controlled, such as soil, air, water, foods, vegetation, manure, inert objects, stored matter such as grain, and the like. The compounds of the invention will normally be applied by spraying, to the locus in an amount varying from 0.001 to 10 lbs/acre depending on the nature of the locus and the type and severity of the insect infestation. Preferably the compounds are applied in an amount varying from 0.1 to 1 lb/acre.

Preferably the compounds of the present invention are supplied in a formulation, for ease of application. The compounds can be formulated with various adjuvants, including water, organic liquids, surface-active agents, inert solids, and the like. Suitable surface-active agents include anionic agents, such as sodium lauryl sulfate, sodium dodecylbenzenesulfonate, and the like; and nonionic agents, such as polyoxyethylene glycol nonylphenyl ether. Mixtures are often desirably employed. The formulation can take the form of a liquid, dust, granule, aerosol, and so forth containing from 0.1 to 80% of a compound of the invention. Specifically the formulation may be an emulsifiable concentrate having 12-50% actives, a wettable powder having up to 80% actives, a granule having up to 10% actives, and a dust having up to 1.25% actives. In addition to the amounts of actives specified, the balance of the ingredients for the previously listed formulations is comprised of the various adjuvants listed above. These adjuvants and their use in formulations such as those exemplified herein, are well known and appreciated in the art. Moreover it is understood that those with ordinary skill will readily select one or more of the above or different adjuvants for use in formulating the present compounds in accordance with the percentages disclosed above. The formulations also can be designed to slowly release the active compound or to make the active compound immediately available.

Many methods of formulation are known in the art and can be employed to implement the present invention. Accordingly, illustrative examples for formulating the compounds of the present invention are presented below. While for convenience the formulations given are for 1-(2,6-dichlorobenzoyl)-3-(5-(4-chlorophenyl)-2-pyridyl)urea and 1-(2,6-difluorobenzoyl)-3-(5-(4-chlorophenyl)-4,6-dimethyl-2-pyridyl)urea, any of the compounds of the present invention can also be similarly formulated. Furthermore it is understood that those skilled in the art will recognize still other ways to formulate the compounds of the present invention. The ingredients comprising the formulations exemplified herein are expressed in weight percentages and are arranged in tabular form as follows.

FORMULATION EXAMPLE A: WETTABLE POWDER

| Ingredient | Wt. %* | Wt. %** |
|---|---|---|
| 1-(2,6-dichlorobenzoyl)-3-(5-(4-chlorophenyl)-2-pyridyl)urea (97%) | 77.32 | 51.50 |
| Polyfon O*** | 5.00 | 5.00 |
| Stepanol ME*** | 5.00 | 5.00 |
| Zeolex 7*** | 5.00 | 5.00 |
| Barden Clay*** | 7.68 | 33.50 |

*Contains 75% active ingredient
**Contains 50% active ingredient
***Polyfon O is a lignin sulfonate used as a dispersing agent. It can be obtained from Westvaco Chemical Company, North Charleston, South Carolina 29406.
Stepanol ME is sodium lauryl sulfate and is used as a wetting agent.
Zeolex 7 is a silicon dioxide product used as an anticaking agent. It can be obtained from J. M. Huber Corporation, Edison, New Jersey 08817.
Barden Clay is used as a carrier diluent. It can be obtained from Vanderbilt Chemical Company, 230 Park Avenue, New York, New York 10017.

FORMULATION EXAMPLE B: GRANULE

| Ingredient | Wt. % |
|---|---|
| 1-(2,6-difluorobenzoyl)-3-(5-(4-chlorophenyl)-4,6-dimethyl-2-pyridyl)-urea | 5.15 |
| Ground corn cob or walnut shells | 94.85 |

FORMULATION EXAMPLE C: EMULSIFIABLE CONCENTRATE*

| Ingredient | Wt. % |
|---|---|
| 1-(2,6-dichlorobenzoyl)-3-(5-(4-chlorophenyl)-2-pyridyl)urea (97%) | 25.77 |

-continued

| Ingredient | Wt. % |
|---|---|
| Toximul D** | 2.50 |
| Toximul H** | 2.50 |
| Dowanol EM** | 20.00 |
| Xylene | 49.23 |

*Contains 2.0 lb/gallon active ingredient
**Toximul D and H are sulfonate/nonionic blends. They can be obtained from Stepan Chemical Company, Northfield, Illinois 60093. Dowanol EM is used as a solvent. It can be obtained from Dow Chemical Company, Midland, Michigan 48640.

FORMULATION EXAMPLE D: DUST*

| Ingredient | Wt. % |
|---|---|
| 1-(2,6-difluorobenzoyl)-3-(5-(4-chlorophenyl)-4,6-dimethyl-2-pyridyl)-urea (97%) | 1.03 |
| Micro-Cel E** | .20 |
| Sunspray 7N** | 1.00 |
| Talc** | 97.77 |

*Contains 1% active ingredient
**Micro-Cel E is a silicate absorptive agent. It can be obtained from John Mansville Company, Denver, Colorado 80217.
Sunspray 7N is a sticking agent. It can be obtained from SUNOCO, Philadelphia, Pennsylvania 19103.
Talc can be obtained from Cypress Industrial Minerals Company, Los Angeles, California 90071.

FORMULATION EXAMPLE E: AQUEOUS SUSPENSION*

| Ingredient | Wt. % |
|---|---|
| 1-(2,6-dichlorobenzoyl)-3-(5-(4-chlorophenyl)-2-pyridyl)urea (97%) | 58.00 |
| Pluraflo E-4** | 4.00 |
| Polyfon O | 1.00 |
| Xanthan gum** | 0.10 |
| Formalin | 0.10 |
| Ethylene glycol** | 7.30 |
| Water | 29.50 |

*Contains 5 lb/gallon active ingredient
**Pluraflo E-4 is a wetting agent. It can be obtained from BASF Wyandotte, Wyandotte, Michigan 48192. Xanthan gum is a thickening agent used to give the formulation stability. It can be obtained from Kelco Corporation, Division of Merck, Rahway, New Jersey 07066. Ethylene glycol is used to give the formulation freeze/thaw stability.

The concentration of active agent in the formulation is not critical, inasmuch as an effective concentration will vary with the nature of the locus to be treated, the severity of insect infestation, the susceptibility of the particular insects involved, etc. In general, concentrations ranging from about 0.1 to 1000 ppm give good results. As exemplified by Table 2, below, lesser concentrations of from about 5 to about 100 ppm have given good control of southern armyworm larvae.

The use of insecticides by oral administration to animals for the control of manure-breeding insects is a rather new concept in insect control. At the present time, only a few insecticides are so used, of which a standard reference compound is diflubenzuron, 1-(2,6-difluorobenzoyl)-3-(4-chlorophenyl)urea.

The compounds are active against the larvae of insects which breed in manure, especially insects of the order Diptera. Especially important manure-breeding insects, against which the method of this invention is particularly effective, include the house fly (*Musca domestica*), the stable fly (*Stomoxys calcitrans*), the horn fly (*Haematobia irritans*), and the face fly (*Musca autumnalis*).

Therefore in another embodiment, the compounds of the present invention are orally administered to the animals to be treated, and pass essentially unchanged through the alimentary tract of the animal. The compound thus is excreted in the animal's feces, where it is effective against the larvae of insects. The animals which may be treated in accordance with the present method include especially poultry, such as for example, chickens, ducks, turkeys and geese; ruminants, such as for example, cattle, sheep and goats; and economic monogastric animals, such as for example, horses and swine. The compounds may also be used, if desired, in carnivorous animals, such as those of the cat and dog families.

Use of the method of this invention in poultry, especially chickens, and in ruminants, especially bovines, is most highly preferred.

The exact means by which the compounds used in the method of this invention are administered to the animals is not critical. It is easiest and most convenient to mix the compound in the animal's feed. When the compounds are administered as feed additives, they may be used in concentrations in the feed ranging from about 1 ppm. to about 50 ppm. by weight. A preferred range of concentration is from about 1 ppm. to about 10 ppm. by weight.

The formulation of feed additives into animal feeds is a well known art. It is usual to make a concentrated premix as a raw material for treated feeds. The formulation of the premix is guided solely by convenience in mixing feed from the premix, and by economy. The premix may contain from about 1 to about 400 g./lb. of the insecticide, depending on convenience in mixing feed containing the desired concentration of the compound. Premixes may be either liquid or solid.

The improved feed premixes which are provided by this invention and which are novel because of the presence of the insecticides used in the method of this invention, are formulated in any of the conventionally-used physiologically-acceptable carriers. Liquid carriers which are suitable for premix use include glycols such as for example polyethylene glycols of various molecular weights and propylene glycol, inert oils including vegetable oils and highly-refined mineral oil, and physiologically-acceptable alcohols such as ethanol. Solid premix carriers include, for example, vermiculite, diatomaceous earth, physiologically-acceptable clays such as attapulgite and montmorillonite, and granulated or powdered feed components such as cracked corn, soybean meal, alfalfa meal, rice hulls, corn cobs, cracked wheat or oats, and waste materials of grain processing.

It will further be understood by those skilled in animal husbandry that animal feeds containing from about 1 ppm. to about 50 ppm. by weight of a compound useful in the method of this invention are novel and are important embodiments of the invention. Such feeds may preferably be in the form of cereal-based feeds, adapted to the needs of poultry, ruminants and/or monogastric animals such as horses and swine. The usual dry or slurried animal feeds, based on grains such as wheat, oats, barley, maize and the like, may be treated with compounds used in the method of this invention, just as animal feeds are routinely treated with medicaments and parasiticides in the ordinary practice of the animal husbandry art.

The compounds may also be administered as additives to the animal's drinking water, in which case they should be used in a concentration of from about 1 ppm.

to about 30 ppm., preferably from about 1 ppm. to about 15 ppm.

Administration of the compounds by means of sustained release boluses is particularly advantageous when ruminants, especially cattle, are to be treated. Such boluses are made as tablets are made, except that a means to delay the dissolution of the compound over a period of time is provided. Boluses may be made to release the compound steadily over long periods of time, even 100 days or more. A number of polymeric substances have been used to prepare slow-release boluses; particularly effective polymers are the copolymers of polylactic and polyglycolic acids. It is necessary to retain a slow-release bolus in the rumen of the treated ruminant, so that the bolus is not carried on out of the digestive tract. Boluses are retained in the rumen most easily by making them of a high-density material, as by mixing metal particles into the composition, or by providing wings which open in the rumen and make the bolus too large to get through the opening into the omasum of the animal. Boluses should release from about 0.01 mg./kg. of body weight/day to about 2 mg./kg./day, preferably from about 0.01 to about 0.25 mg./kg./day.

The compounds may also be administered in the form of pharmaceutical dosage forms, such as tablets, capsules, drenches, suspensions and the like, but administration in such forms is usually not preferred because of the relative inconvenience of such administration.

Mineral blocks provide another advantageous formulation with which to administer the insecticides, particularly to ruminant animals. Such blocks are usually supplied to ruminants, even to those on pasture. The usual blocks are highly compressed forms of physiologically desirable salts and nutritive substances, generally including phosphates, carbonates, halides, calcium salts, trace elements such as zinc, cobalt, manganese and the like, vitamins, steroids, and lubricants and binders to assist in compression.

Mineral blocks are old in the animal husbandry art. The addition of the insecticides of the present method, however, provides novel blocks which are important embodiments of the present invention. The insecticides should be added to the blocks in concentrations from about 0.01% to about 0.5%, preferably from about 0.05% to about 0.25%.

It is necessary to administer at least an insecticidally-effective amount of compound to the animal to be treated. It is most effective to measure the amount administered, however, as a concentration in the medium with which it is combined. Effective insecticidal amounts, or concentrations, are described above.

It is not implied that administration of any amount of any compound used in the method of this invention will kill all larvae of all manure-breeding insects. It is not in the nature of biological methods to be invariably 100% effective. However, the oral administration of a compound of the present method, in an insecticidally-effective amount, will produce a worthwhile reduction in the number of insect larvae which mature in the manure of the treated animal. In many cases complete control of the larvae will result, and no adults will develop. It is understood that partial control of the manure-breeding insects is significant and beneficial, and that the population of the insects is usefully reduced, even though not all of them may be killed by the insecticidal treatment.

Control of manure-breeding insects in accordance with the present invention is, clearly, more convenient and effective than is insect control by traditional methods of applying insecticides to the manure after it has been gathered and piled. The added operation of spraying or dusting insecticides over the manure is avoided. More importantly, the method of this invention results in the insecticidal compounds being intimately mixed through the mass of the manure, so that any larvae in the mass are sure to come into contact with the compound.

While all the compounds of the present invention show considerable efficacy in the control and eradication of undesirable insect pests, certain compounds are more effective than others. Accordingly, preferred compounds of the present invention are those wherein each R is independently chloro or fluoro, $X=O$, $n=0$, the NH to pyridine bond is at the 2-position of the pyridine ring, $R^2$ is at the 5-position of the pyridine ring and represents 4-bromo- or 4-chlorophenyl, and $R^1$ is at the 4-, 6-, or 4 and 6-positions of the pyridine ring and represents chloro or methyl. One of the most useful compounds of this preferred group has been shown to be 1-(2,6-difluorobenzoyl)-3-(5-(4-chlorophenyl)-4,6-dimethyl-2-pyridyl)urea. While it is understood that there are many other useful and potentially important embodiments of the present invention, the preferred embodiment is as disclosed herein above.

The insecticidal activity of the present compounds was determined by testing the efficacy of formulations of the compounds against Mexican bean beetle larvae (*Epilachna varivestis*), and against southern armyworm larvae (*Spodoptera eridania*). These insects are members of the Coleoptera and Lepidoptera orders of insects, respectively. The formulations were applied to the foliage of plants and the larvae were subsequently permitted to feed on the foliage. The compounds were tested in a plurality of concentrations, from a concentration of about 1000 ppm. to about 1 ppm.

Each compound to be tested was formulated by dissolving the compound in a solvent made up with small amounts of Toximul R and Toximul S, typically 5.9 grams and 4.0 grams, respectively, per liter of 1:1 anhydrous ethanol and acetone. Water was then added to obtain a solution containing the compound in a concentration of 1000 parts per million. A portion was diluted further with water containing small amounts of Toximul R and Toximul S, to obtain treating solutions of lesser concentrations. It is understood that those skilled in the art will vary the amounts of water and Toximul R and Toximul S depending on the particular concentration of active compound desired. Each of Toximul R and Toximul S is a sulfonate/nonionic blend produced by Stepan Chemical Company, Northfield, Ill.

Each solution of test compound was sprayed onto two 4-inch square pots of bean plants containing 6 to 10 plants per pot. The plants were allowed to dry and then 12 leaves were removed and the cut ends wrapped in water-soaked cellucotton. The leaves were divided between six 100×°mm. plastic petri dishes. Five second-instar Mexican bean beetle larvae (*Epilachna varivestis*) and five second- and third-instar southern armyworm larvae (*Spodoptera eridania*) were placed in each of three dishes. The dishes were then placed in a room wherein the temperature and relative humidity were controlled at about 78° F. and about 51 percent, respectively, for a period of four days, at which time the first evaluation of the effects of the test compounds was made. After this evaluation, two fresh leaves from the original treated pots were placed in each dish. The dishes were again maintained in the temperature and humidity controlled room for an additional three days until the final seven-day evaluation was made.

Insecticidal effect was determined by counting the number of living larvae per dish. All the treatments were compared to solvent controls and nontreated controls. The rating code (percent of control) used was as follows:

0=0%
1=1-50%
2=51-99%
3=100% control

The results of this test are set forth in Table 1, which follows. In the table column 1 identifies the compounds by the number of the preparative example; column 2 lists the concentration of the test compound in the formulation; and columns 3 through 6 give the Rating Code at days 4 and 7 for the two insects against which the compounds were tested. An N/T entry means 'not tested'.

TABLE 1

| Example No. | Appln. Rate ppm. | Insect Control | | | |
|---|---|---|---|---|---|
| | | Mexican Bean Beetle | | Southern Armyworm | |
| | | 4 days | 7 days | 4 days | 7 days |
| 7 | 1000 | 0 | 2 | 3 | 3 |
| | 100 | 0 | 1 | 3 | 3 |
| 8 | 1000 | 1 | 3 | 3 | 3 |
| | 100 | 0 | 2 | 2 | 3 |
| 9 | 1000 | 0 | 0 | 3 | 3 |
| | 100 | 0 | 1 | 3 | 3 |
| 13 | 1000 | N/T | N/T | 3 | 3 |
| | 100 | N/T | N/T | 3 | 3 |
| 16 | 1000 | N/T | N/T | 3 | 3 |
| | 100 | N/T | N/T | 3 | 3 |
| 24 | 1000 | 1 | 2 | 3 | 3 |
| | 100 | 1 | 3 | 3 | 3 |
| 25 | 1000 | N/T | N/T | 3 | 3 |
| | 100 | N/T | N/T | 2 | 3 |
| 25 | 1000 | N/T | N/T | 0* | 0* |
| | 100 | N/T | N/T | 0* | 0* |
| 32 | 1000 | N/T | N/T | 3 | 3 |
| | 100 | N/T | N/T | 3 | 3 |
| 39 | 1000 | N/T | N/T | 2 | 3 |
| | 100 | N/T | N/T | 2 | 2 |
| 40 | 1000 | N/T | N/T | 3 | 3 |
| | 100 | N/T | N/T | 1 | 2 |
| 47 | 1000 | N/T | N/T | 3 | 3 |
| | 100 | N/T | N/T | 3 | 3 |
| 53 | 1000 | 1 | 2 | 3 | 3 |
| | 100 | 0 | 1 | 3 | 3 |
| 59 | 1000 | 2 | 3 | 2 | 3 |
| | 100 | 1 | 3 | 2 | 3 |
| 61 | 1000 | N/T | N/T | 3 | 3 |
| | 100 | N/T | N/T | 3 | 3 |
| 71 | 1000 | N/T | N/T | 3 | 3 |
| | 100 | N/T | N/T | 3 | 3 |
| 72 | 1000 | N/T | N/T | 2 | 2 |
| | 100 | N/T | N/T | 0 | 2 |
| 73 | 1000 | N/T | N/T | 3 | 3 |
| | 100 | N/T | N/T | 3 | 3 |
| 74 | 1000 | N/T | N/T | 3 | 3 |
| | 100 | N/T | N/T | 1 | 2 |
| 75 | 1000 | N/T | N/T | 3 | 3 |
| | 100 | N/T | N/T | 2 | 3 |
| 76 | 1000 | N/T | N/T | 3 | 3 |
| | 100 | N/T | N/T | 1 | 2 |
| 78 | 1000 | N/T | N/T | 3 | 3 |
| | 100 | N/T | N/T | 3 | 3 |
| 79 | 1000 | N/T | N/T | 3 | 3 |
| | 100 | N/T | N/T | 3 | 3 |
| 80 | 1000 | N/T | N/T | 3 | 3 |
| | 100 | N/T | N/T | 1 | 3 |
| 81 | 1000 | N/T | N/T | 3 | 3 |
| | 100 | N/T | N/T | 3 | 3 |
| 82 | 1000 | N/T | N/T | 0 | 2 |
| | 100 | N/T | N/T | 0 | 1 |

TABLE 1-continued

| Example No. | Appln. Rate ppm. | Insect Control | | | |
|---|---|---|---|---|---|
| | | Mexican Bean Beetle | | Southern Armyworm | |
| | | 4 days | 7 days | 4 days | 7 days |
| 83 | 1000 | N/T | N/T | 3 | 3 |
| | 100 | N/T | N/T | 3 | 3 |
| 84 | 1000 | N/T | N/T | 3 | 3 |
| | 100 | N/T | N/T | 2 | 2 |
| 85 | 1000 | N/T | N/T | 2 | 2 |
| | 100 | N/T | N/T | 0 | 1 |
| 86 | 1000 | N/T | N/T | 2 | 3 |
| | 100 | N/T | N/T | 2 | 2 |
| 87 | 1000 | N/T | N/T | 3 | 3 |
| | 100 | N/T | N/T | 2 | 3 |
| 88 | 1000 | N/T | N/T | 3 | 3 |
| | 100 | N/T | N/T | 2 | 3 |
| 89 | 1000 | N/T | N/T | 1 | 2 |
| | 100 | N/T | N/T | 0 | 0 |
| 90 | 1000 | N/T | N/T | 3 | 3 |
| | 100 | N/T | N/T | 1 | 3 |
| 91 | 1000 | N/T | N/T | 2 | 2 |
| | 100 | N/T | N/T | 1 | 2 |
| 92 | 1000 | N/T | N/T | 1 | 1 |
| | 100 | N/T | N/T | 0 | 0 |
| 93 | 1000 | N/T | N/T | 3 | 3 |
| | 100 | N/T | N/T | 2 | 2 |
| 94 | 1000 | N/T | N/T | 3 | 3 |
| | 100 | N/T | N/T | 2 | 3 |
| 95 | 1000 | N/T | N/T | 3 | 3 |
| | 100 | N/T | N/T | 3 | 3 |
| 96 | 1000 | N/T | N/T | 3 | 3 |
| | 100 | N/T | N/T | 3 | 3 |
| 97 | 1000 | N/T | N/T | 3 | 3 |
| | 100 | N/T | N/T | 3 | 3 |
| 98 | 1000 | N/T | N/T | 3 | 3 |
| | 100 | 1 | 3 | 3 | 3 |
| 99 | 1000 | N/T | N/T | 3 | 3 |
| | 100 | 1 | 3 | 3 | 3 |
| 100 | 1000 | N/T | N/T | 3 | 3 |
| | 100 | N/T | N/T | 3 | 3 |
| 101 | 1000 | N/T | N/T | 3 | 3 |
| | 100 | N/T | N/T | 3 | 3 |
| 102 | 1000 | N/T | N/T | 3 | 3 |
| | 100 | N/T | N/T | 1 | 2 |
| 103 | 1000 | N/T | N/T | 3 | 3 |
| | 100 | N/T | N/T | 2 | 2 |
| 104 | 1000 | N/T | N/T | 3 | 3 |
| | 100 | N/T | N/T | 2 | 3 |
| 105 | 1000 | 2 | 3 | 3 | 3 |
| | 100 | 2 | 3 | 3 | 3 |
| 106 | 1000 | 3 | 3 | 0 | 0 |
| | 100 | 3 | 3 | 0 | 0 |
| 107 | 1000 | N/T | N/T | 3 | 3 |
| | 100 | N/T | N/T | 3 | 3 |
| 108 | 1000 | N/T | N/T | 3 | 3 |
| | 100 | 2 | 3 | 3 | 3 |
| 109 | 1000 | N/T | N/T | 3 | 3 |
| | 100 | N/T | N/T | 3 | 3 |
| 110 | 1000 | N/T | N/T | 3 | 3 |
| | 100 | N/T | N/T | 3 | 3 |
| 111 | 1000 | N/T | N/T | 3 | 3 |
| | 100 | N/T | N/T | 3 | 3 |
| 112 | 1000 | N/T | N/T | 3 | 3 |
| | 100 | N/T | N/T | 3 | 3 |
| 113 | 1000 | N/T | N/T | 3 | 3 |
| | 100 | N/T | N/T | 3 | 3 |
| 114 | 1000 | N/T | N/T | 3 | 3 |
| | 100 | 0 | 0 | 3 | 3 |
| 115 | 1000 | N/T | N/T | 3 | 3 |
| | 100 | N/T | N/T | 3 | 3 |
| 116 | 1000 | N/T | N/T | 3 | 3 |
| | 100 | N/T | N/T | 1 | 1 |
| 117 | 1000 | N/T | N/T | 3 | 3 |
| | 100 | N/T | N/T | 0 | 0 |
| 118 | 1000 | N/T | N/T | 3 | 3 |
| | 100 | N/T | N/T | 1 | 2 |
| 119 | 1000 | N/T | N/T | 3 | 3 |
| | 100 | N/T | N/T | 3 | 3 |
| 120 | 1000 | N/T | N/T | 3 | 3 |
| | 100 | N/T | N/T | 2 | 3 |
| 121 | 1000 | N/T | N/T | 3 | 3 |

TABLE 1-continued

| Example No. | Appln. Rate ppm. | Insect Control Mexican Bean Beetle 4 days | 7 days | Southern Armyworm 4 days | 7 days |
|---|---|---|---|---|---|
| | 100 | 1 | 3 | 3 | 3 |
| 122 | 1000 | N/T | N/T | 3 | 3 |
| | 100 | N/T | N/T | 3 | 3 |
| 123 | 1000 | N/T | N/T | 3 | 3 |
| | 100 | N/T | N/T | 2 | 2 |
| 124 | 1000 | N/T | N/T | 3 | 3 |
| | 100 | N/T | N/T | 3 | 3 |
| 125 | 1000 | N/T | N/T | N/T | N/T |
| | 100 | N/T | N/T | 3 | 3 |
| 126 | 1000 | N/T | N/T | 2 | 3 |
| | 100 | N/T | N/T | 2 | 3 |
| 127 | 1000 | N/T | N/T | 3 | 3 |
| | 100 | N/T | N/T | 3 | 3 |
| 128 | 1000 | N/T | N/T | 3 | 3 |
| | 100 | N/T | N/T | 2 | 3 |
| 129 | 1000 | N/T | N/T | 3 | 3 |
| | 100 | N/T | N/T | 3 | 3 |
| 130 | 1000 | N/T | N/T | 3 | 3 |
| | 100 | N/T | N/T | 3 | 3 |
| 131 | 1000 | N/T | N/T | 3 | 3 |
| | 100 | N/T | N/T | 3 | 3 |
| 132 | 1000 | N/T | N/T | 3 | 3 |
| | 100 | N/T | N/T | 3 | 3 |
| 133 | 1000 | N/T | N/T | 3 | 3 |
| | 100 | N/T | N/T | 3 | 3 |
| 134 | 1000 | N/T | N/T | 3 | 3 |
| | 100 | N/T | N/T | 3 | 3 |
| 135 | 1000 | N/T | N/T | 3 | 3 |
| | 100 | N/T | N/T | 3 | 3 |
| 136 | 1000 | 0 | 2 | 3 | 3 |
| | 100 | 0 | 1 | 3 | 3 |
| 137 | 1000 | 1 | 2 | 2 | 3 |
| | 100 | 0 | 1 | 1 | 2 |
| 138 | 1000 | 0 | 0 | 2 | 2 |
| | 100 | 0 | 0 | 1 | 2 |
| 139 | 1000 | 1 | 3 | 3 | 3 |
| | 100 | 0 | 1 | 3 | 3 |
| 140 | 1000 | 2 | 3 | 3 | 3 |
| | 100 | 1 | 2 | 3 | 3 |
| 141 | 1000 | N/T | N/T | 3 | 3 |
| | 100 | N/T | N/T | 3 | 3 |
| 142 | 1000 | N/T | N/T | 2 | 3 |
| | 100 | N/T | N/T | 1 | 3 |
| 143 | 1000 | N/T | N/T | 0 | 2 |
| | 100 | N/T | N/T | 0 | 0 |
| 144 | 1000 | N/T | N/T | 3 | 3 |
| | 100 | N/T | N/T | 2 | 3 |
| 145 | 1000 | N/T | N/T | 3 | 3 |
| | 100 | N/T | N/T | 3 | 3 |
| 146 | 1000 | N/T | N/T | 2 | 3 |
| | 100 | N/T | N/T | 2 | 3 |
| 147 | 1000 | N/T | N/T | 3 | 3 |
| | 100 | N/T | N/T | 3 | 3 |
| 148 | 1000 | N/T | N/T | 2 | 2 |
| | 100 | N/T | N/T | 0 | 0 |
| 149 | 1000 | N/T | N/T | 3 | 3 |
| | 100 | N/T | N/T | 0 | 0 |
| 150 | 1000 | N/T | N/T | 3 | 3 |
| | 100 | N/T | N/T | 3 | 3 |
| 151 | 1000 | 0 | 0 | 0 | 1 |
| | 100 | 0 | 1 | 0 | 1 |
| 152 | 1000 | N/T | N/T | 0 | 2 |
| | 100 | N/T | N/T | 0 | 1 |
| 153 | 1000 | 0 | 2 | 2 | 3 |
| | 100 | 0 | 1 | 0 | 0 |
| 154 | 1000 | 0 | 2 | 0 | 1 |
| | 100 | 0 | 0 | 0 | 0 |
| 155 | 1000 | N/T | N/T | 1 | 2 |
| | 100 | N/T | N/T | 0 | 1 |
| 156 | 1000 | N/T | N/T | 3 | 3 |
| | 100 | N/T | N/T | 3 | 3 |
| 157 | 1000 | N/T | N/T | 3 | 3 |
| | 100 | N/T | N/T | 3 | 3 |
| 158 | 1000 | N/T | N/T | 3 | 3 |
| | 100 | N/T | N/T | 3 | 3 |
| 159 | 1000 | N/T | N/T | N/T | N/T |
| | 100 | N/T | N/T | 3 | 3 |
| 160 | 1000 | N/T | N/T | N/T | N/T |
| | 100 | N/T | N/T | 3 | 3 |
| 161 | 1000 | N/T | N/T | N/T | N/T |
| | 100 | N/T | N/T | 3 | 3 |
| 162 | 1000 | N/T | N/T | N/T | N/T |
| | 100 | N/T | N/T | 3 | 3 |
| 176 | 1000 | N/T | N/T | N/T | N/T |
| | 100 | N/T | N/T | 3 | 3 |
| 177 | 1000 | N/T | N/T | N/T | N/T |
| | 100 | N/T | N/T | 0* | 0*. |
| 177 | 1000 | N/T | N/T | 3 | 3 |
| | 100 | N/T | N/T | 3 | 3 |
| 258 | 1000 | N/T | N/T | N/T | N/T |
| | 100 | N/T | N/T | 3 | 3 |
| 274 | 1000 | N/T | N/T | 3 | 3 |
| | 100 | N/T | N/T | 3 | 3 |
| 281 | 1000 | N/T | N/T | N/T | N/T |
| | 100 | N/T | N/T | 3 | 3 |
| 309 | 1000 | N/T | N/T | 3 | 3 |
| | 100 | N/T | N/T | 3 | 3 |
| 310 | 1000 | N/T | N/T | 2 | 3 |
| | 100 | N/T | N/T | 1 | 3 |
| 311 | 1000 | N/T | N/T | 3 | 3 |
| | 100 | N/T | N/T | 3 | 3 |
| 313 | 1000 | N/T | N/T | 3 | 3 |
| | 100 | N/T | N/T | 3 | 3 |
| 314 | 1000 | N/T | N/T | 3 | 3 |
| | 100 | N/T | N/T | 3 | 3 |
| 315 | 1000 | N/T | N/T | N/T | N/T |
| | 100 | N/T | N/T | 1 | 2 |

*Test result was not valid because the active compound was not in solution.

The compounds of the present invention were also tested in the same procedure described above but at lower concentrations. In these tests, percent control was determined by counting the number of living larvae per dish and using Abbott's formula, [W. Abbott, "A Method of Computing the Effectiveness of an Insecticide", J. Econ. Entomol. 18, 265–267 (1925)]:

Percent Control =

$$\frac{\text{No. of survivors in control} - \text{No. of Survivors in treatment} \times 100}{\text{No. survivors in control}}$$

The results are set forth in Table 2, which follows.

TABLE 2

| Example No. | Appln. Rate ppm. | Insect Control Mexican Bean Beetle 4 days | 7 days | Southern Armyworm 4 days | 7 days |
|---|---|---|---|---|---|
| 7 | 100 | 0 | 7 | 100 | 100 |
| | 50 | 0 | 0 | 100 | 100 |
| | 25 | 0 | 0 | 100 | 100 |
| | 10 | 0 | 0 | 47 | 100 |
| 7 | 10 | N/T | N/T | 60 | 100 |
| | 5 | N/T | N/T | 40 | 100 |
| | 2.5 | N/T | N/T | 7 | 100 |
| | 1 | N/T | N/T | 0 | 13 |
| 7 | 1.0 | N/T | N/T | 0 | 60 |
| | .5 | N/T | N/T | 0 | 0 |
| | .25 | N/T | N/T | 0 | 0 |
| | 0.125 | N/T | N/T | 0 | 0 |
| 9 | 100 | N/T | N/T | 100 | 100 |
| | 50 | N/T | N/T | 100 | 100 |
| | 25 | N/T | N/T | 72 | 100 |
| | 10 | N/T | N/T | 60 | 100 |
| 9 | 10 | N/T | N/T | 100 | 100 |
| | 5 | N/T | N/T | 100 | 100 |
| | 2.5 | N/T | N/T | 67 | 100 |

TABLE 2-continued

| Example No. | Appln. Rate ppm. | Insect Control | | | |
|---|---|---|---|---|---|
| | | Mexican Bean Beetle | | Southern Armyworm | |
| | | 4 days | 7 days | 4 days | 7 days |
| | 1 | N/T | N/T | 0 | 60 |
| 13 | 100 | N/T | N/T | 100 | 100 |
| | 50 | N/T | N/T | 100 | 100 |
| | 25 | N/T | N/T | 100 | 100 |
| | 10 | N/T | N/T | 93 | 100 |
| 16 | 100 | N/T | N/T | 100 | 100 |
| | 50 | N/T | N/T | 100 | 100 |
| | 25 | N/T | N/T | 60 | 100 |
| | 10 | N/T | N/T | 27 | 47 |
| 24 | 100 | N/T | N/T | 100 | 100 |
| | 50 | N/T | N/T | 100 | 100 |
| | 25 | N/T | N/T | 100 | 100 |
| | 10 | N/T | N/T | 93 | 100 |
| 24 | 10 | 93 | 100 | N/T | N/T |
| | 5 | 71 | 93 | N/T | N/T |
| | 2.5 | 79 | 79 | N/T | N/T |
| | 1.0 | 0 | 0 | N/T | N/T |
| 25 | 100 | N/T | N/T | 0* | 0* |
| | 50 | N/T | N/T | 0* | 0* |
| 47 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 53 | 100 | N/T | N/T | 100 | 100 |
| | 50 | N/T | N/T | 100 | 100 |
| | 25 | N/T | N/T | 100 | 100 |
| | 10 | N/T | N/T | 47 | 100 |
| 53 | 10 | N/T | N/T | 100 | 100 |
| | 5 | N/T | N/T | 60 | 100 |
| | 2.5 | N/T | N/T | 60 | 100 |
| | 1 | N/T | N/T | 0 | 0 |
| 59 | 100 | 67 | 87 | 100 | 100 |
| | 50 | 33 | 60 | 87 | 100 |
| | 25 | 27 | 47 | 53 | 100 |
| | 10 | 0 | 7 | 20 | 72 |
| 61 | 100 | N/T | N/T | 67 | 100 |
| | 50 | N/T | N/T | 100 | 100 |
| | 25 | N/T | N/T | 53 | 100 |
| | 10 | N/T | N/T | 0 | 0 |
| 71 | 100 | N/T | N/T | 100 | 100 |
| | 10 | N/T | N/T | 100 | 100 |
| | 1.0 | N/T | N/T | 100 | 100 |
| | .5 | N/T | N/T | 100 | 100 |
| 71 | 1.0 | N/T | N/T | 100 | 100 |
| | .5 | N/T | N/T | 100 | 100 |
| | .25 | N/T | N/T | 100 | 100 |
| | .125 | N/T | N/T | 93 | 100 |
| 72 | 100 | N/T | N/T | 100 | 100 |
| | 50 | N/T | N/T | 20 | 40 |
| | 25 | N/T | N/T | 0 | 27 |
| | 10 | N/T | N/T | 0 | 7 |
| 76 | 100 | N/T | N/T | 100 | 100 |
| | 50 | N/T | N/T | 0 | 100 |
| | 25 | N/T | N/T | 0 | 53 |
| | 10 | N/T | N/T | 0 | 7 |
| 78 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 78 | 10 | N/T | N/T | 100 | 100 |
| | 5 | N/T | N/T | 80 | 100 |
| | 2.5 | N/T | N/T | 72 | 100 |
| | 1 | N/T | N/T | 20 | 60 |
| 78 | 10 | N/T | N/T | 100 | 100 |
| | 5 | N/T | N/T | 100 | 100 |
| | 2.5 | N/T | N/T | 87 | 100 |
| | 1 | N/T | N/T | 60 | 100 |
| 79 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 79 | 10 | N/T | N/T | 80 | 100 |
| | 5 | N/T | N/T | 47 | 100 |
| | 2.5 | N/T | N/T | 40 | 72 |
| | 1 | N/T | N/T | 0 | 27 |
| 79 | 10 | N/T | N/T | 100 | 100 |
| | 5 | N/T | N/T | 33 | 100 |
| | 2.5 | N/T | N/T | 72 | 87 |
| | 1 | N/T | N/T | 0 | 4 |
| 80 | 100 | N/T | N/T | 100 | 100 |
| | 50 | N/T | N/T | 100 | 100 |
| | 25 | N/T | N/T | 0 | 27 |
| | 10 | N/T | N/T | 0 | 0 |
| 83 | 100 | N/T | N/T | 100 | 100 |
| | 50 | N/T | N/T | 100 | 100 |
| | 25 | N/T | N/T | 100 | 100 |
| | 10 | N/T | N/T | 87 | 100 |
| 83 | 10 | N/T | N/T | 67 | 100 |
| | 5 | N/T | N/T | 60 | 93 |
| | 2.5 | N/T | N/T | 53 | 87 |
| | 1 | N/T | N/T | 0 | 0 |
| 83 | 10 | N/T | N/T | 100 | 100 |
| | 5 | N/T | N/T | 80 | 100 |
| | 2.5 | N/T | N/T | 33 | 100 |
| | 1 | N/T | N/T | 13 | 40 |
| 87 | 100 | N/T | N/T | 100 | 100 |
| | 50 | N/T | N/T | 100 | 100 |
| | 25 | N/T | N/T | 87 | 100 |
| | 10 | N/T | N/T | 20 | 53 |
| 94 | 10 | N/T | N/T | 0 | 0 |
| 95 | 50 | N/T | N/T | 100 | 100 |
| | 25 | N/T | N/T | 100 | 100 |
| | 10 | N/T | N/T | 67 | 100 |
| | 1.0 | N/T | N/T | 0 | 13 |
| 95 | 1.0 | N/T | N/T | 0 | 27 |
| | .5 | N/T | N/T | 7 | 7 |
| | .25 | N/T | N/T | 0 | 0 |
| | .125 | N/T | N/T | 0 | 0 |
| 97 | 50 | N/T | N/T | 100 | 100 |
| | 25 | N/T | N/T | 100 | 100 |
| | 10 | N/T | N/T | 100 | 100 |
| | 1.0 | N/T | N/T | 40 | 100 |
| 97 | 1.0 | N/T | N/T | 72 | 100 |
| | .5 | N/T | N/T | 0 | 33 |
| | .25 | N/T | N/T | 0 | 20 |
| | .125 | N/T | N/T | 0 | 7 |
| 98 | 100 | 20 | 100 | 100 | 100 |
| | 50 | N/T | N/T | 100 | 100 |
| | 25 | N/T | N/T | 100 | 100 |
| | 10 | 0 | 100 | 100 | 100 |
| 98 | 10 | N/T | N/T | 100 | 100 |
| | 5 | N/T | N/T | 100 | 100 |
| | 2.5 | N/T | N/T | 80 | 100 |
| | 1.0 | N/T | N/T | 0 | 53 |
| 99 | 100 | 13 | 100 | 100 | 100 |
| | 50 | N/T | N/T | 100 | 100 |
| | 25 | N/T | N/T | 100 | 100 |
| | 10 | 7 | 100 | 100 | 100 |
| 99 | 10 | N/T | N/T | 100 | 100 |
| | 5 | N/T | N/T | 100 | 100 |
| | 2.5 | N/T | N/T | 100 | 100 |
| | 1.0 | N/T | N/T | 0 | 60 |
| 99 | 1.0 | N/T | N/T | 7 | 47 |
| | .5 | N/T | N/T | 0 | 0 |
| | .25 | N/T | N/T | 0 | 0 |
| | .125 | N/T | N/T | 0 | 0 |
| 108 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 108 | 10 | N/T | N/T | 100 | 100 |
| | 5.0 | N/T | N/T | 100 | 100 |
| | 2.5 | N/T | N/T | 100 | 100 |
| | 1.0 | N/T | N/T | 33 | 87 |
| 109 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 109 | 10 | N/T | N/T | 100 | 100 |
| | 5.0 | N/T | N/T | 100 | 100 |
| | 2.5 | N/T | N/T | 100 | 100 |
| | 1 | N/T | N/T | 100 | 100 |
| 109 | 0.5 | N/T | N/T | 47 | 9 |
| | 0.25 | N/T | N/T | 0 | 13 |

TABLE 2-continued

| Example No. | Appln. Rate ppm. | Insect Control | | | |
|---|---|---|---|---|---|
| | | Mexican Bean Beetle | | Southern Armyworm | |
| | | 4 days | 7 days | 4 days | 7 days |
| | 0.125 | N/T | N/T | 0 | 20 |
| | 0.063 | N/T | N/T | 0 | 20 |
| 110 | 100 | N/T | N/T | 100 | 100 |
| | 50 | N/T | N/T | 100 | 100 |
| | 25 | N/T | N/T | 60 | 87 |
| | 10 | N/T | N/T | 27 | 40 |
| 114 | 100 | 0 | 0 | 100 | 100 |
| | 50 | N/T | N/T | 100 | 100 |
| | 25 | N/T | N/T | 100 | 100 |
| | 10 | 0 | 0 | 100 | 100 |
| 114 | 10 | N/T | N/T | 100 | 100 |
| | 5 | N/T | N/T | 100 | 100 |
| | 2.5 | N/T | N/T | 80 | 100 |
| | 1.0 | N/T | N/T | 0 | 53 |
| 125 | 100 | N/T | N/T | 100 | 100 |
| | 10 | N/T | N/T | 53 | 80 |
| | 5 | N/T | N/T | 13 | 47 |
| | 1 | N/T | N/T | 0 | 0 |
| 125 | 100 | N/T | N/T | 100 | 100 |
| | 50 | N/T | N/T | 100 | 100 |
| | 10 | N/T | N/T | 27 | 40 |
| | 1 | N/T | N/T | 0 | 0 |
| 125 | 100 | N/T | N/T | 87 | 100 |
| | 50 | N/T | N/T | 87 | 100 |
| | 25 | N/T | N/T | 13 | 40 |
| | 10 | N/T | N/T | 0 | 0 |
| 125 | 100 | N/T | N/T | 100 | 100 |
| | 10 | N/T | N/T | 53 | 80 |
| | 5 | N/T | N/T | 13 | 47 |
| | 1.0 | N/T | N/T | 0 | 0 |
| 127 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 127 | 10 | N/T | N/T | 80 | 100 |
| | 5 | N/T | N/T | 87 | 100 |
| | 2.5 | N/T | N/T | 67 | 100 |
| | 1.0 | N/T | N/T | 0 | 7 |
| 129 | 50 | N/T | N/T | 100 | 100 |
| | 25 | N/T | N/T | 100 | 100 |
| | 10 | N/T | N/T | 100 | 100 |
| | 1.0 | N/T | N/T | 20 | 40 |
| 130 | 100 | 67 | 100 | 100 | 100 |
| | 50 | N/T | N/T | 100 | 100 |
| | 25 | N/T | N/T | 100 | 100 |
| | 10 | 7 | 27 | 100 | 100 |
| 130 | 10 | N/T | N/T | 100 | 100 |
| | 5 | N/T | N/T | 100 | 100 |
| | 2.5 | N/T | N/T | 100 | 100 |
| | 1.0 | N/T | N/T | 33 | 72 |
| 130 | 1.0 | N/T | N/T | 33 | 93 |
| | .5 | N/T | N/T | 0 | 0 |
| | .25 | N/T | N/T | 0 | 0 |
| | .125 | N/T | N/T | 0 | 0 |
| 131 | 100 | 33 | 100 | N/T | N/T |
| | 50 | N/T | N/T | N/T | N/T |
| | 25 | N/T | N/T | N/T | N/T |
| | 10 | 0 | 100 | N/T | N/T |
| 131 | 1.0 | N/T | N/T | 20 | 20 |
| | .5 | N/T | N/T | 0 | 0 |
| | .25 | N/T | N/T | 0 | 0 |
| | .125 | N/T | N/T | 0 | 0 |
| 132 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 132 | 10 | N/T | N/T | 80 | 100 |
| | 5 | N/T | N/T | 80 | 87 |
| | 2.5 | N/T | N/T | 27 | 60 |
| | 1.0 | N/T | N/T | 20 | 27 |
| 134 | 1.0 | N/T | N/T | 100 | 100 |
| | .5 | N/T | N/T | 72 | 87 |
| | .25 | N/T | N/T | 0 | 60 |
| | .125 | N/T | N/T | 0 | 0 |
| 134 | 1.0 | N/T | N/T | 100 | 100 |
| | .5 | N/T | N/T | 100 | 100 |
| | .25 | N/T | N/T | 100 | 100 |
| | .125 | N/T | N/T | 40 | 93 |
| 135 | 100 | N/T | N/T | 100 | 100 |
| | 10 | N/T | N/T | 100 | 100 |
| | 1.0 | N/T | N/T | 53 | 100 |
| | .5 | N/T | N/T | 67 | 100 |
| 135 | 1.0 | N/T | N/T | 100 | 100 |
| | .5 | N/T | N/T | 100 | 100 |
| | .25 | N/T | N/T | 72 | 100 |
| | .125 | N/T | N/T | 67 | 100 |
| 136 | 100 | N/T | N/T | 100 | 100 |
| | 50 | N/T | N/T | 100 | 100 |
| | 25 | N/T | N/T | 100 | 100 |
| | 10 | N/T | N/T | 20 | 40 |
| 137 | 100 | N/T | N/T | 60 | 100 |
| | 50 | N/T | N/T | 87 | 93 |
| | 25 | N/T | N/T | 53 | 63 |
| | 10 | N/T | N/T | 40 | 50 |
| 139 | 100 | N/T | N/T | 93 | 100 |
| | 50 | N/T | N/T | 87 | 100 |
| | 25 | N/T | N/T | 72 | 100 |
| | 10 | N/T | N/T | 60 | 100 |
| 139 | 10 | N/T | N/T | 100 | 100 |
| | 5 | N/T | N/T | 72 | 93 |
| | 2.5 | N/T | N/T | 67 | 80 |
| | 1 | N/T | N/T | 0 | 80 |
| 140 | 100 | N/T | N/T | 100 | 100 |
| | 50 | N/T | N/T | 60 | 100 |
| | 25 | N/T | N/T | 87 | 100 |
| | 10 | N/T | N/T | 7 | 23 |
| 141 | 1.0 | N/T | N/T | 100 | 100 |
| | .5 | N/T | N/T | 80 | 93 |
| | .25 | N/T | N/T | 53 | 53 |
| | .125 | N/T | N/T | 0 | 27 |
| 142 | 100 | N/T | N/T | 40 | 87 |
| | 50 | N/T | N/T | 33 | 93 |
| | 25 | N/T | N/T | 0 | 0 |
| | 10 | N/T | N/T | 0 | 0 |
| 144 | 100 | N/T | N/T | 87 | 100 |
| | 50 | N/T | N/T | 80 | 100 |
| | 25 | N/T | N/T | 13 | 27 |
| | 10 | N/T | N/T | 0 | 0 |
| 145 | 100 | N/T | N/T | 100 | 100 |
| | 50 | N/T | N/T | 60 | 67 |
| | 25 | N/T | N/T | 27 | 40 |
| | 10 | N/T | N/T | 7 | 20 |
| 146 | 100 | N/T | N/T | 40 | 100 |
| | 50 | N/T | N/T | 27 | 67 |
| | 25 | N/T | N/T | 0 | 53 |
| | 10 | N/T | N/T | 0 | 13 |
| 147 | 100 | N/T | N/T | 100 | 100 |
| | 50 | N/T | N/T | 100 | 100 |
| | 25 | N/T | N/T | 100 | 100 |
| | 10 | N/T | N/T | 67 | 100 |
| 150 | 100 | N/T | N/T | 100 | 100 |
| | 50 | N/T | N/T | 100 | 100 |
| | 25 | N/T | N/T | 60 | 100 |
| | 10 | N/T | N/T | 7 | 100 |
| 150 | 10 | N/T | N/T | 100 | 100 |
| | 5 | N/T | N/T | 60 | 100 |
| | 2.5 | N/T | N/T | 60 | 100 |
| | 1 | N/T | N/T | 0 | 0 |
| 156 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 156 | 10 | N/T | N/T | 100 | 100 |
| | 5 | N/T | N/T | 100 | 100 |
| | 2.5 | N/T | N/T | 80 | 100 |
| | 1 | N/T | N/T | 20 | 93 |
| 156 | 10 | N/T | N/T | 100 | 100 |
| | 5 | N/T | N/T | 100 | 100 |
| | 2.5 | N/T | N/T | 100 | 100 |
| | 1 | N/T | N/T | 33 | 100 |
| 156 | 1.0 | N/T | N/T | 53 | 100 |
| | 0.5 | N/T | N/T | 13 | 40 |
| | 0.25 | N/T | N/T | 0 | 13 |
| | 0.125 | N/T | N/T | 0 | 15 |

TABLE 2-continued

| Example No. | Appln. Rate ppm. | Insect Control | | | |
|---|---|---|---|---|---|
| | | Mexican Bean Beetle | | Southern Armyworm | |
| | | 4 days | 7 days | 4 days | 7 days |
| 157 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |
| 157 | 10 | N/T | N/T | 100 | 100 |
| | 5 | N/T | N/T | 100 | 100 |
| | 2.5 | N/T | N/T | 100 | 100 |
| | 1 | N/T | N/T | 72 | 87 |
| 157 | 1.0 | N/T | N/T | 60 | 80 |
| | .5 | N/T | N/T | 47 | 53 |
| | .25 | N/T | N/T | 0 | 0 |
| | .125 | N/T | N/T | 0 | 0 |
| 158 | 100 | N/T | N/T | 100 | 100 |
| | 50 | N/T | N/T | 100 | 100 |
| | 25 | N/T | N/T | 100 | 100 |
| | 10 | N/T | N/T | 100 | 100 |

The rating code (percent of control) used below is as follows:
0 = 0%
1 = 1-50%
2 = 51-99%
3 = 100%
N/T = Not Tested

| Example No. | Appln. Rate ppm. | 4 days | 7 days | 4 days | 7 days |
|---|---|---|---|---|---|
| 159 | 10 | N/T | N/T | 3 | 3 |
| | 1 | N/T | N/T | 3 | 3 |
| 160 | 10 | N/T | N/T | 3 | 3 |
| | 1 | N/T | N/T | 2 | 3 |
| 161 | 10 | N/T | N/T | 3 | 3 |
| | 1 | N/T | N/T | 1 | 2 |
| 162 | 10 | N/T | N/T | 3 | 3 |
| | 1 | N/T | N/T | 0 | 1 |
| 176 | 10 | N/T | N/T | 3 | 3 |
| | 1 | N/T | N/T | 1 | 2 |
| 177 | 10 | N/T | N/T | 0* | 0* |
| | 1 | N/T | N/T | N/T | N/T |
| 258 | 10 | N/T | N/T | 0 | 1 |
| 274 | 10 | N/T | N/T | 3 | 3 |
| | 1 | N/T | N/T | 2 | 3 |
| 281 | 10 | N/T | N/T | 3 | 3 |
| | 1 | N/T | N/T | 1 | 2 |
| 309 | 10 | N/T | N/T | 3 | 3 |
| | 1 | N/T | N/T | 2 | 3 |
| 310 | 10 | N/T | N/T | 0 | 0 |
| | 1 | N/T | N/T | 0 | 0 |
| 311 | 10 | N/T | N/T | 3 | 3 |
| | 1 | N/T | N/T | 1 | 2 |
| 313 | 10 | N/T | N/T | 3 | 3 |
| | 1 | N/T | N/T | 1 | 3 |
| 314 | 10 | N/T | N/T | 2 | 3 |
| | 1 | N/T | N/T | 1 | 3 |
| 315 | 10 | N/T | N/T | 0 | 0 |
| | 1 | N/T | N/T | 0 | 0 |

*Test result was not valid because the active compound was not in solution.

A test was done to determine the ovicidal activity of a representative compound of the present invention against the eggs of a typical insect such as, for example, Egyptian cotton leafworm (*Spodoptera littoralis*). In this test the adult insects were allowed to lay their eggs on filter paper. The eggs were treated by dipping the filter paper containing the eggs into solutions of the test compound which were prepared by dissolving 10 mg. of the test compound in 1 ml. of a solvent which per liter contained 50 percent V/V each of acetone and ethanol and 23 g. of Toximol R and 13 g. of Toximol S. The dissolved test compound was dispersed in 9 ml. of distilled water to make up a stock dispersion containing 500 mg./L. Lower concentrations were made by preparing dilutions of the stock dispersion. The test compound was evaluated at concentrations of 500 mg./L. and 50 mg./L. and the test compound was that of Example 71. The results of the experiment showed that at two and six days after treatment at 500 mg./L., the ovicidal effect was 10 percent and 100 percent respectively. At 50 mg./L. over the same time interval, the ovicidal effect was somewhat reduced although still at 2 percent and 95 percent respectively.

The chemosterilant activity of the present compounds was determined by dissolving a representative compound in acetone and then dipping adult boll weevils (*Anthonomus grandis*) into the solution. The treated insects were air dried and cultured under controlled conditions. Eggs were collected and the chemosterilant activity was determined by comparing the number of nonviable eggs collected from the treating adults with the number of nonviable eggs collected from a control group. The mean mortality of the adults in both the treated and control groups was also determined. The results are presented below in Table 3. The percent control was defined as follows:

$$1 - \frac{\text{No. of viable eggs from treated adults}}{\text{No. of viable eggs from control adults}} \cdot 100$$

TABLE 3

| | | Chemosterilant Activity Against Boll Weevil | | | | | |
|---|---|---|---|---|---|---|---|
| Example No. | Days after Treatment | Ovicidal Activity Percent Control Appln. Rate 2000 ppm | Mean Adult Mortality* Appln. Rate 2000 ppm | Mean Nonviable Eggs** Appln. Rate (ppm) | | | |
| | | | | 1000 | 500 | 250 | 100 |
| 71 | 4 | | 7 | | | | |
| | 7 | | 7 | | | | |
| | 8 | | 10 | | | | |
| | 9 | 0 | 10 | | | | |
| | 10 | 0 | | | | | |
| | 10 | 0 | | 6 | 7 | 6 | 5 |
| | 11 | 94 | | | | | |
| | 11 | 100 | | | | | |
| | 13 | | | 6 | 2 | 6 | 5 |
| | 13 | | | 3 | 1 | 7 | 5 |
| | 14 | 100 | | | | | |
| | 14 | 100 | | | | | |

*Control mean = 2 at 4, 7, 8, and 9 days after treatment
**Control mean = <1 at 10 and 13 days after treatment The insecticidal activity of the compounds of the present invention was further evaluated by additional testing. Solutions of varying concentration of active compounds (prepared in the manner described in the introductory material preceding Tables 1 and 2 above) were sprayed to the point of run-off on Chinese cabbage (*Brassica pekinensis*) growing under controlled conditions. The cabbage was allowed to dry for 24 hours and then leaf discs (portions of the leaves) were fed to 50 second instar larvae of Egyptian cotton leafworm (*Spodoptera littoralis*) in petri dishes under controlled conditions. The leaf discs were changed as often as was necessary to maintain cleanliness and an adequate food supply. The percent control was determined at 2, 3, 5, and 8-day intervals as follows:

$$\frac{\text{No. of dead treated larvae} - \text{No. of dead control larvae}}{100 - \text{No. of surviving control larvae}}$$

The plants from which the leaf discs were obtained were bottom watered after spraying so as to avoid erosion of the insecticides. The results obtained for representative compounds of the present invention are given in Table 4.

TABLE 4

| Example No. | Appln. Rate mg./L. | Percent Control of Egyptian Cotton Leafworm | | | |
|---|---|---|---|---|---|
| | | 2 Days After Treatment | 3 Days After Treatment | 5 Days After Treatment | 8 Days After Treatment |
| 7 | 10 | 24 | 33 | 82 | 100 |
| | 25 | 15 | 42 | 98 | 100 |
| | 50 | 26 | 83 | 100 | 100 |
| | 100 | 27 | 71 | 100 | 100 |
| 24 | 10 | 6 | 6 | 3 | 0 |
| | 25 | 0 | 0 | 3 | 17 |
| | 50 | 0 | 2 | 3 | 1 |
| | 100 | 0 | 2 | 7 | 0 |
| 71 | 10 | 15 | 82 | 96 | 100 |
| | 25 | 12 | 79 | 96 | 100 |
| | 50 | 15 | 93 | 100 | 100 |
| | 100 | 9 | 93 | 100 | 100 |
| 109 | 10 | 13 | 49 | 88 | 100 |
| | 25 | 16 | 61 | 88 | 100 |
| | 50 | 21 | 74 | 96 | 100 |
| | 100 | 33 | 76 | 98 | 100 |
| 111 | 10 | 11 | 44 | 84 | 98 |
| | 25 | 23 | 54 | 91 | 100 |
| | 50 | 39 | 60 | 98 | 100 |
| | 100 | 41 | 70 | 92 | 100 |
| 130 | 10 | 3 | 14 | 88 | 100 |
| | 25 | 23 | 64 | 96 | 100 |
| | 50 | 31 | 74 | 93 | 100 |
| | 100 | 5 | 8 | 93 | 100 |
| 131 | 10 | 0 | 9 | 88 | 100 |
| | 25 | 1 | 21 | 88 | 100 |
| | 50 | 5 | 21 | 86 | 100 |
| | 100 | 1 | 16 | 87 | 100 |
| 147 | 10 | 0 | 4 | 5 | 0 |
| | 25 | 0 | 0 | 3 | 9 |
| | 50 | 1 | 2 | 0 | 0 |
| | 100 | 0 | 4 | 18 | 4 |

The above procedure was modified by using leaf discs obtained from cabbage plants growing under field conditions. The results (scored as above and presented below) show the residual insecticidal activity of a representative compound of the present invention.

| Percent Control of Egyptian Cotton Leafworm | | |
|---|---|---|
| Example No. | Days After Treatment | Appln. Rate 100 mg./L. |
| 71 | 3 | 96 |
| | 5 | 100 |
| | 8 | 100 |
| | 9 | 46 |
| | 11 | 98 |
| | 13 | 70 |
| | 14 | 100 |
| | 15 | 100 |
| | 17 | 87 |
| | 18 | 100 |
| | 19 | 100 |
| | 20 | 100 |
| | 22 | 100 |
| | 22 | 98 |
| | 23 | 80 |
| | 25 | 100 |
| | 25 | 100 |
| | 28 | 100 |

The insecticidal activity of the compounds of the present invention on tobacco budworm (*Heliosis virescens*) under field conditions was determined by spraying varying amounts of an active compound (formulated at 50% active ingredient as described previously in formulation Example A) to the point of run-off on upland cotton (*Gossypium* sp.). The number of tobacco budworms on the plant terminals and the number of fruits undamaged by insects were calculated at varying times after treatment. The results were expressed as the percent control which was defined as follows:

$$1 - \frac{\text{No. of worms on treated plants}}{\text{No. of worms on control plants}} \cdot 100 \text{ or}$$

$$1 - \frac{\text{No. of undamaged fruits on treated plants}}{\text{No. of undamaged fruits on control plants}} \cdot 100$$

The results for representative compounds are presented in Table 5 below.

TABLE 5

| Field Insecticidal Activity Against Tobacco Budworm | | | | |
|---|---|---|---|---|
| | | Percent Control of Worms On Plant Terminals | | Percent Control of Insect Damage |
| Example No. | Appln. Rate lbs./acre | 12 Days after Treatment | 17 Days after Treatment | to Fruit 12 Days After Treatment |
| 7 | .25 | 33 | | 78 |
| | .5 | 100 | | 78 |
| | 1.0 | 0 | | 75 |
| 71 | .25 | | 0 | |
| | .5 | | 44 | |
| | 1.0 | | 0 | |

The above field procedure was repeated on tomatoes (*Lycopersicon*) and the number of insect damaged fruits on the tested and control plants was calculated. The results are presented in Table 6 below.

TABLE 6

| Field Insecticidal Activity Against Tobacco Budworm | | |
|---|---|---|
| | Percent Control Of Insect Fruit Damage | |
| Example No. | Appln. Rate lbs./Acre | 15 Days After Treatment | 23 Days After Treatment |
| 7 | .125 | 17 | — |
| | .25 | 21 | — |
| | .5 | 6 | — |
| | 1.0 | 0 | 0 |

A representative compound of the present invention was tested against the cabbage looper (Trichoplusia NI). The compound was formulated as a wettable powder (containing 50% active ingredient as described previously in formulation Example A) and tested in the manner described in the introductory material preceding Table 4 except that soybean (*Glycine max*) plants growing under field conditions were used. The number of surviving larvae which fed on the treated and the control soybean leaves was calculated and expressed as a percent control. The percent control was defined as follows:

$$\frac{\text{No. of surviving treated larvae}}{\text{No. of surviving control larvae}} \cdot 100$$

The results are presented below in Table 7.

TABLE 7

| | | Percent Control Of Cabbage Looper | | |
|---|---|---|---|---|
| Example No. | Appln. Rate ppm. | 2 Days After Treatment | 4 Days After Treatment | 5 Days After Treatment |
| 7 | 1000 | | | 22 |
| | 100 | | | 44 |

Additional testing of the compounds against cabbage looper was also done. Sprouting broccoli (*Brassica oleracea*) plants were treated in a manner which was substantially similar to that described in the introductory material preceding Table 5. The insecticidal activity was determined by counting the number of larvae on both the treated and the control plants. The results were expressed as a percent control which was defined as follows:

$$1 - \frac{\text{No. of larvae on treated plants}}{\text{No. of larvae on control plants}} \cdot 100$$

The procedure was repeated using sugar beet plants to test for activity against beet armyworm (*Spodoptera exigna*). The results for both the cabbage looper and the beet armyworm field tests are presented in Table 8.

TABLE 8

| | | Percent Control Of Cabbage Looper | | | | | |
|---|---|---|---|---|---|---|---|
| | | 6 Days After Treatment | | | 13 Days After Treatment | | |
| Example No. | Appln. Rate lbs/Acre | Larvae ⅛-¾" long | Larvae <⅛" long | Larvae >¾" long | Larvae ⅛-¾" long | Larvae <⅛" long | Larvae >¾" long |
| 7 | .125 | 14 | 57 | 0 | 100 | 0 | 25 |
| | .25 | 57 | 0 | 0 | 33 | 82 | 50 |
| | .5 | 57 | 0 | 0 | 66 | 11 | 0 |
| | 1.0 | 100 | 78 | 0 | 100 | 0 | 50 |

| | | Percent Control Of Beet Army Worm |
|---|---|---|
| | | 5 Days After Treatment |
| 7 | .125 | 100 |
| | .25 | 100 |
| | .5 | 100 |
| | 1.0 | 33 |

The compounds of the present invention were also tested against housefly (*Musca domestica*) under controlled conditions. The compounds were formulated in a manner which was substantially similar to that described in the introductory material preceding Table 1. The resultant test formulations were mixed with an artificial medium so that the final concentration of the active ingredient in the medium was either 2 ppm. or 1 ppm. The treated medium was placed in a culture dish and 25 house fly eggs were added. The eggs quickly hatched and the active ingredient was ingested with the feed. Various artificial media are known in the art and the selection of a particular medium, which is suitable for the culture of house fly, is not significant. After 14 days the number of adult house flies was counted and the percent control calculated. The percent control was determined by using Abbott's formula as described in the introductory material preceding Table 2.

The results are set forth below in Table 9.

TABLE 9

| Example No. | Appln. Rate ppm. | Insecticidal Activity Against House Fly Percent Control After 14 Days |
|---|---|---|
| 7 | 2 | 0 |
| 13 | 2 | 72 |
| | 1 | 32 |
| 16 | 2 | 2 |
| 34 | 2 | 0 |
| 40 | 2 | 0 |
| | 1 | 0 |
| 47 | 2 | 100 |
| | 1 | 96 |
| 53 | 2 | 38 |
| 59 | 2 | 2 |
| 71 | 2 | 98 |
| | 1 | — |
| 72 | 2 | 0 |
| 73 | 2 | 96 |
| 76 | 2 | 16 |
| 78 | 2 | 100 |
| | 1 | — |
| 86 | 2 | 100 |
| | 2 | 76 |
| | 1 | 0 |
| 87 | 2 | 8 |
| 88 | 2 | 36 |
| | 1 | — |
| 91 | 2 | 0 |
| 92 | 2 | 0 |
| 93 | 2 | 0 |
| 94 | 2 | 0 |
| | 1 | 0 |
| 95 | 2 | 76 |
| | 1 | 72 |
| 96 | 1 | 98 |
| 97 | 2 | 60 |
| | 1 | 0 |
| 98 | 2 | 0 |
| | 1 | 0 |
| 99 | 2 | 92 |
| | 1 | 60 |
| 100 | 2 | 40 |
| 101 | 2 | 18 |
| 103 | 2 | 0 |
| 104 | 2 | 64 |
| | 2 | 30 |
| | 1 | 0 |
| 105 | 2 | 58 |
| 108 | 2 | 4 |
| | 1 | 0 |
| 109 | 1 | 86 |
| 110 | 2 | 0 |
| 111 | 2 | 100 |
| | 1 | 100 |
| 112 | 2 | 96 |
| 113 | 1 | 90 |
| 114 | 2 | 36 |
| 115 | 2 | 0 |
| 116 | 2 | 16 |
| 117 | 2 | 0 |
| 118 | 2 | 0 |
| 119 | 2 | 0 |
| | 1 | 0 |
| 120 | 2 | 0 |
| | 1 | — |
| 121 | 2 | 44 |
| 122 | 2 | 22 |
| 123 | 2 | 0 |
| 125 | 2 | 28 |
| | 1 | — |
| 126 | 1 | 92 |
| 127 | 2 | 100 |
| 128 | 2 | 94 |
| | 1 | 82 |
| 129 | 2 | 100 |
| | 1 | 90 |

TABLE 9-continued

| Example No. | Appln. Rate ppm. | Insecticidal Activity Against House Fly Percent Control After 14 Days |
|---|---|---|
| 130 | 1 | 96 |
| 131 | 2 | 0 |
|  | 1 | 0 |
| 132 | 2 | 76 |
|  | 1 | — |
| 133 | 2 | 0 |
|  | 1 | 0 |
| 134 | 2 | 92 |
|  | 1 | — |
| 135 | 2 | 94 |
|  | 1 | — |
| 137 | 2 | 2 |
| 139 | 2 | 18 |
| 141 | 2 | 0 |
|  | 1 | 0 |
| 142 | 2 | 22 |
| 144 | 2 | 8 |
| 145 | 2 | 13 |
| 146 | 2 | 37 |
| 147 | 2 | 48 |
| 150 | 2 | 0 |
| 153 | 2 | 9 |
| 155 | 2 | 0 |
|  | 1 | 0 |
| 156 | 2 | 80 |
| 157 | 2 | 34 |
| 158 | 2 | 28 |

The compounds of the present invention were tested against corn earworm (*Heliothis zea*) in a manner which was similar to that described in the introductory material preceding Tables 1 and 2 except that treated corn plants, rather than treated bean plants, were used. The concentration of the active ingredient was at 10, 50 or 100 ppm. and the percent control was determined by counting the number of living larvae per dish using Abbott's formula as previously defined in the introductory material preceding Table 2.

The results are set forth in Table 10, which follows.

TABLE 10

| Example No. | Appln. Rate ppm. | Percent Control of Corn Earworm 7 Days After Treatment |
|---|---|---|
| 7 | 50 | 0 |
| 9 | 100 | 23 |
| 13 | 50 | 88 |
| 32 | 50 | 100 |
| 71 | 50 | 90 |
| 73 | 50 | 100 |
| 78 | 50 | 14 |
| 97 | 50 | 93 |
| 98 | 50 | 8 |
| 99 | 100 | 93 |
| 105 | 50 | 86 |
| 108 | 50 | 22 |
| 109 | 50 | 44 |
| 111 | 50 | 73 |
| 112 | 50 | 60 |
| 113 | 50 | 58 |
| 121 | 50 | 0 |
| 127 | 10 | 100 |
| 130 | 50 | 100 |
| 131 | 50 | 100 |
| 132 | 50 | 0 |
| 135 | 50 | 90 |
| 156 | 100 | 54 |
| 157 | 50 | 87 |

Representative compounds of the present invention, formulated in a manner which was substantially similar to that described in the introductory material preceding Tables 1 and 2, were tested against mosquito (*Aedes aegypti*) under laboratory conditions. The test solution was diluted so that the final concentration of the active agent ranged from about 20 to 0.001 ppm. The test solution was then placed in a standard culture jar and 20 five-day-old larvae were added. Conventional culture procedures were followed and on the 2nd and 9th days after treatment, the larvae were fed.

Insecticidal effect was determined by counting the number of living larvae per jar. All the treatments were compared to solvent controls and nontreated controls. The rating code (percent control) used was as follows:

0=0%
1=10–20%
2=20–30%
4=40–50%
5=50–60%
6=60–70%
7=70–80%
8=80–90%
9=90–100%
9+ =100%

The results of this test are set forth in Table 11 which follows:

TABLE 11

Percent Control Of Mosquito 14 Days After Treatment at Varying Concentrations

| Example No. | 2 ppm. | 1 ppm. | 0.1 ppm. | 0.01 ppm. | 0.005 ppm. | 0.003 ppm. | 0.001 ppm. |
|---|---|---|---|---|---|---|---|
| 71 |  |  |  | 9+ | 9 | 9 | 7 |
|  |  |  |  | 9 | 9+ | 9 | 7 |
| 78 | 4 | 7 |  | 4 | 7 |  |  |
|  | 7 | 1 |  | 5 | 1 |  |  |
|  | 5 | 1 |  |  |  |  |  |
| 96 | 0 | 5 | 0 |  |  |  |  |
|  | 0 |  |  |  |  |  |  |
| 108 |  |  |  | 9+ | 5 |  |  |
|  |  |  |  | 8 | 5 |  |  |
| 109 |  |  |  | 9+ | 9+ |  |  |
|  |  |  |  | 8 | 8 |  |  |
|  |  |  |  | 8 | 9+ |  |  |
|  |  |  |  |  | 9+ |  |  |
|  |  |  |  |  | 8 |  |  |
|  |  |  |  |  | 9+ |  |  |
| 109 |  |  |  | 9+ | 9+ | 9+ | 3 |
|  |  |  |  | 9+ | 9+ | 9+ | 0 |
|  |  |  |  |  | 9+ | 9+ |  |
| 113 |  |  |  | 9+ | 9 |  |  |
| 129 | 0 | 2 | 2 |  |  |  |  |
|  | 2 |  |  |  |  |  |  |
| 130 | 0 | 2 | 5 |  |  |  |  |
|  | 0 |  |  |  |  |  |  |
| 147 |  |  | 9+ | 4 | 0 |  |  |
| 150 |  |  | 9 | 1 | 0 |  |  |
| 156 |  |  | 9+ | 3 | 2 |  |  |
| 157 |  |  | 9+ | 5 | 0 |  |  |

The feedthrough insecticidal activity of a representative compound of the present invention was tested and the larvicidal activity against housefly (*Musca domestica*) in fecal material was determined. Accordingly, the test compound was administered orally to 36 Hubbard boiler breeder chickens in wire cage pens that had fecal dropping trays. Water was supplied in a watering trough attached to the rear of the cage and feed was offered ad libitum in troughs fastened to the front of the pen.

The feed consisted of a basal ration that is similar to the type ordinarily fed to chickens. The composition of the test feed is disclosed below.

| Basal Feed Ration | | |
|---|---|---|
| Ingredients | Percent | LBS/ton |
| Corn, Yellow, Ground | 54.30 | 1086 |

| Basal Feed Ration | | |
|---|---|---|
| Ingredients | Percent | LBS/ton |
| Soybean Meal, Solvent Extracted, Dehulled (50%) | 12.70 | 254 |
| Oats, Ground Whole | 8.00 | 160 |
| Calcium Carbonate (Ground Limestone) | 7.20 | 144 |
| Wheat Middlings | 5.00 | 100 |
| Corn Distillers Dried Solubles | 5.00 | 100 |
| Alfalfa Meal, Dehydrated (17%) | 2.50 | 50 |
| Fish Meal with Solubles | 2.00 | 40 |
| Dicalcium Phosphate, Feed Grade | 1.50 | 30 |
| Animal Fat | 0.65 | 13 |
| Vitamin Premix TK-01(1.03)* | 0.50 | 10 |
| Salt (NaCl) | 0.30 | 6 |
| Methionine Hydroxy Analog | 0.25 | 5 |
| Trace Mineral Premix TK-01(1.02)** | 0.10 | 2 |
| Total | 100.00 | 2000 |

*Provides 3000 IU of vitamin A, 900 ICU of vitamin D, 40 mg. of vitamin E, 0.7 mg. of vitamin K, 1000 mg. of choline, 70 mg. of niacin, 4 mg. of pantothenic acid, 4 mg. of riboflavin, 0.10 mg. of vitamin $B_{12}$, 0.10 mg. of biotin, and 125 mg. of ethoxyquin per kg. of complete feed.
**Provides 75 mg. of manganese, 50 mg. of zinc, 25 mg. of iron, and 1 mg. of iodine per kg. of complete feed.

The above feed was medicated by mixing with the test compound and thus medicated feeds with varying concentrations of the active ingredient were prepared.

The concentration of the active compound in the test diet was 3.8, 7.5, and 15 ppm and feed at each concentration level was fed to at least 4 birds divided into at least 2 pens providing replicate groups per concentration. Birds were randomly allotted to the 3 treatments with 4 nontreated birds divided into 2 groups to serve as negative controls.

The birds were fed ad libitum with the medicated rations. At the end of 6 weeks all medicated feeds were withdrawn and the nonmedicated basal ration was placed in the feeders for an additional 3 weeds.

Approximately 500 grams of feces were collected on the mornings of test days 0, 7, 14, 21, 28, 35, 42, 49, 56, and 63 from each pen. The fecal samples were properly identified and stored in a cold room at 34° F. until bioassayed for insecticidal activity. About 50 ml. of water were mixed with each 500 gram fecal sample in one quart plastic containers and 100 housefly eggs were seeded on each manure sample. The thus prepared samples were covered with muslin and maintained at room temperature until evaluated. Larval development, pupal formation, and adult emergence were observed and recorded.

Insecticidal effect was determined by counting the number of pupae or adult flies per sample and comparing with the number in the nonmedicated control samples. The insecticidal activity was expressed as a percent control which was defined as follows below.

$$\frac{\text{No. of pupae or adults in control} - \text{No. of pupae or adults in medicated sample}}{\text{No. of pupae or adults in control}}$$

The results are presented in Table 12.

TABLE 12

| | | Feedthrough Fecal Insecticidal Activity In Chickens Against Housefly | | | | | | | |
|---|---|---|---|---|---|---|---|---|---|
| Example No. | Conc. In Rations (ppm.) | Percent Control In Medication Week | | | | | | Percent Control After Withdrawal Week | |
| | | 0 | 1 | 2 | 3 | 4 | 5 | 1 | 2 | 3 |
| 71 | 3.8 | 0 | 71.33 | 75.65 | 82.47 | 84.33 | 77.00 | 64.33 | 33.33 | 36.03 |
| | 7.5 | 3.33 | 61.67 | 74.00 | 92.80 | 98.33 | 92.33 | 81.00 | 12.33 | 44.87 |
| | 15.0 | 8.00 | 99.00 | 100.00 | 100.00 | 100.00 | 100.00 | 100.00 | 36.00 | 27.90 |
| Control | 0 | 0 | 0 | 0 | 0 | 0 | 0 | 0 | 0 | 0 |

In general, feed consumption and weight gain of the broiler chickens that were fed the medicated feed indicate no adverse effects from the test compound. Mortality occurred only in the nontreated control group.

The data presented above shows that the feedthrough activity of the present invention is effective in suppressing mannure-breeding insects and that it continues to be effective for at least 3 weeks after the administration of active compounds is stopped.

I claim:
1. Compound of the formula

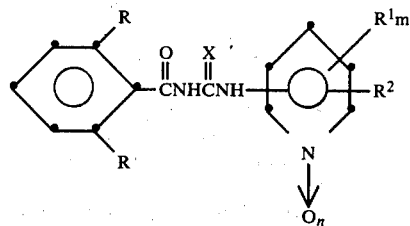

wherein each R is independently
H,
Br,
Cl,
F,
$CH_3$, or
$OCH_3$
with the proviso that both R groups are not simultaneously H, and with the further proviso that when one R group is fluoro or methoxy the other R group is not simultaneously H;
X=O or S;
n=0–1;
$R^1$ is independently
Cl,
Br,
$CH_3$, or
$CH_3CH_2$;
m=0–2; and
$R^2$ is a phenyl radical of the formula:

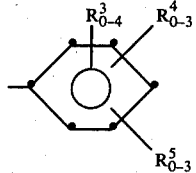

$R^3$ represents
Br,
Cl, or
F;

R⁴ represents
  $CF_3$,
  $OCF_3$,
  $OC_2F_5$,
  $OCF_2CF_2H$, or
  $SCF_3$;
R⁵ represents
  Methyl,
  Ethyl,
  Methoxy,
  Ethoxy,
  $SCH_3$, or
  $SCH_2CH_3$
with the limitation that the entire substituted phenyl radical bears
  (1) not more than 4 substituents, when all substituents are halo substituents;
  (2) not more than 3 substituents, when any one substituent is other than halo;
  (3) not more than 2 different substituents;
and wherein positions on the pyridine ring are as follows:
  (1) the NH to pyridine bond is at the 2-position of the pyridine ring, the $R^2$ group is at the 5-position of the pyridine ring, and when m=1-2, any $R^1$ is at the 4-, 6-, or 4 and 6-positions of the pyridine ring, subject to the limitation that
    (a) when simultaneously $R^1$ represents bromo and n=0, m=1 and $R^1$ is at the 6-position;
    (b) when simultaneously $R^1$ represents Cl and m=1, $R^1$ is at the 6-position;
    (c) when simultaneously m and n=0 and each R represents $OCH_3$, $R^2$ is not unsubstituted phenyl, 3-chlorophenyl, 3,4-dichlorophenyl, or 4-methoxyphenyl;
    (d) when simultaneously m and n=0 and each R represents $CH_3$, $R^2$ is not 4-chlorophenyl;
    (e) when simultaneously m and n=0 and one R represents Cl and the other R represents H, $R^2$ is not 3-chlorophenyl, 3,4-dichlorophenyl, 4-tolyl, 4-methoxyphenyl, or 3,4,5-trimethoxyphenyl;
    (f) when simultaneously m=2 and n=0 and one $R^1$ moiety represents $CH_3$ or $CH_3CH_2$, the other $R^1$ moiety is not chloro or bromo;
    (g) when n=1, neither R represents $CH_3$ or $OCH_3$, any $R^1$ represents $CH_3$ or Cl, and $R^2$ represents a para-substituted phenyl in which the substituent is Br, Cl, F, $CH_3$, or $CF_3$;
    (h) when n=1 and one R group simultaneously represents H, m=1-2; or
  (2) the NH to pyridine bond is at the 3-position of the pyridine ring, the $R^2$ group is at the 6-position of the pyridine ring, and when m=1, any $R^1$ is at the 5-position of the pyridine ring, subject to the limitation that m=0-1 and
    (a) when n=0, $R^1$ represents $CH_3$ or $CH_3CH_2$;
    (b) when simultaneously n=0 and one R represents Cl and the other R represents H, $R^2$ is not 3-chlorophenyl;
    (c) when simultaneously n=0 and one R represents $CH_3$ and the other R represents H, $R^2$ is not unsubstituted phenyl;
    (d) when n=1, each R independently represents Cl or F, any $R^1$ represents $CH_3$, and $R^2$ represents a para-substituted phenyl in which the substituent is Br, Cl, F, $CH_3$, or $CF_3$;

or an agriculturally acceptable acid addition salt thereof.

2. The compound of claim 1 wherein the NH to pyridine bond is at the 2-position of the pyridine ring, the $R^2$ group is at the 5-position of the pyridine ring, and any $R^1$ is at the 4-, 6-, or 4- and 6-positions of the pyridine ring as recited in claim 1.

3. The compound of claim 2 which is 1-(2,6-dichlorobenzoyl)-3-(5-(4-chlorophenyl)-2-pyridyl)urea or an agriculturally acceptable acid addition salt or oxide thereof.

4. The compound of claim 2 which is 1-(2,6-difluorobenzoyl)-3-(5-(4-chlorophenyl)-2-pyridyl)urea or an agriculturally acceptable acid addition salt or oxide thereof.

5. The compound of claim 2 which is 1-(2,6-dichlorobenzoyl)-3-(5-phenyl-2-pyridyl)urea or an agriculturally acceptable acid addition salt thereof.

6. The compound of claim 2 which is 1-(2,6-dimethoxybenzoyl)-3-(5-(4-chlorophenyl)-2-pyridyl)urea or an agriculturally acceptable acid addition salt thereof.

7. The compound of claim 2 which is 1-(2-chlorobenzoyl)-3-(5-(4-chlorophenyl)-2-pyridyl)urea or an agriculturally acceptable acid addition salt thereof.

8. The compound of claim 2 which is 1-(2-chloro-6-fluorobenzoyl)-3-(5-(4-chlorophenyl)-2-pyridyl)urea or an agriculturally acceptable acid addition salt or oxide thereof.

9. The compound of claim 2 which is 1-(2-chloro-6-methoxybenzoyl)-3-(5-(4-chlorophenyl)-2-pyridyl)urea or an agriculturally acceptable acid addition salt thereof.

10. The compound of claim 2 which is 1-(2,6-dichlorobenzoyl)-3-(5-(4-bromophenyl)-2-pyridyl)urea or an agriculturally acceptable acid addition salt or oxide thereof.

11. The compound of claim 2 which is 1-(2-chlorobenzoyl)-3-(5-(4-bromophenyl)-2-pyridyl)urea or an agriculturally acceptable acid addition salt thereof.

12. The compound of claim 2 which is 1-(2,6-dichlorobenzoyl)-3-(5-(4-tolyl)-2-pyridyl)urea or an agriculturally acceptable acid addition salt or oxide thereof.

13. The compound of claim 2 which is 1-(2,6-dichlorobenzoyl)-3-(5-(3-trifluoromethyl)phenyl)-2-pyridyl)urea or an agriculturally acceptable acid addition salt thereof.

14. The compound of claim 2 which is 1-(2,6-dichlorobenzoyl)-3-(5-(4-methoxyphenyl)-2-pyridyl)urea or an agriculturally acceptable acid addition salt thereof.

15. The compound of claim 2 which is 1-(2,6-dichlorobenzoyl)-3-(5-(2,4-dichlorophenyl)-2-pyridyl)urea or an agriculturally acceptable acid addition salt thereof.

16. The compound of claim 2 which is 1-(2,6-dichlorobenzoyl)-3-(5-(3,4-dichlorophenyl)-2-pyridyl)urea or an agriculturally acceptable acid addition salt thereof.

17. The compound of claim 2 which is 1-(2-chlorobenzoyl)-3-(4-methyl-5-phenyl-2-pyridyl)urea or an agriculturally acceptable acid addition salt thereof.

18. The compound of claim 2 which is 1-(2,6-difluorobenzoyl)-3-(4-methyl-5-phenyl-2-pyridyl)urea or an agriculturally acceptable acid addition salt thereof.

19. The compound of claim 2 which is 1-(2,6-difluorobenzoyl)-3-(5-(4-chlorophenyl)-4-methyl-2- pyridyl)urea or an agriculturally acceptable acid addition salt or oxide thereof.

20. The compound of claim 2 which is 1-(2-chloro-6-fluorobenzoyl)-3-(5-(4-chlorophenyl)-4-methyl-2-pyridyl)urea or an agriculturally acceptable acid addition salt or oxide thereof.

21. The compound of claim 2 which is 1-(2-chlorobenzoyl)-3-(5-(4-bromophenyl)-4-methyl-2-pyridyl)urea or an agriculturally acceptable acid addition salt or oxide thereof.

22. The compound of claim 2 which is 1-(2,6-difluorobenzoyl)-3-(5-(4-bromophenyl)-4-methyl-2-pyridyl)urea or an agriculturally acceptable acid addition salt or oxide thereof.

23. The compound of claim 2 which is 1-(2,6-difluorobenzoyl)-3-(4-methyl-5-(4-tolyl)-2-pyridyl)urea or an agriculturally acceptable acid addition salt or oxide thereof.

24. The compound of claim 2 which is 1-(2,6-dichlorobenzoyl)-3-(4-methyl-5-(4-tolyl)-2-pyridyl)urea or an agriculturally acceptable acid addition salt or oxide thereof.

25. The compound of claim 2 which is 1-(2-chlorobenzoyl)-3-(4-methyl-5-(4-tolyl)-2-pyridlyl)urea or an agriculturally acceptable acid addition salt or oxide thereof.

26. The compound of claim 2 which is 1-(2,6-dichlorobenzoyl)-3-(6-methyl-5-phenyl-2-pyridyl)urea or an agriculturally acceptable acid addition salt thereof.

27. The compound of claim 2 which is 1-(2,6-difluorobenzoyl)-3-(6-methyl-5-phenyl-2pyridyl)urea or an agriculturally acceptable acid addition salt thereof.

28. The compound of claim 2 which is 1-(2-chlorobenzoyl)-3-(6-methyl-5-phenyl-2-pyridyl)urea or an agriculturally acceptable acid addition salt thereof.

29. The compound of claim 2 which is 1-(2,6-dimethoxybenzoyl)-3-(6-methyl-5-phenyl-2-pyridyl)urea or an agriculturally acceptable acid addition salt thereof.

30. The compound of claim 2 which is 1-(2-methylbenzoyl)-3-(6-methyl-5-phenyl-2-pyridyl)urea or an agriculturally acceptable acid addition salt thereof.

31. The compound of claim 2 which is 1-(2,6-dichlorobenzoyl)-3-(5-(4-chlorophenyl)-6-methyl-2-pyridyl)urea or an agriculturally acceptable acid addition salt or oxide thereof.

32. The compound of claim 2 which is 1-(2-chlorobenzoyl)-3-(5-(4-chlorophenyl-6-methyl-2-pyridyl)urea or an agriculturally acceptable acid addition salt or oxide thereof.

33. The compound of claim 2 which is 1-(2,6-dimethoxybenzoyl)-3-(5-(4-chlorophenyl)-6-methyl-2-pyridyl)urea or an agriculturally acceptable acid addition salt thereof.

34. The compound of claim 2 which is 1-(2,6-difluorobenzoyl)-3-(5-(4-chlorophenyl)-6-methyl-2-pyridyl)urea or an agriculturally acceptable acid addition salt or oxide thereof.

35. The compound of claim 2 which is 1-(2-fluoro-6-chlorobenzoyl)-3-(5-(4-chlorophenyl)-6-methyl-2-pyridyl)urea or an agriculturally acceptable acid addition salt or oxide thereof.

36. The compound of claim 2 which is 1-(2-chloro-6-methoxybenzoyl)-3-(5-(4-chlorophenyl)-6-methyl-2-pyridyl)urea or an agriculturally acceptable acid addition salt thereof.

37. The compound of claim 2 which is 1-(2-methylbenzoyl)-3-(5-(4-chlorophenyl)-6-methyl-2-pyridyl)urea or an agriculturally acceptable acid addition salt thereof.

38. The compound of claim 2 which is 1-(2,6-dichlorobenzoyl)-3-(5-(4-methoxyphenyl)-6-methyl-2-pyridyl)urea or an agriculturally acceptable acid addition salt thereof.

39. The compound of claim 2 which is 1-(2,6-dichlorobenzoyl)-3-(6-methyl-5-(4-tolyl)-2-pyridyl)urea or an agriculturally acceptable acid addition salt or oxide thereof.

40. The compound of claim 2 which is 1-(2-chlorobenzoyl)-3-(6-methyl-5-(4-tolyl)-2-pyridyl)urea or an agriculturally acceptable acid addition salt or oxide thereof.

41. The compound of claim 2 which is 1-(2,6-difluorobenzoyl)-3-(6-methyl-5-(4-tolyl)-2-pyridyl)urea or an agriculturally acceptable acid addition salt or oxide thereof.

42. The compound of claim 2 which is 1-(2,6-difluorobenzoyl)-3-(5-(4-bromophenyl)-6-methyl-2-pyridyl)urea or an agriculturally acceptable acid addition salt or oxide thereof.

43. The compound of claim 2 which is 1-(2-chlorobenzoyl)-3-(4,6-dimethyl-5-phenyl-2-pyridyl)urea or an agriculturally acceptable acid addition salt thereof.

44. The compound of claim 2 which is 1-(2,6-dichlorobenzoyl)-3-(4,6-dimethyl-5-phenyl-2-pyridyl)urea or an agriculturally acceptable acid addition salt thereof.

45. The compound of claim 2 which is 1-(2,6-difluorobenzoyl)-3-(4,6-dimethyl-5-phenyl-2-pyridyl)urea or an agriculturally acceptable acid addition salt thereof.

46. The compound of claim 2 which is 1-(2-chlorobenzoyl)-3-(5-(4-chlorophenyl)-4,6-dimethyl-2-pyridyl)urea or an agriculturally acceptable acid addition salt or oxide thereof.

47. The compound of claim 2 which is 1-(2-chloro-6-fluorobenzoyl)-3-(5-(4-chlorophenyl)-4,6-dimethyl-2-pyridyl)urea or an agriculturally acceptable acid addition salt or oxide thereof.

48. The compound of claim 2 which is 1-(2,6-difluorobenzoyl)-3-(5-(4-chlorophenyl)-4,6-dimethyl-2-pyridyl)urea or an agriculturally acceptable acid addition salt or oxide thereof.

49. The compound of claim 2 which is 1-(2,6-difluorobenzoyl)-3-(5-(4-bromophenyl)-4,6-dimethyl-2-pyridyl)urea or an agriculturally acceptable acid addition salt or oxide thereof.

50. The compound of claim 2 which is 1-(2-chloro-6-fluorobenzoyl)-3-(5-(4-bromophenyl)-4,6-dimethyl-2-pyridyl)urea or an agriculturally acceptable acid addition salt or oxide thereof.

51. The compound of claim 2 which is 1-(2,6-difluorobenzoyl)-3-(4,6-dimethyl-5-(4-fluorophenyl)-2-pyridyl)urea or an agriculturally acceptable acid addition salt or oxide thereof.

52. The compound of claim 2 which is 1-(2,6-difluorobenzoyl)-3-(4,6-dimethyl-5-(4-methoxyphenyl)-2-pyridyl)urea or an agriculturally acceptable acid addition salt thereof.

53. The compound of claim 2 which is 1-(2,6-difluorobenzoyl)-3-(4,6-dimethyl-5-(4-(trifluoromethyl)phenyl)-2-pyridyl)urea or an agriculturally acceptable acid addition salt or oxide thereof.

54. The compound of claim 2 which is 1-(2,6-difluorobenzoyl)-3-(4,6-dimethyl-5-(3-(trifluoromethyl)phenyl)-2-pyridyl)urea or an agriculturally acceptable acid addition salt or oxide thereof.

55. The compound of claim 2 which is 1-(2,6-difluorobenzoyl)-3-(4,6-dimethyl-5-(4-tolyl)-2-pyridyl)urea or an agriculturally acceptable acid addition salt or oxide thereof.

56. The compound of claim 2 which is 1-(2,6-difluorobenzoyl)-3-(4,6-dimethyl-5-(4-(trifluoromethoxy)phenyl)-2-pyridyl)urea or an agriculturally acceptable acid addition salt or oxide thereof.

57. The compound of claim 2 which is 1-(2-bromobenzoyl)-3-(5-(4-chlorophenyl)-4,6-dimethyl-2-pyridyl)urea or an agriculturally acceptable acid addition salt or oxide thereof.

58. The compound of claim 2 which is 1-(2-chloro-6-methoxybenzoyl)-3-(5-(4-chlorophenyl)-4,6-dimethyl-2-pyridyl)urea or an agriculturally acceptable acid addition salt thereof.

59. The compound of claim 2 which is 1-(2-methylbenzoyl)-3-(5-(4-chlorophenyl)-4,6-dimethyl-2-pyridyl)urea or an agriculturally acceptable acid addition salt thereof.

60. The compound of claim 2 which is 1-(2,6-dimethylbenzoyl)-3-(5-(4-chlorophenyl)-4,6-dimethyl-2-pyridyl)urea or an agriculturally acceptable acid addition salt thereof.

61. The compound of claim 2 which is 1-(2,6-dichlorobenzoyl)-3-(5-(4-chlorophenyl)-4,6-dimethyl-2-pyridyl)urea or an agriculturally acceptable acid addition salt or oxide thereof.

62. The compound of claim 2 which is 1-(2,6-dichlorobenzoyl)-3-(6-chloro-5-(4-chlorophenyl)-2-pyridyl)urea or an agriculturally acceptable acid addition salt or oxide thereof.

63. The compound of claim 2 which is 1-(2-chlorobenzoyl)-3-(6-chloro-5-(4-chlorophenyl)-2-pyridyl)urea or an agriculturally acceptable acid addition salt or oxide thereof.

64. The compound of claim 2 which is 1-(2,6-difluorobenzoyl)-3-(6-chloro-5-(4-chlorophenyl)-2-pyridyl)urea or an agriculturally acceptable acid addition salt or oxide thereof.

65. The compound of claim 2 which is 1-(2-chloro-6-fluorobenzoyl)-3-(6-chloro-5-(4-chlorophenyl)-2-pyridyl)urea or an agriculturally acceptable acid addition salt or oxide thereof.

66. The compound of claim 2 which is 1-(2,6-difluorobenzoyl)-3-(6-bromo-5-(4-bromophenyl)-2-pyridyl)urea or an agriculturally acceptable acid addition salt thereof.

67. The compound of claim 2 which is 1-(2,6-dichlorobenzoyl)-3-(6-bromo-5-(4-chlorophenyl)-2-pyridyl)urea or an agriculturally acceptable acid addition salt thereof.

68. The compound of claim 1 wherein the NH to pyridine bond is at the 3-position of the pyridine ring, the $R^2$ group is at the 6-position of the pyridine ring, and any $R^1$ is at the 5-position of the pyridine ring as recited in claim 1.

69. The compound of claim 68 which is 1-(2,6-dichlorobenzoyl)-3-(6-(4-chlorophenyl)-3-pyridyl)urea or an agriculturally acceptable acid addition salt or oxide thereof.

70. The compound of claim 68 which is 1-(2,6-dichlorobenzoyl)-3-(6-phenyl-3-pyridyl)urea or an agriculturally acceptable acid addition salt thereof.

71. The compound of claim 68 which is 1-(2-chlorobenzoyl)-3-(6-(4-chlorophenyl)-3-pyridyl)urea or an agriculturally acceptable acid addition salt thereof.

72. The compound of claim 68 which is 1-(2,6-dimethoxybenzoyl)-3-(6-(4-chlorophenyl)-3-pyridyl)urea or an agriculturally acceptable acid addition salt thereof.

73. The compound of claim 68 which is 1-(2-chlorobenzoyl)-3-(6-(3-trifluoromethyl)phenyl)-3-pyridyl)urea or an agriculturally acceptable acid addition salt thereof.

74. The compound of claim 68 which is 1-(2,6-dichlorobenzoyl)-3-(6-(4-tolyl)-3-pyridyl)urea or an agriculturally acceptable acid addition salt or oxide thereof.

75. The compound of claim 68 which is 1-(2,6-dichlorobenzoyl)-3-(6-(4-methoxyphenyl)-3-pyridyl)urea or an agriculturally acceptable acid addition salt thereof.

76. The compound of claim 68 which is 1-(2,6-dichlorobenzoyl)-3-(5-methyl-6-phenyl-3-pyridyl)urea or an agriculturally acceptable acid addition salt thereof.

77. The compound of claim 68 which is 1-(2,6-dichlorobenzoyl)-3-(6-(4-chlorophenyl)-5-methyl-3-pyridyl)urea or an agriculturally acceptable acid addition salt or oxide thereof.

78. The compound of claim 68 which is 1-(2-chlorobenzoyl)-3-(6-(4-chlorophenyl)-5-methyl-3-pyridyl)urea or an agriculturally acceptable acid addition salt thereof.

79. The compound of claim 68 which is 1-(2,6-dimethoxybenzoyl)-3-(6-(4-chlorophenyl)-5-methyl-3-pyridyl)urea or an agriculturally acceptable acid addition salt thereof.

80. Method of suppressing insects of an order selected from the group consisting of Coleoptera, Diptera, Lepidoptera, and Orthoptera, which comprises applying to the locus of the insects an insecticidally effective amount of an active agent which is a compound of claim 1.

81. The method of claim 80 wherein in the compound of claim 1 the NH to pyridine bond is at the 2-position of the pyridine ring, the $R^2$ group is at the 5-position of the pyridine ring, and any $R^1$ is at the 4-, 6-, or 4- and 6-positions of the pyridine ring as recited in claim 1.

82. The method of claim 81 wherein the active agent is 1-(2,6-dichlorobenzoyl)-3-(5-(4-chlorophenyl)-2-pyridyl)urea or an agriculturally acceptable acid addition salt or oxide thereof.

83. The method of claim 81 wherein the active agent is 1-(2,6-difluorobenzoyl)-3-(5-(4-chlorophenyl)-2-pyridyl)urea or an agriculturally acceptable acid addition salt or oxide thereof.

84. The method of claim 81 wherein the active agent is 1-(2,6-dichlorobenzoyl)-3-(5-phenyl-2-pyridyl)urea or an agriculturally acceptable acid addition salt thereof.

85. The method of claim 81 wherein the active agent is 1-(2,6-dimethoxybenzoyl)-3-(5-(4-chlorophenyl)-2-pyridyl)urea or an agriculturally acceptable acid addition salt thereof.

86. The method of claim 81 wherein the active agent is 1-(2-chlorobenzoyl)-3-(5-(4-chlorophenyl)-2-pyridyl)urea or an agriculturally acceptable acid addition salt thereof.

87. The method of claim 81 wherein the active agent is 1-(2-chloro-6-fluorobenzoyl)-3-(5-(4-chlorophenyl)-2-

88. The method of claim 81 wherein the active agent is 1-(2-chloro-6-methoxybenzoyl)-3-(5-(4-chlorophenyl)-2-pyridyl)urea or an agriculturally acceptable acid addition salt thereof.

89. The method of claim 81 wherein the active agent is 1-(2,6-dichlorobenzoyl)-3-(5-(4-bromophenyl)-2-pyridyl urea or an agriculturally acceptable acid addition salt or oxide thereof.

90. The method of claim 81 wherein the active agent is 1-(2-chlorobenzoyl)-3-(5-(4-bromophenyl)-2-pyridyl)urea or an agriculturally acceptable acid addition salt thereof.

91. The method of claim 81 wherein the active agent is 1-(2,6-dichlorobenzoyl)-3-(5-(4-tolyl)-2-pyridyl)urea or an agriculturally acceptable acid addition salt or oxide thereof.

92. The method of claim 81 wherein the active agent is 1-(2,6-dichlorobenzoyl)-3-(5-(3-trifluoromethyl)phenyl)-2-pyridyl)urea or an agriculturally acceptable acid addition salt thereof.

93. The method of claim 81 wherein the active agent is 1-(2,6-dichlorobenzoyl)-3-(5-(4-methoxyphenyl)-2-pyridyl)urea or an agriculturally acceptable acid addition salt thereof.

94. The method of claim 81 wherein the active agent is 1-(2,6-dichlorobenzoyl)-3-(5-(2,4-dichlorophenyl)-2-pyridyl)urea or an agriculturally acceptable acid addition salt thereof.

95. The method of claim 81 wherein the active agent is 1-(2,6-dichlorobenzoyl)-3-(5-(3,4-dichlorophenyl)-2-pyridyl)urea or an agriculturally acceptable acid addition salt thereof.

96. The method of claim 81 wherein the active agent is 1-(2-chlorobenzoyl)-3-(4-methyl-5-phenyl-2-pyridyl)urea or an agriculturally acceptable acid addition salt thereof.

97. The method of claim 81 wherein the active agent is 1-(2,6-difluorobenzoyl)-3-(4-methyl-5-phenyl-2-pyridyl)urea or an agriculturally acceptable acid addition salt thereof.

98. The method of claim 81 wherein the active agent is 1-(2,6-difluorobenzoyl)-3-(5-(4-chlorophenyl)-4-methyl-2-pyridyl)urea or an agriculturally acceptable acid addition salt or oxide thereof.

99. The method of claim 81 wherein the active agent is 1-(2-chloro-6-fluorobenzoyl)-3-(5-(4-chlorophenyl)-4-methyl-2-pyridyl)urea or an agriculturally acceptable acid addition salt or oxide thereof.

100. The method of claim 81 wherein the active agent is 1-(2-chlorobenzoyl)-3-(5-(4-bromophenyl)-4-methyl-2-pyridyl)urea or an agriculturally acceptable acid addition salt or oxide thereof.

101. The method of claim 81 wherein the active agent is 1-(2,6-difluorobenzoyl)-3-(5-(4-bromophenyl)-4-methyl-2-pyridyl)urea or an agriculturally acceptable acid addition salt or oxide thereof.

102. The method of claim 81 wherein the active agent is 1-(2,6-difluorobenzoyl)-3-(4-methyl-5-(4-tolyl)-2-pyridyl)urea or an agriculturally acceptable acid addition salt or oxide thereof.

103. The method of claim 81 wherein the active agent is 1-(2,6-dichlorobenzoyl)-3-(4-methyl-5-(4-tolyl)-2-pyridyl)urea or an agriculturally acceptable acid addition salt or oxide thereof.

104. The method of claim 81 wherein the active agent is 1-(2-chlorobenzoyl)-3-(4-methyl-5-(4-tolyl)-2-pyridyl)urea or an agriculturally acceptable acid addition salt or oxide thereof.

105. The method of claim 81 wherein the active agent is 1-(2,6-dichlorobenzoyl)-3-(6-methyl-5-phenyl-2-pyridyl)urea or an agriculturally acceptable acid addition salt thereof.

106. The method of claim 81 wherein the active agent is 1-(2,6-difluorobenzoyl)-3-(6-methyl-5-phenyl-2-pyridyl)urea or an agriculturally acceptable acid addition salt thereof.

107. The method of claim 81 wherein the active agent is 1-(2-chlorobenzoyl)-3-(6-methyl-5-phenyl-2-pyridyl)urea or an agriculturally acceptable acid addition salt thereof.

108. The method of claim 81 wherein the active agent is 1-(2,6-dimethoxybenzoyl)-3-(6-methyl-5-phenyl-2-pyridyl)urea or an agriculturally acceptable acid addition salt thereof.

109. The method of claim 81 wherein the active agent is 1-(2-methylbenzoyl)-3-(6-methyl-5-phenyl-2-pyridyl)urea or an agriculturally acceptable acid addition salt thereof.

110. The method of claim 81 wherein the active agent is 1-(2,6-dichlorobenzoyl)-3-(5-(4-chlorophenyl)-6-methyl-2-pyridyl)urea or an agriculturally acceptable acid addition salt or oxide thereof.

111. The method of claim 81 wherein the active agent is 1-(2-chlorobenzyl)-3-(5-(4-chlorophenyl)-6-methyl-2-pyridyl)urea or an agriculturally acceptable acid addition salt or oxide thereof.

112. The method of claim 81 wherein the active agent is 1-(2,6-dimethoxybenzoyl)-3-(5-(4-chlorophenyl)-6-methyl-2-pyridyl)urea or an agriculturally acceptable acid addition salt thereof.

113. The method of claim 81 wherein the active agent is 1-(2,6-difluorobenzoyl)-3-(5-(4-chlorophenyl)-6-methyl-2-pyridyl)urea or an agriculturally acceptable acid addition salt or oxide thereof.

114. The method of claim 81 wherein the active agent is 1-(2-fluoro-6-chlorobenzoyl)-3-(5-(4-chlorophenyl)-6-methyl-2-pyridyl)urea or an agriculturally acceptable acid addition salt or oxide thereof.

115. The method of claim 81 wherein the active agent is 1-(2-chloro-6-methoxybenzoyl)-3-(5-(4-chlorophenyl)-6-methyl-2-pyridyl)urea or an agriculturally acceptable acid addition salt thereof.

116. The method of claim 81 wherein the active agent is 1-(2-methylbenzoyl)-3-(5-(4-chlorophenyl)-6-methyl-2-pyridyl)urea or an agriculturally acceptable acid addition salt thereof.

117. The method of claim 81 wherein the active agent is 1-(2,6-dichlorobenzoyl)-3-(5-(4-methoxyphenyl)-6-methyl-2-pyridyl)urea or an agriculturally acceptable acid addition salt thereof.

118. The method of claim 81 wherein the active agent is 1-(2,6-dichlorobenzoyl)-3-(6-methyl-5-(4-tolyl)-2-pyridyl)urea or an agriculturally acceptable acid addition salt or oxide thereof.

119. The method of claim 81 wherein the active agent is 1-(2-chlorobenzoyl)-3-(6-methyl-5-(4-tolyl)-2-pyridyl)urea or an agriculturally acceptable acid addition salt or oxide thereof.

120. The method of claim 81 wherein the active agent is 1-(2,6-difluorobenzoyl)-3-(6-methyl-5-(4-tolyl)-2-pyridyl)urea or an agriculturally acceptable acid addition salt or oxide thereof.

121. The method of claim 81 wherein the active agent is 1-(2,6-difluorobenzoyl)-3-(5-(4-bromophenyl)-6- methyl-2-pyridyl)urea or an agriculturally acceptable acid addition salt or oxide thereof.

122. The method of claim 81 wherein the active agent is 1-(2-chlorobenzoyl)-3-(4,6-dimethyl-5-phenyl-2-pyridyl)urea or an agriculturally acceptable acid addition salt thereof.

123. The method of claim 81 wherein the active agent is 1-(2,6-dichlorobenzoyl)-3-(4,6-dimethyl-5-phenyl-2-pyridyl)urea or an agriculturally acceptable acid addition salt thereof.

124. The method of claim 81 wherein the active agent is 1-(2,6-difluorobenzoyl)-3-(4,6-dimethyl-5-phenyl-2-pyridyl)urea or an agriculturally acceptable acid addition salt thereof.

125. The method of claim 81 wherein the active agent is 1-(2-chlorobenzoyl)-3-(5-(4-chlorophenyl)-4,6-dimethyl-2-pyridyl)urea or an agriculturally acceptable acid addition salt or oxide thereof.

126. The method of claim 81 wherein the active agent is 1-(2-chloro-6-fluorobenzoyl)-3-(5-(4-chlorophenyl)-4,6-dimethyl-2-pyridyl)urea or an agriculturally acceptable acid addition salt or oxide thereof.

127. The method of claim 81 wherein the active agent is 1-(2,6-difluorobenzoyl)-3-(5-(4-chlorophenyl)-4,6-dimethyl-2-pyridyl)urea or an agriculturally acceptable acid addition salt or oxide thereof.

128. The method of claim 81 wherein the active agent is 1-(2,6-difluorobenzoyl)-3-(5-(4-bromophenyl)-4,6-dimethyl-2-pyridyl)urea or an agriculturally acceptable acid addition salt or oxide thereof.

129. The method of claim 81 wherein the active agent is 1-(2-chloro-6-fluorobenzoyl)-3-(5-(4-bromophenyl)-4,6-dimethyl-2-pyridyl)urea or an agriculturally acceptable acid addition salt or oxide thereof.

130. The method of claim 81 wherein the active agent is 1-(2,6-difluorobenzoyl)-3-(4,6-dimethyl-5-(4-fluorophenyl)-2-pyridyl)urea or an agriculturally acceptable acid addition salt or oxide thereof.

131. The method of claim 81 wherein the active agent is 1-(2,6-difluorobenzoyl)-3-(4,6-dimethyl-5-(4-methoxyphenyl)-2-pyridyl)urea or an agriculturally acceptable acid addition salt thereof.

132. The method of claim 81 wherein the active agent is 1-(2,6-difluorobenzoyl)-3-(4,6-dimethyl-5-(4-(trifluoromethyl)phenyl)-2-pyridyl)urea or an agriculturally acceptable acid addition salt or oxide thereof.

133. The method of claim 81 wherein the active agent is 1-(2,6-difluorobenzoyl)-3-(4,6-dimethyl-5-(3-(trifluoromethyl)phenyl)-2-pyridyl)urea or an agriculturally acceptable acid addition salt or oxide thereof.

134. The method of claim 81 wherein the active agent is 1-(2,6-difluorobenzoyl)-3-(4,6-dimethyl-5-(4-tolyl)-2-pyridyl)urea or an agriculturally acceptable acid addition salt or oxide thereof.

135. The method of claim 81 wherein the active agent is 1-(2,6-difluorobenzoyl)-3-(4,6-dimethyl-5-(4-(trifluoromethoxy)phenyl)-2-pyridyl)urea or an agriculturally acceptable acid addition salt or oxide thereof.

136. The method of claim 81 wherein the active agent is 1-(2-bromobenzoyl)-3-(5-(4-chlorophenyl)-4,6-dimethyl-2-pyridyl)urea or an agriculturally acceptable acid addition salt or oxide thereof.

137. The method of claim 81 wherein the active agent is 1-(2-chloro-6-methoxybenzoyl)-3-(5-(4-chlorophenyl)-4,6-dimethyl-2-pyridyl)urea or an agriculturally acceptable acid addition salt thereof.

138. The method of claim 81 wherein the active agent is 1-(2-methylbenzoyl)-3-(5-(4-chlorophenyl)-4,6-dimethyl-2-pyridyl)urea or an agriculturally acceptable acid addition salt thereof.

139. The method of claim 81 wherein the active agent is 1-(2,6-dimethylbenzoyl)-3-(5-(4-chlorophenyl)-4,6-dimethyl-2-pyridyl)urea or an agriculturally acceptable acid addition salt thereof.

140. The method of claim 81 wherein the active agent is 1-(2,6-dichlorobenzoyl)-3-(5-(4-chlorophenyl)-4,6-dimethyl-2-pyridyl)urea or an agriculturally acceptable acid addition salt or oxide thereof.

141. The method of claim 81 wherein the active agent is 1-(2,6-dichlorobenzoyl)-3-(6-chloro-5-(4-chlorophenyl)-2-pyridyl)urea or an agriculturally acceptable acid addition salt or oxide thereof.

142. The method of claim 81 wherein the active agent is 1-(2-chlorobenzoyl)-3-(6-chloro-5-(4-chlorophenyl)-2-pyridyl)urea or an agriculturally acceptable acid addition salt or oxide thereof.

143. The method of claim 81 wherein the active agent is 1-(2,6-difluorobenzoyl)-3-(6-chloro-5-(4-chlorophenyl)-2-pyridyl)urea or an agriculturally acceptable acid addition salt or oxide thereof.

144. The method of claim 81 wherein the active agent is 1-(2-chloro-6-fluorobenzoyl)-3-(6-chloro-5-(4-chlorophenyl)-2-pyridyl)urea or an agriculturally acceptable acid addition salt or oxide thereof.

145. The method of claim 81 wherein the active agent is 1-(2,6-difluorobenzoyl)-3-(6-bromo-5-(4-bromophenyl)-2-pyridyl)urea or an agriculturally acceptable acid addition salt thereof.

146. The method of claim 81 wherein the active agent is 1-(2,6-dichlorobenzoyl)-3-(6-bromo-5-(4-chlorophenyl)-2-pyridyl)urea or an agriculturally acceptable acid addition salt thereof.

147. The method of claim 80 wherein in the compound of claim 1 the NH to pyridine bond is at the 3-position of the pyridine ring, the $R^2$ group is at the 6-position of the pyridine ring, and any $R^1$ is at the 5-position of the pyridine ring as recited in claim 1.

148. The method of claim 147 wherein the active agent is 1-(2,6-dichlorobenzoyl)-3-(6-(4-chlorophenyl)-3-pyridyl)urea or an agriculturally acceptable acid addition salt or oxide thereof.

149. The method of claim 147 wherein the active agent is 1-(2,6-dichlorobenzoyl)-3-(6-phenyl-3-pyridyl)urea or an agriculturally acceptable acid addition salt thereof.

150. The method of claim 147 wherein the active agent is 1-(2-chlorobenzoyl)-3-(6-(4-chlorophenyl)-3-pyridyl)urea or an agriculturally acceptable acid addition salt thereof.

151. The method of claim 147 wherein the active agent is 1-(2,6-dimethoxybenzoyl)-3-(6-(4-chlorophenyl)-3-pyridyl)urea or an agriculturally acceptable acid addition salt thereof.

152. The method of claim 147 wherein the active agent is 1-(2-chlorobenzoyl)-3-(6-(3-trifluoromethyl)phenyl)-3-pyridyl)urea or an agriculturally acceptable acid addition salt thereof.

153. The method of claim 147 wherein the active agent is 1-(2,6-dichlorobenzoyl)-3-(6-(4-tolyl)-3-pyridyl)urea or an agriculturally acceptable acid addition salt or oxide thereof.

154. The method of claim 147 wherein the active agent is 1-(2,6-dichlorobenzoyl)-3-(6-(4-methoxyphenyl)-3-pyridyl)urea or an agriculturally acceptable acid addition salt thereof.

155. The method of claim 147 wherein the active agent is 1-(2,6-dichlorobenzoyl)-3-(5-methyl-6-phenyl-3-pyridyl)urea or an agriculturally acceptable acid addition salt thereof.

156. The method of claim 147 wherein the active agent is 1-(2,6-dichlorobenzoyl)-3-(6-(4-chlorophenyl)-5-methyl-3-pyridyl)urea or an agriculturally acceptable acid addition salt or oxide thereof.

157. The method of claim 147 wherein the active agent is 1-(2-chlorobenzoyl)-3-(6-(4-chlorophenyl)-5-methyl-3-pyridyl)urea or an agriculturally acceptable acid addition salt thereof.

158. The method of claim 147 wherein the active agent is 1-(2,6-dimethoxybenzoyl)-3-(6-(4-chlorophenyl)-5-methyl-3-pyridyl)urea or an agriculturally acceptable acid addition salt thereof.

159. Composition comprising an excipient and an insecticidally effective amount of an active agent which is a compound of claim 1.

160. The composition of claim 159 wherein in the compound of claim 1 the NH to pyridine bond is at the 2-position of the pyridine ring, the $R^2$ group is at the 5-position of the pyridine ring, and any $R^1$ is at the 4-, 6-, or 4- and 6-positions of the pyridine ring as recited in claim 1.

161. The composition of claim 160 wherein the active agent is 1-(2,6-dichlorobenzoyl)-3-(5-(4-chlorophenyl)-2-pyridyl)urea or an agriculturally acceptable acid addition salt or oxide thereof.

162. The composition of claim 160 wherein the active agent is 1-(2,6-difluorobenzoyl)-3-(5-(4-chlorophenyl)-2-pyridyl)urea or an agriculturally acceptable acid addition salt or oxide thereof.

163. The composition of claim 160 wherein the active agent is 1-(2,6-dichlorobenzoyl)-3-(5-phenyl-2-pyridyl)urea or an agriculturally acceptable acid addition salt thereof.

164. The composition of claim 160 wherein the active agent is 1-(2,6-dimethoxybenzoyl)-3-(5-(4-chlorophenyl)-2-pyridyl)urea or an agriculturally acceptable acid addition salt thereof.

165. The composition of claim 160 wherein the active agent is 1-(2-chlorobenzoyl)-3-(5-(4-chlorophenyl)-2-pyridyl)urea or an agriculturally acceptable acid addition salt thereof.

166. The composition of claim 160 wherein the active agent is 1-(2-chloro-6-fluorobenzoyl)-3-(5-(4-chlorophenyl)-2-pyridyl)urea or an agriculturally acceptable acid addition salt or oxide thereof.

167. The composition of claim 160 wherein the active agent is 1-(2-chloro-6-methoxybenzoyl)-3-(5-(4-chlorophenyl)-2-pyridyl)urea or an agriculturally acceptable acid addition salt thereof.

168. The composition of claim 160 wherein the active agent is 1-(2,6-dichlorobenzoyl)-3-(5-(4-bromophenyl)-2-pyridyl)urea or an agriculturally acceptable acid addition salt or oxide thereof.

169. The composition of claim 160 wherein the active agent is 1-(2-chlorobenzoyl)-3-(5-(4-bromophenyl)-2-pyridyl)urea or an agriculturally acceptable acid addition salt thereof.

170. The composition of claim 160 wherein the active agent is 1-(2,6-dichlorobenzoyl)-3-(5-(4-tolyl)-2-pyridyl)urea or an agriculturally acceptable acid addition salt or oxide thereof.

171. The composition of claim 160 wherein the active agent is 1-(2,6-dichlorobenzoyl)-3-(5-(3-trifluoromethyl)phenyl)-2-pyridyl)urea or an agriculturally acceptable acid addition salt thereof.

172. The composition of claim 160 wherein the active agent is 1-(2,6-dichlorobenzoyl)-3-(5-(4-methoxyphenyl)-2-pyridyl)urea or an agriculturally acceptable acid addition salt thereof.

173. The composition of claim 160 wherein the active agent is 1-(2,6-dichlorobenzoyl)-3-(5-(2,4-dichlorophenyl)-2-pyridyl)urea or an agriculturally acceptable acid addition salt thereof.

174. The composition of claim 160 wherein the active agent is 1-(2,6-dichlorobenzoyl)-3-(5-(3,4-dichlorophenyl)-2-pyridyl)urea or an agriculturally acceptable acid addition salt thereof.

175. The composition of claim 160 wherein the active agent is 1-(2-chlorobenzoyl)-3-(4-methyl-5-phenyl-2-pyridyl)urea or an agriculturally acceptable acid addition salt thereof.

176. The composition of claim 160 wherein the active agent is 1-(2,6-difluorobenzoyl)-3-(4-methyl-5-phenyl-2-pyridyl)urea or an agriculturally acceptable acid addition salt thereof.

177. The composition of claim 160 wherein the active agent is 1-(2,6-difluorobenzoyl)-3-(5-(4-chlorophenyl)-4-methyl-2-pyridyl)urea or an agriculturally acceptable acid addition salt or oxide thereof.

178. The composition of claim 160 wherein the active agent is 1-(2-chloro-6-fluorobenzoyl)-3-(5-(4-chlorophenyl)-4-methyl-2-pyridyl)urea or an agriculturally acceptable acid addition salt or oxide thereof.

179. The composition of claim 160 wherein the active agent is 1-(2-chlorobenzoyl)-3-(5-(4-bromophenyl)-4-methyl-2-pyridyl)urea or an agriculturally acceptable acid addition salt or oxide thereof.

180. The composition of claim 160 wherein the active agent is 1-(2,6-difluorobenzoyl)-3-(5-(4-bromophenyl)-4-methyl-2-pyridyl)urea or an agriculturally acceptable acid addition salt or oxide thereof.

181. The composition of claim 160 wherein the active agent is 1-(2,6-difluorobenzoyl)-3-(4-methyl-5-(4-tolyl)-2-pyridyl)urea or an agriculturally acceptable acid addition salt or oxide thereof.

182. The composition of claim 160 wherein the active agent is 1-(2,6-dichlorobenzoyl)-3-(4-methyl-5-(4-tolyl)-2-pyridyl)urea or an agriculturally acceptable acid addition salt or oxide thereof.

183. The composition of claim 160 wherein the active agent is 1-(2-chlorobenzoyl)-3-(4-methyl-5-(4-tolyl)-2-pyridyl)urea or an agriculturally acceptable acid addition salt or oxide thereof.

184. The composition of claim 160 wherein the active agent is 1-(2,6-dichlorobenzoyl)-3-(6-methyl-5-phenyl-2-pyridyl)urea or an agriculturally acceptable acid addition salt thereof.

185. The composition of claim 160 wherein the active agent is 1-(2,6-difluorobenzoyl)-3-(6-methyl-5-phenyl-2-pyridyl)urea or an agriculturally acceptable acid addition salt thereof.

186. The composition of claim 160 wherein the active agent is 1-(2-chlorobenzoyl)-3-(6-methyl-5-phenyl-2-pyridyl)urea or an agriculturally acceptable acid addition salt thereof.

187. The composition of claim 160 wherein the active agent is 1-(2,6-dimethoxybenzoyl)-3-(6-methyl-5-phenyl-2-pyridyl)urea or an agriculturally acceptable acid addition salt thereof.

188. The composition of claim 160 wherein the active agent is 1-(2-methylbenzoyl)-3-(6-methyl-5-phenyl-2-

189. The composition of claim 160 wherein the active agent is 1-(2,6-dichlorobenzoyl)-3-(5-(4-chlorophenyl)-6-methyl-2-pyridyl)urea or an agriculturally acceptable acid addition salt or oxide thereof.

190. The composition of claim 160 wherein the active agent is 1-(2-chlorobenzoyl)-3-(5-(4-chlorophenyl-6-methyl-2-pyridyl)urea or an agriculturally acceptable acid addition salt or oxide thereof.

191. The composition of claim 160 wherein the active agent is 1-(2,6-dimethoxybenzoyl)-3-(5-(4-chlorophenyl)-6-methyl-2-pyridyl)urea or an agriculturally acceptable acid addition salt thereof.

192. The composition of claim 160 wherein the active agent is 1-(2,6-difluorobenzoyl)-3-(5-(4-chlorophenyl)-6-methyl-2-pyridyl)urea or an agriculturally acceptable acid addition salt or oxide thereof.

193. The composition of claim 160 wherein the active agent is 1-(2-fluoro-6-chlorobenzoyl)-3-(5-(4-chlorophenyl)-6-methyl-2-pyridyl)urea or an agriculturally acceptable acid addition salt or oxide thereof.

194. The composition of claim 160 wherein the active agent is 1-(2-chloro-6-methoxybenzoyl)-3-(5-(4-chlorophenyl)-6-methyl-2-pyridyl)urea or an agriculturally acceptable acid addition salt thereof.

195. The composition of claim 160 wherein the active agent is 1-(2-methylbenzoyl)-3-(5-(4-chlorophenyl)-6-methyl-2-pyridyl)urea or an agriculturally acceptable acid addition salt thereof.

196. The composition of claim 160 wherein the active agent is 1-(2,6-dichlorobenzoyl)-3-(5-(4-methoxyphenyl)-6-methyl-2-pyridyl)urea or an agriculturally acceptable acid addition salt thereof.

197. The composition of claim 160 wherein the active agent is 1-(2,6-dichlorobenzoyl)-3-(6-methyl-5-(4-tolyl)-2-pyridyl)urea or an agriculturally acceptable acid addition salt or oxide thereof.

198. The composition of claim 160 wherein the active agent is 1-(2-chlorobenzoyl)-3-(6-methyl-5-(4-tolyl)-2-pyridyl)urea or an agriculturally acceptable acid addition salt or oxide thereof.

199. The composition of claim 160 wherein the active agent is 1-(2,6-difluorobenzoyl)-3-(6-methyl-5-(4-tolyl)-2-pyridyl)urea or an agriculturally acceptable acid addition salt or oxide thereof.

200. The composition of claim 160 wherein the active agent is 1-(2,6-difluorobenzoyl)-3-(5-(4-bromophenyl)-6-methyl-2-pyridyl)urea or an agriculturally acceptable acid addition salt or oxide thereof.

201. The composition of claim 160 wherein the active agent is 1-(2-chlorobenzoyl)-3-(4,6-dimethyl-5-phenyl-2-pyridyl)urea or an agriculturally acceptable acid addition salt thereof.

202. The composition of claim 160 wherein the active agent is 1-(2,6-dichlorobenzoyl)-3-(4,6-dimethyl-5-phenyl-2-pyridyl)urea or an agriculturally acceptable acid addition salt thereof.

203. The composition of claim 160 wherein the active agent is 1-(2,6-difluorobenzoyl)-3-(4,6-dimethyl-5-phenyl-2-pyridyl)urea or an agriculturally acceptable acid addition salt thereof.

204. The composition of claim 160 wherein the active agent is 1-(2-chlorobenzoyl)-3-(5-(4-chlorophenyl)-4,6-dimethyl-2-pyridyl)urea or an agriculturally acceptable acid addition salt or oxide thereof.

205. The composition of claim 160 wherein the active agent is 1-(2-chloro-6-fluorobenzoyl)-3-(5-(4-chlorophenyl)-4,6-dimethyl-2-pyridyl)urea or an agriculturally acceptable acid addition salt or oxide thereof.

206. The composition of claim 160 wherein the active agent is 1-(2,6-difluorobenzoyl)-3-(5-(4-chlorophenyl)-4,6-dimethyl-2-pyridyl)urea or an agriculturally acceptable acid addition salt or oxide thereof.

207. The composition of claim 160 wherein the active agent is 1-(2,6-difluorobenzoyl)-3-(5-(4-bromophenyl)-4,6-dimethyl-2-pyridyl)urea or an agriculturally acceptable acid addition salt or oxide thereof.

208. The composition of claim 160 wherein the active agent is 1-(2-chloro-6-fluorobenzoyl)-3-(5-(4-bromophenyl)-4,6-dimethyl-2-pyridyl)urea or an agriculturally acceptable acid addition salt or oxide thereof.

209. The composition of claim 160 wherein the active agent is 1-(2,6-difluorobenzoyl)-3-(4,6-dimethyl-5-(4-fluorophenyl)-2-pyridyl)urea or an agriculturally acceptable acid addition salt or oxide thereof.

210. The composition of claim 160 wherein the active agent is 1-(2,6-difluorobenzoyl)-3-(4,6-dimethyl-5-(4-methoxyphenyl)-2-pyridyl)urea or an agriculturally acceptable acid addition salt thereof.

211. The composition of claim 160 wherein the active agent is 1-(2,6-difluorobenzoyl)-3-(4,6-dimethyl-5-(4-(trifluoromethyl)phenyl)-2-pyridyl)urea or an agriculturally acceptable acid addition salt or oxide thereof.

212. The composition of claim 160 wherein the active agent is 1-(2,6-difluorobenzoyl)-3-(4,6-dimethyl-5-(3-(trifluoromethyl)phenyl)-2-pyridyl)urea or an agriculturally acceptable acid addition salt or oxide thereof.

213. The composition of claim 160 wherein the active agent is 1-(2,6-difluorobenzoyl)-3-(4,6-dimethyl-5-(4-tolyl)-2-pyridyl)urea or an agriculturally acceptable acid addition salt or oxide thereof.

214. The composition of claim 160 wherein the active agent is 1-(2,6-difluorobenzoyl)-3-(4,6-dimethyl-5-(4-trifluoromethoxy)phenyl)-2-pyridyl)urea or an agriculturally acceptable acid addition salt or oxide thereof.

215. The composition of claim 160 wherein the active agent is 1-(2-bromobenzoyl)-3-(5-(4-chlorophenyl)-4,6-dimethyl-2-pyridyl)urea or an agriculturally acceptable acid addition salt or oxide thereof.

216. The composition of claim 160 wherein the active agent is 1-(2-chloro-6-methoxybenzoyl)-3-(5-(4-chlorophenyl)-4,6-dimethyl-2-pyridyl)urea or an agriculturally acceptable acid addition salt thereof.

217. The composition of claim 160 wherein the active agent is 1-(2-methylbenzoyl)-3-(5-(4-chlorophenyl)-4,6-dimethyl-2-pyridyl)urea or an agriculturally acceptable acid addition salt thereof.

218. The composition of claim 160 wherein the active agent is 1-(2,6-dimethylbenzoyl)-3-(5-(4-chlorophenyl)-4,6-dimethyl-2-pyridyl)urea or an agriculturally acceptable acid addition salt thereof.

219. The composition of claim 160 wherein the active agent is 1-(2,6-dichlorobenzoyl)-3-(5-(4-chlorophenyl)-4,6-dimethyl-2-pyridyl)urea or an agriculturally acceptable acid addition salt or oxide thereof.

220. The composition of claim 160 wherein the active agent is 1-(2,6-dichlorobenzoyl)-3-(6-chloro-5-(4-chlorophenyl)-2-pyridyl)urea or an agriculturally acceptable acid addition salt or oxide thereof.

221. The composition of claim 160 wherein the active agent is 1-(2-chlorobenzoyl)-3-(6-chloro-5-(4-chlorophenyl)-2-pyridyl)urea or an agriculturally acceptable acid addition salt or oxide thereof.

222. The composition of claim 160 wherein the active agent is 1-(2,6-difluorobenzoyl)-3-(6-chloro-5-(4- chlorophenyl)-2-pyridyl)urea or an agriculturally acceptable acid addition salt or oxide thereof.

223. The composition of claim 160 wherein the active agent is 1-(2-chloro-6-fluorobenzoyl)-3-(6-chloro-5-(4-chlorophenyl)-2-pyridyl)urea or an agriculturally acceptable acid addition salt or oxide thereof.

224. The composition of claim 160 wherein the active agent is 1-(2,6-difluorobenzoyl)-3-(6-bromo-5-(4-bromophenyl)-2-pyridyl)urea or an agriculturally acceptable acid addition salt thereof.

225. The composition of claim 160 wherein the active agent is 1-(2,6-dichlorobenzoyl)-3-(6-bromo-5-(4-chlorophenyl)-2-pyridyl)urea or an agriculturally acceptable acid addition salt thereof.

226. The composition of claim 159 wherein the NH to pyridine bond is at the 3-position of the pyridine ring, the $R^2$ group is at the 6-position of the pyridine ring and any $R^1$ is at the 5-position of the pyridine ring as recited in claim 1.

227. The composition of claim 226 wherein the active agent is 1-(2,6-dichlorobenzoyl)-3-(6-(4-chlorophenyl)-3-pyridyl)urea or an agriculturally acceptable acid addition salt or oxide thereof.

228. The composition of claim 226 wherein the active agent is 1-(2,6-dichlorobenzoyl)-3-(6-phenyl-3-pyridyl)urea or an agriculturally acceptable acid addition salt thereof.

229. The composition of claim 226 wherein the active agent is 1-(2-chlorobenzoyl)-3-(6-(4-chlorophenyl)-3-pyridyl)urea or an agriculturally acceptable acid addition salt thereof.

230. The composition of claim 226 wherein the active agent is 1-(2,6-dimethoxybenzoyl)-3-(6-(4-chlorophenyl)-3-pyridyl)urea or an agriculturally acceptable acid addition salt thereof.

231. The composition of claim 226 wherein the active agent is 1-(2-chlorobenzoyl)-3-(6-(3-trifluoromethyl)-phenyl)-3-pyridyl)urea or an agriculturally acceptable acid addition salt thereof.

232. The composition of claim 226 wherein the active agent is 1-(2,6-dichlorobenzoyl)-3-(6-(4-tolyl)-3-pyridyl)urea or an agriculturally acceptable acid addition salt or oxide thereof.

233. The composition of claim 226 wherein the active agent is 1-(2,6-dichlorobenzoyl)-3-(6-(4-methoxyphenyl)-3-pyridyl)urea or an agriculturally acceptable acid addition salt thereof.

234. The composition of claim 226 wherein the active agent is 1-(2,6-dichlorobenzoyl)-3-(5-methyl-6-phenyl-3-pyridyl)urea or an agriculturally acceptable acid addition salt thereof.

235. The composition of claim 226 wherein the active agent is 1-(2,6-dichlorobenzoyl)-3-(6-(4-chlorophenyl)-5-methyl-3-pyridyl)urea or an agriculturally acceptable acid addition salt or oxide thereof.

236. The composition of claim 226 wherein the active agent is 1-(2-chlorobenzoyl)-3-(6-(4-chlorophenyl)-5-methyl-3-pyridyl)urea or an agriculturally acceptable acid addition salt thereof.

237. The composition of claim 226 wherein the active agent is 1-(2,6-dimethoxybenzoyl)-3-(6-(4-chlorophenyl)-5-methyl-3-pyridyl)urea or an agriculturally acceptable acid addition salt thereof.

* * * * *